United States Patent
Ozaki

(10) Patent No.: US 11,279,958 B2
(45) Date of Patent: Mar. 22, 2022

(54) METHOD OF PRODUCING LIPID

(71) Applicant: Kao Corporation, Tokyo (JP)

(72) Inventor: Tatsuro Ozaki, Wakayama (JP)

(73) Assignee: Kao Corporation, Tokyo (JP)

(*) Notice: Subject to any disclaimer, the term of this patent is extended or adjusted under 35 U.S.C. 154(b) by 363 days.

(21) Appl. No.: 16/332,452

(22) PCT Filed: Sep. 22, 2017

(86) PCT No.: PCT/JP2017/034216
§ 371 (c)(1),
(2) Date: Mar. 12, 2019

(87) PCT Pub. No.: WO2018/062015
PCT Pub. Date: Apr. 5, 2018

(65) Prior Publication Data
US 2021/0214755 A1 Jul. 15, 2021

(30) Foreign Application Priority Data
Sep. 27, 2016 (JP) .............................. JP2016-188294

(51) Int. Cl.
*C12N 15/09* (2006.01)
*C12P 7/6409* (2022.01)
*C07K 14/405* (2006.01)
*C07K 19/00* (2006.01)
*C12N 9/04* (2006.01)
*C12P 7/64* (2022.01)

(52) U.S. Cl.
CPC .......... *C12P 7/6409* (2013.01); *C07K 14/405* (2013.01); *C07K 19/00* (2013.01); *C12N 9/0006* (2013.01); *C12P 7/64* (2013.01)

(58) Field of Classification Search
CPC ........... C12N 15/09; C12N 9/006; C12N 5/10
See application file for complete search history.

(56) References Cited

U.S. PATENT DOCUMENTS

| | | | |
|---|---|---|---|
| 10,066,248 B2 | 9/2018 | Sugihara et al. | |
| 2010/0151112 A1 | 6/2010 | Franklin et al. | |
| 2012/0277417 A1 | 11/2012 | Kilian et al. | |
| 2013/0289262 A1 | 10/2013 | Kilian et al. | |
| 2017/0044580 A1 | 2/2017 | Sugihara et al. | |
| 2019/0169659 A1 | 6/2019 | Sugihara et al. | |

FOREIGN PATENT DOCUMENTS

| | | |
|---|---|---|
| JP | 2012-510275 A | 5/2012 |
| JP | 2014-519810 A | 8/2014 |
| JP | 2017-209064 A | 11/2017 |
| WO | WO 2010/063032 A2 | 6/2010 |
| WO | WO 2012/052468 A2 | 4/2012 |
| WO | WO 2012/087676 A2 | 6/2012 |
| WO | WO 2012/149457 A2 | 11/2012 |
| WO | WO 2015/133305 A1 | 9/2015 |
| WO | WO 2018/047657 A1 | 3/2018 |

OTHER PUBLICATIONS

International Search Report (ISR) for PCT/JP2017/034216; I.A. fd Sep. 22, 2017, dated Dec. 19, 2017 from the Japan Patent Office, Tokyo, Japan.
International Preliminary Report on Patentability (IPRP), Chapter I of the Patent Cooperation Treaty, including the Written Opinion for PCT/JP2017/034216; I.A. fd Sep. 22, 2017, dated Apr. 2, 2019, by the International Bureau of WIPO, Geneva, Switzerland.
De Marchis, F. et al., "Overexpression of the olive acyl carrier protein gene (OeACP1) produces alterations in fatty acid composition of tobacco leaves," Transgenic Res. Feb. 2016;25(1):45-61. doi: 10.1007/s11248-015-9919-z. Epub Nov. 11, 2015.
Branen, JK et al., "Overexpression of acyl carrier protein-1 alters fatty acid composition of leaf tissue in *Arabidopsis*," Plant Physiol. Sep. 2001;127(1):222-9.
Database DDBJ/EMBL/GenBank [online], Accession No. JU981082, Definition: TSA: Nannochloropsis gaditana CCMP526 NGA_Contig30671 mRNA sequence, May 16, 2012 uploaded, [retrieved on Dec. 5, 2017].
Excerpted file history, U.S. Appl. No. 16/323,847: issue notification for U.S. Pat. No. 11,053,523 to issue Jul. 6, 2021 (Jun. 16, 2021); issue fee payment (Jun. 2, 2021); Rule 312 amendment with drawings (dated May 19, 2021); notice to file corrected application papers (May 12, 2021); notice of allowance (dated Apr. 28, 2021); response after final action with after final consideration program request (dated Apr. 8, 2021); final rejection (dated Dec. 10, 2020); amendment after non-final rejection (dated Nov. 19, 2020); non-final rejection (dated Jul. 23, 2020); response to election/restriction (dated Jun. 18, 2020); requirement for restriction/election (dated Apr. 20, 2020); notice of DO/EO acceptance (Feb. 27, 2019); preliminary amendment (dated Feb. 7, 2019).

*Primary Examiner* — Tekchand Saidha
(74) *Attorney, Agent, or Firm* — Sterne, Kessler, Goldstein & Fox P.L.L.C.

(57) ABSTRACT

A method of producing lipids, containing the steps of:
culturing a transformant into which a gene encoding at least one of the proteins selected from the group consisting of the following proteins (A) to (C) is introduced; and
producing fatty acids or lipids containing the same as components:
(A) A protein consisting of the amino acid sequence of the $23^{rd}$ to $146^{th}$ amino acids set forth in SEQ ID NO: 1;
(B) A protein consisting of an amino acid sequence having 70% or more identity with the amino acid sequence of the protein (A), and having acyl carrier protein activity; and
(C) A protein containing the amino acid sequence of the protein (A) or (B), and having acyl carrier protein activity.

13 Claims, No Drawings

Specification includes a Sequence Listing.

SEQUENCE LISTING

<160> NUMBER OF SEQ ID NOS: 88

<210> SEQ ID NO 1
<211> LENGTH: 146
<212> TYPE: PRT
<213> ORGANISM: Nannochloropsis oculata

<400> SEQUENCE: 1

Met Ala Leu Arg Gln Phe Leu Lys Leu Ala Ser Ser Ala Ala Arg Ser
1               5                   10                  15

Gln Ala Gln Gln Arg Gly Ile Met Thr Val Ala Arg Arg Gly Thr Pro
            20                  25                  30

Ala Leu Val Thr Ala Met Arg Gln Gln Ala Leu Leu Ala Arg Pro
         35                  40                  45

Val Val Gly Gly Leu Ser Ser Arg Asn Phe Gly Asn Ala Gln Thr Phe
 50                  55                  60

Leu Asp Glu Lys Glu Val Ala Asp Arg Val Leu Gln Val Val Lys Asn
 65                  70                  75                  80

Phe Glu Lys Val Glu Pro Gly Lys Val Thr Ala Ala Arg Phe Lys
                 85                  90                  95

Glu Asp Leu Ser Leu Asp Ser Leu Asp Val Val Glu Val Val Met Ala
                100                 105                 110

Ile Glu Glu Glu Phe Ala Leu Glu Ile Pro Asp Asn Glu Ala Asp Lys
                115                 120                 125

Ile Ala Ser Ile Gly Asp Ala Ile Lys Tyr Ile Thr Ser His Pro Gln
            130                 135                 140

Ala Lys
145

<210> SEQ ID NO 2
<211> LENGTH: 441
<212> TYPE: DNA
<213> ORGANISM: Nannochloropsis oculata

<400> SEQUENCE: 2
atggctctcc gtcaatttct gaagctggca tctagtgccg cccgctccca ggcacagcaa      60 cggggggatca tgacagtcgc tcgtcgaggg acgcctgcct tggtgacggc catgcggcag     120
caacaggcgc ttttagcccg gcctgtggtg ggggggtttga gcagccggaa ctttggcaat    180
gcgcagacgt ttctggacga gaaggaggtg gcggaccgcg ttctccaagt ggtgaagaat     240
tttgagaagg tggagcccgg gaaggtgacg gccgccgccc gcttcaagga ggatctctcc     300
ctggactcct tggacgtggt ggaggtggta atggcgatcg aggaagaatt tgcgttggag     360
attccagaca acgaggcaga taagattgct tccattggtg atgccattaa atatatcaca     420
tcccatcccc aggcaaaata a                                               441

<210> SEQ ID NO 3
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 3
atggccaagc tgaccagcgc cgttccggtg ctcaccgcgc gcgacgtcgc cggagcggtc      60
gagttctgga ccgaccggct cgggttctcc cggacttcg tggaggacga cttcgccggt      120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaacttccg ggacgcctcc gggccggcca tgaccgagat cggcgagcag     300 ccgtggggggc gggagttcgc cctgcgcgac ccggccggca actgcgtgca cttcgtggcc     360
gaggagcagg actaa                                                      375

<210> SEQ ID NO 4
<211> LENGTH: 500
<212> TYPE: DNA
<213> ORGANISM: Nannochloropsis gaditana

```
<400> SEQUENCE: 4
actgcgcatg gattgaccga cggccggttg ccaacttttg gggtcggccc ccctttttcta      60 gcccttgccc gtccagcaat taaaaattat caacggcata ccggcactgg aagcttcggg     120
tttacaattt tggcttgcct tcctaatact gtaccgcgga gaacgtatga tattacagaa     180
aaatgccttg cacagttagc gcaaagggaa aacgtttctc cgccattgta cttttttggaa    240 gagggaaagc gattgtaaaa tatggctctc cgctacgaga gtttgggctg ttgatacatg     300
tgaaaataag tgtggacgac tttgaatgac ttgatcaggc tgtttgcaca tataaccagc     360
gcgcatgcac ttctgacatg tcaatgacga aatttcacac ttcaccaata aattgtatcc     420
ttacgttttg tctttctcac acgcacatat atgatcatag ataaaagcca atatcaagaa     480
gctgtctttt ttgtgaagca                                                 500

<210> SEQ ID NO 5
<211> LENGTH: 37
<212> TYPE: DNA
<213> ORGANISM: Artificial Sequence
<220> FEATURE:
<223> OTHER INFORMATION: Primer No. 5

<400> SEQUENCE: 5
cttttttgtg aagcaatggc caagttgacc agtgccg                               37

<210> SEQ ID NO 6
<211> LENGTH: 36
<212> TYPE: DNA
<213> ORGANISM: Artificial Sequence
<220> FEATURE:
<223> OTHER INFORMATION: Primer No. 6

<400> SEQUENCE: 6
tttcccccat cccgattagt cctgctcctc ggccac                                36

<210> SEQ ID NO 7
<211> LENGTH: 35
<212> TYPE: DNA
<213> ORGANISM: Artificial Sequence
<220> FEATURE:
<223> OTHER INFORMATION: Primer No. 7

<400> SEQUENCE: 7
cgagctcggt acccgactgc gcatggattg accga                                 35

<210> SEQ ID NO 8
<211> LENGTH: 28
<212> TYPE: DNA
<213> ORGANISM: Artificial Sequence
<220> FEATURE:
<223> OTHER INFORMATION: Primer No. 8

<400> SEQUENCE: 8
tgcttcacaa aaagacagc ttcttgat                                          28

<210> SEQ ID NO 9
<211> LENGTH: 25
<212> TYPE: DNA
<213> ORGANISM: Artificial Sequence
<220> FEATURE:
<223> OTHER INFORMATION: Primer No. 9

<400> SEQUENCE: 9
tcgggatggg ggaaaaaaac ctctg                                            25
```

```
<210> SEQ ID NO 10
<211> LENGTH: 36
<212> TYPE: DNA
<213> ORGANISM: Artificial Sequence
<220> FEATURE:
<223> OTHER INFORMATION: Primer No. 10

<400> SEQUENCE: 10
actctagagg atcccctttc gtaaataaat cagctc                                36

<210> SEQ ID NO 11
<211> LENGTH: 1000
<212> TYPE: DNA
<213> ORGANISM: Nannochloropsis oculata

<400> SEQUENCE: 11
tcgggatggg ggaaaaaaac ctctgtgtgg gctgtcagtt gatactatta gaggtctttt      60
gttttgtttg tggctgcgtg tgtgtgtttg catgagaaat agacttgaga atatcggaag     120
gaactttgac atggtaaacg aggaaaagaa aatcttcaaa aaggaataat gggtaaaaac     180
aaggagcacc gggtctcttt agaaatgctt ctcggcggaa aaccagaaaa aaaggtagaa     240
tatgtcgact ttttcgctta tcattataga atgaaagatc gaatggccaa gggatttata     300
aattcttcct ttatgttgtc gtagaactta ctttccatcc cgagggaggt gtatgcaggc     360
caaaccctct gacatgggcg caatatctct atgaaaggtt gttggaatac attgtccgac     420
ctccttcgag gcggagccgc atagttgaag tataggtgct tgcttcatcc atctcatgac     480
gctttgccag tgactcactc atgcatgtga cacatttagt tctgctcgct caagcctggc     540
ccctcctgac atgcacacat tgcacttgta ggtgggccac gtttagtata dacgccaccc     600
ctgtcgcacc atcggtccca gagcaggagc acgcttccct actcctgtac gctcccctg     660 cttccccccc tgctcgtcaa cgatggcgac gccagcggct gcgaattaca gtgacggcgc     720
ggccgctcag gatgacagct cctctccttc aacatctccc aatcttccac ccccgcccat     780
gtcgtcgttc gtacggccta tgctgaccga tatgtaccaa attacaatgg tcttcgcgta     840
ctggaagcaa aagcggcacc aggacagggc catctttgag ctcttttcc ggaagacacc      900 ctttaaggga gagtttgcca ttatggccgg cattgacgaa gtactcaagt acttggccca     960 cttttcgcttc tccgaggagg agctgattta tttacgaaag                         1000

<210> SEQ ID NO 12
<211> LENGTH: 20
<212> TYPE: DNA
<213> ORGANISM: Artificial Sequence
<220> FEATURE:
<223> OTHER INFORMATION: Primer No. 12

<400> SEQUENCE: 12
gggatcctct agagtcgacc                                                  20

<210> SEQ ID NO 13
<211> LENGTH: 20
<212> TYPE: DNA
<213> ORGANISM: Artificial Sequence
<220> FEATURE:
<223> OTHER INFORMATION: Primer No. 13

<400> SEQUENCE: 13
cgggtaccga gctcgaattc                                                  20
```

<210> SEQ ID NO 14
<211> LENGTH: 36
<212> TYPE: DNA
<213> ORGANISM: Artificial Sequence
<220> FEATURE:
<223> OTHER INFORMATION: Primer No. 14

<400> SEQUENCE: 14
cagcccgcat caacaatggc tctccgtcaa tttctg                    36

<210> SEQ ID NO 15
<211> LENGTH: 35
<212> TYPE: DNA
<213> ORGANISM: Artificial Sequence
<220> FEATURE:
<223> OTHER INFORMATION: Primer No. 15

<400> SEQUENCE: 15
ctcttccaca gaagcttatt ttgcctgggg atggg                     35

<210> SEQ ID NO 16
<211> LENGTH: 35
<212> TYPE: DNA
<213> ORGANISM: Artificial Sequence
<220> FEATURE:
<223> OTHER INFORMATION: Primer No. 16

<400> SEQUENCE: 16
cgagctcggt acccgttctt ccgcttgttg ctgcc                     35

<210> SEQ ID NO 17
<211> LENGTH: 25
<212> TYPE: DNA
<213> ORGANISM: Artificial Sequence
<220> FEATURE:
<223> OTHER INFORMATION: Primer No. 17

<400> SEQUENCE: 17
tgttgatgcg ggctgagatt ggtgg                                25

<210> SEQ ID NO 18
<211> LENGTH: 21
<212> TYPE: DNA
<213> ORGANISM: Artificial Sequence
<220> FEATURE:
<223> OTHER INFORMATION: Primer No. 18

<400> SEQUENCE: 18
gcttctgtgg aagagccagt g                                    21

<210> SEQ ID NO 19
<211> LENGTH: 28
<212> TYPE: DNA
<213> ORGANISM: Artificial Sequence
<220> FEATURE:
<223> OTHER INFORMATION: Primer No. 19

<400> SEQUENCE: 19
ggcaagaaaa gctgggggaa aagacagg                             28

<210> SEQ ID NO 20
<211> LENGTH: 800
<212> TYPE: DNA
<213> ORGANISM: Nannochloropsis oculata

<400> SEQUENCE: 20

```
ttcttccgct tgttgctgcc gatggcggcc atggtctcta agatggagtg gatggaggag      60
gaggcgagcg tagcagcaag cgtgagttat acagccaggc acatgtcgca atccttcggt     120
ctcgggctta aaatccacgc actaatcacg ctgggccatg caaagagcaa tgccgaggcc     180
caccacacaa aacgctgtgt cgcgcgttgc ggcctgaagc ttcatacttc ttagtcgccg     240
ccaaaagggc tcgagagacg agacccgttg gcatgaccga tgttgttcga cgcggtttgc     300
ttcgtcacag tcgacgtgat tcaggaatct ggagcctgca gatcattttt ttcagcctga     360
tatcgttctt ttccactgag aaccatcaga ccaccttttc ttccattgtg tgaaggagta     420
ggagttgccg tgctgctttg tgggagacat ctgcgatggt gaccagcctc ccgtcgtctg     480
gtcgacgtga cgagcctctt cactgttctt cgacggagag acgcaagcga gacggctcta     540
gaccttttgg acacgcattc tgtgtgtgaa ctagtggaca gtgataccac gtctgaaagc     600
tcaccactgc ccatggtgca gctacttgtc acaaagtttt gactccgtcg gtatcaccat     660
tcgcgctcgt gtgcctggtt gttccgccac gccggcctgc cccggggcgg ggcaatattc     720
taaaatctca cgcaaaacac cgcacttacc cctcacacat attcgtgata gaccaccacc     780
aatctcagcc cgcatcaaca                                                  800

<210> SEQ ID NO 21
<211> LENGTH: 613
<212> TYPE: DNA
<213> ORGANISM: Nannochloropsis oculata

<400> SEQUENCE: 21
gcttctgtgg aagagccagt ggtagtagca gtagcagcag cagtagcagc cgcagcactc      60
agtgttggcg cgagagattg tccatccctt cttaacctac cggaagagaa ataaggcctt     120
tctcccgtag ctgtcttcgt tgtttgtgc tgattgcttg atatgagagt gttgaattcc     180
tgcatcatgt ttttctctgt agtccttttcc taccccgtc atttctttt ctccctggtt     240 cttcttttgt caccctta tt ttacataaaa tttttctttgt ttatagtgag aggaaggtag     300
agaggggaaa acaagaacaa cgaacgcaag cgtgtgaaag gagggcgagt agaagagaaa     360
cagatctgtt gagcattgag agtggagccg ggggaaaggc ttgtgtgttg tctttgaaaa     420
agttgtttaa atcacgaatc cgttagttct catgtgtacc tctttcacta catgtgatgg     480
agaaaacaaa agtgtgagga ttaattgaag aaaaagaaga gttcgacacg tcaaaccgcc     540
caaaagacgt cacaaagaga acttgattct cttttgccgtg ttgatcctgt cttttccccc     600
agcttttctt gcc                                                         613

<210> SEQ ID NO 22
<211> LENGTH: 35
<212> TYPE: DNA
<213> ORGANISM: Artificial Sequence
<220> FEATURE:
<223> OTHER INFORMATION: Primer No. 22

<400> SEQUENCE: 22
ccagcttttc ttgccactgc gcatggattg accga                                  35

<210> SEQ ID NO 23
<211> LENGTH: 36
<212> TYPE: DNA
<213> ORGANISM: Artificial Sequence
<220> FEATURE:
<223> OTHER INFORMATION: Primer No. 23
```

<400> SEQUENCE: 23
cagcccgcat caacaatgaa gaccgccgct ctcctc                                36

<210> SEQ ID NO 24
<211> LENGTH: 28
<212> TYPE: DNA
<213> ORGANISM: Artificial Sequence
<220> FEATURE:
<223> OTHER INFORMATION: Primer No. 24

<400> SEQUENCE: 24
gcgcgcaaca ccgcgggtgc gggagaac                                        28

<210> SEQ ID NO 25
<211> LENGTH: 99
<212> TYPE: DNA
<213> ORGANISM: Nannochloropsis oculata

<400> SEQUENCE: 25
atgaagaccg ccgctctcct cactgtctcc accctcatgg gcgcccaggc ctttatggcc    60
cccgccccca agttctcccg cacccgcggt gttgcgcgc                            99

<210> SEQ ID NO 26
<211> LENGTH: 37
<212> TYPE: DNA
<213> ORGANISM: Artificial Sequence
<220> FEATURE:
<223> OTHER INFORMATION: Primer No. 26

<400> SEQUENCE: 26
cgcggtgttg cgcgcatcat gacagtcgct cgtcgag                              37

<210> SEQ ID NO 27
<211> LENGTH: 475
<212> TYPE: PRT
<213> ORGANISM: Nannochloropsis oculata

<400> SEQUENCE: 27

Met Met Glu Lys Leu Thr Leu Ala Val Val Gly Ser Leu Ala Leu Thr
1               5                   10                  15

Ser Ala Phe Gln Pro Ser Ser Phe Phe Leu Arg Gln Thr Ser Ser Val
            20                  25                  30

Ser Ser Ser Ser Ser Ser Ser Arg Thr Val Arg Arg Ala Ser Gly Glu
        35                  40                  45

Val Ser Met Ala Asp Leu Pro Pro Leu Val Arg Lys Arg Val Val Ile
    50                  55                  60

Thr Gly Val Gly Ala Val Ser Pro Leu Gly Trp Gly Asp Asp Phe Trp
65                  70                  75                  80

Asn Gly Leu Val Glu Gly Arg Ser Gly Ile Val Arg Leu Pro Ser Trp
                85                  90                  95

Ala Asp Glu Tyr Pro Ala Arg Ile Gly Gly Leu Val Pro Asp His Phe
            100                 105                 110

Lys Pro Ser Asp Tyr Met Asn Ala Lys Glu Val Lys Arg Gln Ala Arg
        115                 120                 125

Phe Thr His Phe Ala Met Ala Ala Arg Met Ala Val Glu Asp Ala
    130                 135                 140

Lys Leu Asp Leu Glu Lys Val Asp Arg Ser Arg Ala Gly Cys Met Ile
145                 150                 155                 160

Gly Ser Gly Ile Gly Gly Val Glu Ile Phe Glu Lys Asn Cys Gly Glu

|     |     |     |     |     | 165 |     |     |     |     | 170 |     |     |     |     | 175 |     |     |
| --- | --- | --- | --- | --- | --- | --- | --- | --- | --- | --- | --- | --- | --- | --- | --- | --- | --- |

Phe Asp Lys Lys Gly Gly Gly Leu Pro Gly Leu Lys Ala Val Ser Pro
            180                 185                 190

Phe Leu Ile Pro Ala Leu Ile Ala Asn Thr Ala Ala Gly Thr Val Ala
        195                 200                 205

Ile Glu Leu Gly Leu Lys Gly Pro Asn Tyr Cys Ser Val Ser Ala Cys
    210                 215                 220

Ala Ser Gly Thr His Thr Ile Gly Asp Ala Phe Phe Leu Gln Asn
225                 230                 235                 240

Gly Met Ala Asp Val Cys Val Thr Gly Thr Glu Ala Ala Ile Thr
            245                 250                 255

Pro Leu Cys Phe Ala Gly Phe Val Ala Ile Arg Ala Leu Thr Thr Ser
            260                 265                 270

Gly Asn Asp Asp Pro Thr Lys Ala Ser Lys Pro Phe Asp Lys Asn Arg
            275                 280                 285

Ala Gly Phe Val Met Ala Glu Gly Ala Gly Met Leu Val Leu Glu Thr
            290                 295                 300

Glu Glu His Ala Lys Ala Arg Gly Ala Thr Ile Tyr Ala Glu Leu Ala
305                 310                 315                 320

Gly Tyr Gly Ala Ser Cys Asp Ala His His Ile Thr Ala Pro His Pro
                325                 330                 335

Glu Gly Glu Gly Leu Ala Asn Ala Met Asn Met Ala Leu Thr Ser Ala
            340                 345                 350

Gly Leu Lys Pro Thr Asp Val Asp Tyr Ile Asn Ala His Gly Thr Ser
            355                 360                 365

Thr Ala Tyr Asn Asp Lys Phe Glu Thr Leu Ala Ile His Arg Val Phe
        370                 375                 380

Gly Glu His Ala Lys Lys Leu Lys Val Ser Ser Ile Lys Ser Met Thr
385                 390                 395                 400

Gly His Ser Leu Gly Ala Ala Gly Ala Phe Glu Ala Val Ala Cys Ala
                405                 410                 415

Lys Ala Ile Lys Glu Gly Ile Ile Pro Pro Thr Ile Asn Tyr Glu Thr
            420                 425                 430

Pro Asp Pro Asp Cys Asp Leu Asp Tyr Val Pro Asn Lys Ala Ile Lys
            435                 440                 445

His Asp Val Asn Val Ala Ile Ser Asp Asn Leu Gly Phe Gly Gly His
        450                 455                 460

Asn Ala Ala Leu Val Phe Lys Lys Tyr Val Ala
465                 470                 475

<210> SEQ ID NO 28
<211> LENGTH: 1428
<212> TYPE: DNA
<213> ORGANISM: Nannochloropsis oculata

<400> SEQUENCE: 28
atgatggaga agctgaccct cgcagtggtg gctcccttg ccctgacttc ggccttccag      60
ccctcgtcct tcttcctccg gcagacttcc tccgtcagca gcagcagcag cagcagcagg     120
actgtgcgtc gtgcatcagg ggaagtgagc atggcggact tgcccccgct tgtccgcaag     180
agggtggtga tcacgggtgt cggcgccgtg tctcctctcg ggtggggaga cgacttctgg     240
aacggtctcg tggagggaag gagcggcatt gtccgcctcc cttcgtgggc ggacgagtac     300
cccgcgcgaa tcggaggctt ggtcccggat cactttaagc cgagcgacta catgaatgcc     360

```
aaggaggtga aacgacaggc ccgcttcacc cattttgcca tggcagctgc ccgtatggcc      420
gtggaagacg ccaagctcga cctggagaag gtggaccgct cgcgtgccgg gtgcatgata      480
ggatccggca ttggtggtgt agaaatcttc gagaaaaact gtggggaatt cgacaagaag      540 ggcgagggc tccctggcct caaggctgtc tccccttcc tgattccggc cctcatcgcc        600
aacaccgcag ccgggacagt ggctattgaa ctcggcttga agggcccgaa ctactgctct      660
gtctccgcct gcgcctcggg cacgcatacc atcggtgatg ccttcttctt cctccaaaac     720
ggcatggcgg acgtttgtgt aacgggcggg acggaagccg ccatcacccc cctctgtttt     780
gcgggatttg tcgccattcg cgcccttacc accagtggca acgacgaccc caccaaggcc     840
tccaagccgt tcgacaagaa ccgagccggt ttcgttatgg ccgagggagc ggggatgctc     900
gtccttgaga cggaggaaca cgcgaaggcc cgaggtgcca ccatctatgc cgagcttgct     960
ggctacggcg catcctgcga cgcccaccac atcaccgccc ccatcccga aggcgagggg     1020 ctggcgaacg cgatgaatat ggctctgacg tccgccggcc tcaagcctac ggacgtggac    1080
tacattaatg cccatggaac cagcacggcc tacaacgaca aattcgagac gctggccatt    1140
caccgcgtct ttggcgagca cgccaagaag ctgaaggttt cttccatcaa gtcaatgact    1200
ggtcactccc tcggggccgc cggtgccttc gaggccgtgg cgtgcgcgaa ggcaatcaag    1260
gagggcatca tcccgcccac catcaactac gagactcccg atccagactg cgacttggac    1320
tatgttccca caaggcgat caagcacgac gtgaatgtgg ccatctccga taacctgggc     1380
ttcggcgggc acaacgcggc tttggtcttc aagaagtatg ttgcctag                 1428

<210> SEQ ID NO 29
<211> LENGTH: 207
<212> TYPE: PRT
<213> ORGANISM: Nannochloropsis oculata

<400> SEQUENCE: 29

Met Lys Thr Ala Ala Leu Leu Thr Val Ser Thr Leu Met Gly Ala Gln
1               5                   10                  15

Ala Phe Met Ala Pro Ala Pro Lys Phe Ser Arg Thr Arg Gly Val Ala
                20                  25                  30

Arg Met Ser Phe Glu Asn Glu Ala Gly Val Thr Ala Pro Leu Gly Tyr
            35                  40                  45

Trp Asp Pro Leu Gly Leu Ser Ala Asp Gly Asp Val Asp Lys Phe Asn
        50                  55                  60

Arg Tyr Arg Ala Ile Glu Ile Lys His Gly Arg Val Ala Met Leu Ala
65                  70                  75                  80

Met Leu His Thr Leu Ile Thr Gly Ala Gly Val Thr Leu Pro Gly Leu
                85                  90                  95

Val Thr Ala Gly Asp Gly Ile Pro Gln Ser Met Pro Thr Ala Leu Ala
                100                 105                 110

Pro Tyr Ser Gly Ala Trp Ala Gln Gly Trp Ala Gln Val Leu Ile Phe
            115                 120                 125

Cys Ser Ala Leu Glu Val Leu Ala Pro Gln Lys Glu Asp Lys Ile Pro
        130                 135                 140

Gly Asp Val Gln Pro Asp Thr Ser Ala Phe Ala Lys Leu Asp Asp Lys
145                 150                 155                 160

Thr Glu Glu Glu Ala Leu Lys Tyr Gln Asn Thr Glu Ile Asn Asn Gly
                165                 170                 175

Arg Leu Ala Met Val Ala Trp Thr Gly Ala Thr Val Gly Ala Leu Leu
            180                 185                 190
```

Thr Asn Gly Glu His Pro Val Thr Thr Leu Leu Asn Lys Leu Gly
            195                 200                 205

<210> SEQ ID NO 30
<211> LENGTH: 624
<212> TYPE: DNA
<213> ORGANISM: Nannochloropsis oculata

<400> SEQUENCE: 30
atgaagaccg ccgctctcct cactgtctcc accctcatgg gcgcccaggc ctttatggcc    60
cccgccccca agttctcccg cacccgcggt gttgcgcgca tgtccttcga gaacgaggcc   120
ggcgtcaccg cccctctcgg atactgggac ccctgggcc tctccgctga tggggacgtt    180
gacaagttca accgttaccg cgccattgag atcaagcacg gccgagtcgc tatgttggcc   240
atgctccaca ccctcatcac gggcgccggt gtcacgctcc cgggcctcgt gaccgcaggt   300
gacggcatcc cccagtccat gcctacggca ttggcgccat actccggtgc gtgggcccag   360
ggctgggcgc aggtcttgat cttctgctct gccctcgagg tgcttgcccc ccagaaggag   420
gacaagatcc ccggggatgt ccagcccgac acgagcgcat cgctaagct cgacgacaag     480
accgaggagg aggcgctcaa gtaccagaac actgagatca caacggccg attggcgatg     540
gtggcttgga cgggcgcgac tgtcggtgcc ctcctgacca acggcgagca ccctgtgacc   600
accctcctca acaagttggg ctaa                                          624

<210> SEQ ID NO 31
<211> LENGTH: 120
<212> TYPE: PRT
<213> ORGANISM: Nannochloropsis oculata

<400> SEQUENCE: 31

Met Arg Val Leu Ala Phe Phe Ala Leu Leu Ala Ala Pro Ala Leu Ala
1               5                   10                  15

Phe Val Pro Arg Met Pro Ala Pro Val Arg Ala Arg Ala Ser Leu Thr
            20                  25                  30

Leu Arg Phe Ser Gly Glu Tyr Ser Glu Lys Val Arg Ala Ile Val Leu
        35                  40                  45

Glu Asn Met Gly Asp Asp Ala Lys Val Gln Asp Tyr Leu Lys Ala Asn
    50                  55                  60

Gly Asp Asp Lys Ala Glu Phe Ala Ala Met Gly Phe Asp Ser Leu Asp
65                  70                  75                  80

Leu Val Glu Phe Ser Met Ala Ile Gln Lys Glu Phe Asp Leu Pro Asp
                85                  90                  95

Leu Asn Glu Glu Asp Phe Ala Asn Leu Lys Thr Ile Lys Asp Val Val
            100                 105                 110

Thr Met Val Glu Ala Asn Lys Lys
        115                 120

<210> SEQ ID NO 32
<211> LENGTH: 363
<212> TYPE: DNA
<213> ORGANISM: Nannochloropsis oculata

<400> SEQUENCE: 32
atgcgtgtcc ttgctttctt cgccctcctg gccgcacccg ccctggcctt cgtgccccgt    60
atgcccgccc ccgtgcgtgc ccgcgccagt ctcaccctcc gattctctgg agagtacagc   120
gagaaggtgc gcgccatcgt gttggagaac atgggcgatg atgccaaggt gcaggactac   180

```
ctgaaggcca acggtgatga taaggccgag ttcgccgcca tgggctttga ttctttggac        240
ttggtggagt tctccatggc catccagaag gagttcgacc tcccggacct gaacgaggag        300
gacttcgcca acctcaagac gatcaaggac gtggtcacta tggtggaggc caacaagaag        360
taa                                                                     363
```

```
<210> SEQ ID NO 33
<211> LENGTH: 421
<212> TYPE: PRT
<213> ORGANISM: Nannochloropsis oculata

<400> SEQUENCE: 33

Met Lys Gln Cys Ser His His Val Met Pro Ser Arg Thr Pro Thr Ala
1               5                   10                  15

Phe Ser Phe Val Phe Leu Pro Ser Leu Val Leu Ser Phe Val Phe Leu
            20                  25                  30

Gln Cys Cys Thr Leu Phe Pro Ser Thr Ala Ala Phe Leu Leu Pro Ser
        35                  40                  45

Ser Ser Leu Ser Ser Thr Ser Ser Asp Tyr Tyr Ser Ser Ser Ser Leu
    50                  55                  60

Arg Arg Arg Val Ala Leu Gln Met Gln Gly Glu Gly Ser Gly Thr Gly
65                  70                  75                  80

Lys Ser Val Ala Gly Arg Ser Phe Leu Arg Ser Lys Pro Ile Gly Val
                85                  90                  95

Gly Ser Ala Ala Pro Ala Asp Val Ile Lys Asn Thr Asp Leu Glu Ser
            100                 105                 110

Val Val Glu Thr Ser Asp Glu Trp Ile Phe Thr Arg Thr Gly Ile Ser
        115                 120                 125

Gln Arg Arg Ile Leu Pro Ser Gly Gly Gln Ile Arg Gly Leu Ala Ala
    130                 135                 140

Thr Ala Ala Arg Ala Leu Glu Asn Ala Gly Leu Glu Gly Lys Asp
145                 150                 155                 160

Ile Asp Val Val Ile Leu Ala Thr Ser Ser Pro Asp Asp Leu Phe Gly
                165                 170                 175

Asp Ala Thr Ser Val Ala Ala Ala Val Gly Ala Thr Gly Ala Val Ala
            180                 185                 190

Phe Asp Leu Thr Ala Ala Cys Ser Gly Phe Leu Phe Gly Val Val Thr
        195                 200                 205

Ala Ser Gln Phe Leu His Ser Gly Cys Tyr Arg His Ala Leu Val Val
    210                 215                 220

Gly Ala Asp Ala Leu Ser Arg Trp Val Asp Trp Glu Asp Arg Asn Ser
225                 230                 235                 240

Cys Ile Leu Phe Gly Asp Gly Ala Gly Ala Val Val Leu Thr Val Ala
                245                 250                 255

Glu Gly Asp Ala Asp Ser Gly Val Leu Gly Phe Ala Met His Ser Asp
            260                 265                 270

Gly Thr Gly Gln Gly Asp Leu Asn Leu Gln Phe Ala Lys Asp Glu Ser
        275                 280                 285

Gln Ser Pro Pro Glu Ile Asn Ala Val Thr Pro Tyr Lys Gly Lys Tyr
    290                 295                 300

Asn Asn Ile Ala Met Asn Gly Lys Glu Val Tyr Lys Phe Ala Thr Arg
305                 310                 315                 320

Lys Val Pro Thr Val Ile Glu Glu Ala Leu Ala Asn Ala Gly Leu Gly
                325                 330                 335
```

Val Glu Glu Val Asp Trp Leu Leu Leu His Gln Ala Asn Ile Arg Ile
            340                 345                 350

Met Asp Val Val Ala Asp Arg Leu Gly Leu Ser Lys Asp Lys Ile Leu
            355                 360                 365

Thr Asn Leu Ser Asp Tyr Gly Asn Thr Ser Ala Gly Ser Ile Pro Leu
            370                 375                 380

Ala Leu Asp Glu Ala Val Lys Ser Gly Lys Val Lys Lys Gly Asp Ile
385                 390                 395                 400

Ile Ala Cys Ala Gly Phe Gly Ala Gly Leu Ser Trp Gly Ser Ala Ile
                405                 410                 415

Ile Arg Trp Gln Gly
            420

<210> SEQ ID NO 34
<211> LENGTH: 1266
<212> TYPE: DNA
<213> ORGANISM: Nannochloropsis oculata

<400> SEQUENCE: 34

```
atgaagcagt gcagtcatca cgtcatgcct tcacgcacac caacagcttt ctccttcgtc      60
ttcctaccct ccctcgtcct ctcgttcgtc ttcctacaat gttgcacact ttttccctcg     120
accgccgcct tcctccttcc ttcctcctcc ctctcttcca cctcctctga ctactattcc     180
tcatcctcct tgcgacgacg tgtcgccctc caaatgcaag gagaaggctc tggcaccggc     240
aaatctgtgg caggtcgttc ttttctgagg tccaagccta ttggtgtggg cagtgcggcc     300
cctgctgacg tgataaagaa cacggacctt gaaagcgtgg tggagacttc ggatgaatgg     360
attttcaccc ggacaggtat ctctcaacgc gcatccttc cctcggcggg caaattcgg      420
ggcttggccg ccacggccgc tgcccgtgct ctagaaaacg cagggctgga aggaaaggac     480
attgatgtgg tgattctcgc cacgtcttcc ccggacgatc tcttcgggga tgccacgagc     540
gtggcggcgg ccgttggtgc aacgggcgcc gtggcgtttg atttaacggc cgcttgctcg     600
ggctttctct cggcgtggt aacagcgtcg cagttcctcc actcggggtg ctaccgccac     660
gccctggtgg tgggcgctga cgccttgtcc agatggggttg actgggagga tcggaactcg     720
tgtattctgt tcggagatgg cgcaggcgcg gtggtgctga cggtggcaga aggagatgcc     780
gattcgggtg tcttgggctt tgccatgcac agcgatggga caggtcaagg cgacttgaac     840
ctccagttcg cgaaggacga gtctcagagc ccccccgaga tcaatgccgt cacgccctac     900
aagggaaagt acaacaacat tgccatgaac ggaaaggaag tgtacaaatt gccacgcgc     960
aaggtgccta ccgtcatcga agaggccttg gctaacgcgg ggctggggt agaggaggtt    1020
gactggttgt tgctgcatca ggccaacatt cgcatcatgg acgtagtggc cgaccggcta    1080
ggtctgtcga aggacaagat cctgactaac ctctccgact atggcaacac ctccgctggc    1140
tcaattcccc ttgctctcga cgaggccgtc aagtccggga aggtcaagaa aggcgacatc    1200
attgcgtgcg ctggattcgg agccggtcta tcgtggggca gcgctatcat tagatggcag    1260
ggctag                                                               1266
```

<210> SEQ ID NO 35
<211> LENGTH: 454
<212> TYPE: PRT
<213> ORGANISM: Nannochloropsis oculata

<400> SEQUENCE: 35

-continued

```
Met Arg Val Ser Ser Ala Val Leu Gly Cys Ala Leu Leu Phe Ile
1               5                   10                  15

Ala Pro Thr Leu Ala Tyr Leu Pro Thr Asn Val Arg Ala Ser Lys Gly
            20                  25                  30

Arg Ile Tyr Met Lys Glu Lys Thr Gln Arg Val Val Thr Gly Leu
            35                  40                  45

Gly Pro Ile Ser Ala Val Gly Ile Gly Lys Asp Asp Phe Trp Lys Ala
    50                  55                  60

Leu Leu Glu Gly Lys Cys Gly Ile Asp Lys Ile Ser Gly Phe Asp Pro
65                  70                  75                  80

Ser Gly Leu Thr Cys Gln Ile Gly Ala Glu Val Lys Gly Phe Asp Ala
                85                  90                  95

Lys Pro Tyr Phe Lys Asp Lys Lys Ser Ala Val Arg Asn Asp Arg Val
            100                 105                 110

Thr Leu Met Gly Val Ala Ala Ser Arg Ile Ala Val Asp Asp Ala Arg
            115                 120                 125

Leu Asp Leu Ala Thr Val Glu Gly Glu Arg Phe Gly Val Val Val Gly
    130                 135                 140

Ser Ala Phe Gly Gly Leu Gln Thr Leu Glu Thr Gln Ile Gln Ser Met
145                 150                 155                 160

Asn Glu Lys Gly Pro Gly Ala Val Ser Pro Phe Ala Val Pro Met Leu
                165                 170                 175

Leu Ser Asn Leu Ile Ser Gly Val Ile Ala Leu Glu Asn Gly Ala Lys
            180                 185                 190

Gly Pro Asn Tyr Val Val Asn Ser Ala Cys Ala Ala Ser Thr His Ala
    195                 200                 205

Leu Gly Leu Ala Tyr Ala His Ile Ala His Gly Glu Ala Asp Val Cys
210                 215                 220

Leu Ala Gly Gly Ala Glu Ala Ala Val Thr Pro Phe Gly Tyr Ala Gly
225                 230                 235                 240

Phe Cys Ser Met Lys Ala Met Ala Thr Lys Tyr Asn Asp Asn Pro Ser
                245                 250                 255

Gln Gly Ser Arg Pro Phe Asp Lys Asp Arg Cys Gly Phe Val Met Gly
            260                 265                 270

Glu Gly Ala Gly Met Leu Val Leu Glu Ser Leu Glu His Ala Gln Lys
    275                 280                 285

Arg Gly Ala His Ile Tyr Ala Glu Val Ala Gly Phe Gly Gln Ala Cys
    290                 295                 300

Asp Ala His His Ile Thr Thr Pro His Pro Glu Gly Ala Gly Leu Ala
305                 310                 315                 320

Lys Ala Ile Thr Leu Ala Leu Asp Asp Ala Gly Leu Asp Lys Gly Asp
                325                 330                 335

Leu Thr Tyr Ile Asn Ala His Gly Thr Ser Thr Ala Tyr Asn Asp Lys
            340                 345                 350

Phe Glu Thr Leu Ala Val Lys Lys Ala Leu Gly Glu Asn Ala Lys
            355                 360                 365

Arg Met Tyr Leu Ser Ser Thr Lys Gly Ser Thr Gly His Thr Leu Gly
    370                 375                 380

Ala Ala Gly Gly Leu Glu Ala Ile Ala Thr Val Leu Ala Ile Glu Thr
385                 390                 395                 400

Leu Thr Leu Pro Pro Thr Ile Asn Tyr Glu Thr Pro Asp Pro Asp Cys
            405                 410                 415

Asp Leu Asn Val Val Pro Asn Lys Pro Ile Lys Val Ala Glu Ile Lys
```

Ala Ala Ala Ser Gln Ser Ala Gly Phe Gly Gly His Asp Ser Val Val
            435                 440                 445

Ile Phe Lys Pro Phe Lys
    450

<210> SEQ ID NO 36
<211> LENGTH: 1365
<212> TYPE: DNA
<213> ORGANISM: Nannochloropsis oculata

<400> SEQUENCE: 36

```
atgcgggtct ccagtagcgc cgttttaggc tgcgccctcc tcttcatcgc cctaccttg      60
gcatacctgc ctaccaacgt gcgcgcctca aagggccgaa tctacatgaa ggagaagacc    120
caacgcgtgg tcgtgacagg cctagggccc atatcggccg tagggatcgg caaggacgat    180
ttctggaagg cgttgctaga ggggaagtgc ggcattgaca agatcagtgg ctttgaccct    240
agtggattga cgtgccaaat tggtgcggaa gtgaagggtt ttgatgcgaa gccgtatttt    300
aaggacaaga aaagcgccgt ccgtaacgac cgtgtgacac tgatgggggt ggccgcttca    360
agaatcgccg ttgatgatgc caggctggac ttggccacac tggaaggaga gcgcttcggc    420
gtggtggtgg gctccgcttt tgggggcctg caaacgctcg agacgcagat tcagagcatg    480
aatgagaagg gcccggggc tgtgtcgccc tttgcggttc ccatgttgtt gtccaacttg    540
atctcgggcg tgattgcctt ggagaacggg gcaaaggac cgaactacgt ggtgaatagc    600
gcgtgtgccg cctcgaccca tgccctcggt ctggcgtacg cccatatcgc gcacggggag    660
gcggatgtct gcttggccgg cggggcggag gctgccgtga caccgttcgg gtacgcgggg    720
ttttgctcca tgaaagccat ggcgaccaaa tacaacgaca ccctcccca aggctcccgt    780
cccttcgaca aggatcggtg cggctttgtc atgggcgagg gtgccggtat gctcgtcctc    840
gaatctctcg aacacgccca aaaacgcggc gcgcacatct atgccgaagt cgccggcttt    900
ggtcaggcct gtgacgccca ccatatcacg accccctcacc ccgaggggc gggtctggcg    960
aaagccatca ccttggcatt ggatgacgcg ggcttggaca aggtgatttt aacgtacatc   1020
aacgcccatg gcaccagcac ggcgtacaac gacaagttcg agacgttggc ggtcaagaag   1080
gccttggggg aggagaacgc caagaggatg tatttatcgt cgaccaaggg gtcgacggga   1140
cacacgctcg gggccgcggg agggttggag gcgattgcga cagtactagc gattgagacg   1200
ttgaccttgc cccccaccat caactatgag acaccagacc cggactgtga cctgaatgtg   1260
gttcccaaca aacccattaa agtggcggag atcaaagccg ctgcttctca gtcggcaggg   1320
tttggagggc atgactcggt tgtaatcttc aaaccgttca gtaa                   1365
```

<210> SEQ ID NO 37
<211> LENGTH: 348
<212> TYPE: PRT
<213> ORGANISM: Nannochloropsis oculata

<400> SEQUENCE: 37

Met Arg Ile Pro Ser Leu Ile Leu Cys Phe Ala Phe Leu Ala Ser Ala
1               5                   10                  15

Pro Ala Val Ala Phe Leu Leu Pro Pro Leu Pro Cys Phe Ser Ser Ser
                20                  25                  30

Leu Gln Thr Val Thr Asn Thr Ile Thr Thr Ser Ser Arg Phe Ser Ser
            35                  40                  45

```
Ser Ser Ser Ser Ser Ser Ser Ser Ser Ser Ser Ser Arg Pro Arg
    50                  55                  60

Cys Ser Pro Leu Leu Ser Val Thr Thr Ala Ala Thr Ala Ser Ser Ala
65                  70                  75                  80

Thr Glu Glu Ala Glu Asn Pro Ser Leu Thr Gln Gly Val Phe Ile Glu
                85                  90                  95

His Thr Asp Arg Tyr Gly Met Val Tyr His Ser Asn Tyr Leu Leu Phe
            100                 105                 110

Leu Cys Arg Ala Leu His Leu Thr Leu Gly Arg His Val Val Thr Arg
        115                 120                 125

Leu Asp Asn Phe Arg Phe Lys Ala Ser Ala Arg Leu Gly His Asp Ile
    130                 135                 140

Ala Ile Asp Val Arg Pro Lys Ala Gly Lys Asp Asn Thr Phe Val Thr
145                 150                 155                 160

Ser Ile Lys Glu Ser Glu Thr Pro His Thr Thr Phe Ile Thr Ala Asp
                165                 170                 175

Val Ser Ala Phe Pro Leu Pro Glu Arg Gly Arg Glu Gly Gly Arg Glu
            180                 185                 190

Asp Trp Ala Ala Tyr Thr Ile Ser Glu Glu Ala Leu Arg Lys Val
        195                 200                 205

Val Ala Ser Pro Asp Lys Val Met Glu Ala Val Leu Trp Thr Asp Glu
210                 215                 220

Leu Gly Val His Gly Leu Leu Thr Pro His Ala Val Leu Ser Leu Phe
225                 230                 235                 240

Glu Arg Gly Arg Ser Asp Ser Leu Gly Gly Pro Asp Arg Leu Glu Glu
        245                 250                 255

Leu Met Asp Asp Gly Tyr Met Phe Val Val Ala Arg Ile Asp Gly Tyr
    260                 265                 270

Arg Phe Asp Pro Ser Leu Arg Leu Glu Glu Gly Glu Ala Leu Gln Val
            275                 280                 285

Leu Gly Arg Phe Lys Pro Lys Ser Asp Ala Ile Val Val Cys Glu Gln
        290                 295                 300

Val Leu Ile Val Lys Ala Thr Gln Gln Ile Val Ala Gln Ala Leu Val
305                 310                 315                 320

Thr Leu Ala Cys Ile Gly Ala Val Asp Gly Lys Leu Arg Gly Val Pro
                325                 330                 335

Ser Lys Ala Leu Glu Ser Met Asn Met Gly Thr Thr
            340                 345
```

<210> SEQ ID NO 38
<211> LENGTH: 1047
<212> TYPE: DNA
<213> ORGANISM: Nannochloropsis oculata

<400> SEQUENCE: 38

```
atgagaatac cttcccttat cctttgcttc gcatttctag cgagcgctcc cgctgttgcc    60
ttcctgctgc cgccgctgcc ttgcttctct tcttcgcttc agacagtcac caacacaatc   120
acgacaagca gtcgcttcag cagcagcagc agcagcagca gcagcagcag cagcagcagc   180
agcagaccaa gatgcagccc cttgttatcc gtcacgactg ccgctactgc ttcatctgcg   240
acagaggaag cggaaaaccc gagcttgact caaggagtat tcatcgagca taccgacagg   300
tacgggatgg tctaccactc caactacctg ctcttcctct gtcgcgctct ccacctcacc   360
ctgggccggc acgtggtgac acgcctagat aactttcggt tcaaagcatc ggctcgcctg   420
```

```
ggccacgata tcgccatcga cgtgaggccc aaggcgggga agacaacac tttcgtcacc    480 agcatcaagg aaagcgaaac tcctcacact acctttatca ccgcggacgt atcggcttc    540 cccctccctg agcgaggaag ggagggagga agggaggatt gggctgcata tacgatctcg   600
gaggaagagg cattgaggaa ggtggtggcc tcccccgaca aggtcatgga ggccgttttg   660
tggaccgacg agctgggagt gcacggcctg ctcacaccgc atgccgtcct ttccctgttt   720
gagcggggaa ggagtgattc cctgggtggt ccggaccgcc tggaggagct catggatgac   780
ggctacatgt tcgtcgtcgc ccgcatcgac ggctaccgct tcgacccctc cctccgtctc   840
gaggagggag aggcccttca agtgctcggc cgatttaagc ccaagtccga cgccatcgtt   900
gtatgcgagc aggtcctcat cgtcaaggcc acccaacaga tcgtggctca ggccctcgtg   960
acgcttgcct gcatcggcgc cgtggatggc aaattgcgag cgtgccttc caaggccctt   1020 gagagtatga acatgggcac gacgtag                                       1047
```

<210> SEQ ID NO 39
<211> LENGTH: 438
<212> TYPE: PRT
<213> ORGANISM: Nannochloropsis oculata

<400> SEQUENCE: 39

```
Met Gly Arg Gly Gly Glu Lys Thr Val Thr Pro Leu Arg Lys Lys Thr
1               5                   10                  15

Leu Leu Asp Ala Ala Ser Thr Ile Ser Gly Thr Val Arg Pro Ser Lys
            20                  25                  30

Ala Val Glu Ala Leu Pro Thr Glu Glu Leu Arg Lys Lys Ala Ala Gln
        35                  40                  45

Tyr Gly Ile Asn Thr Ser Val Asp Arg Glu Thr Leu Leu Arg Glu Leu
    50                  55                  60

Ala Pro Tyr Gly Asp Ile Leu Leu Arg Asn Asp Ala Pro Lys Ser Leu
65                  70                  75                  80

Pro Leu Ala Pro Pro Phe Thr Leu Ser Asp Ile Lys Asn Ala Val
            85                  90                  95

Pro Arg His Cys Phe Glu Arg Ser Leu Ser Thr Ser Leu Phe His Leu
        100                 105                 110

Thr Ile Asp Leu Ile Gln Val Ala Val Leu Gly Tyr Leu Ala Ser Leu
    115                 120                 125

Leu Gly His Ser Asp Val Pro Pro Met Ser Arg Tyr Ile Leu Trp Pro
    130                 135                 140

Leu Tyr Trp Tyr Ala Gln Gly Ser Val Leu Thr Gly Val Trp Val Ile
145                 150                 155                 160

Ala His Glu Cys Gly His Gln Ser Phe Ser Pro Tyr Glu Ser Val Asn
            165                 170                 175

Asn Phe Phe Gly Trp Leu Leu His Ser Ala Leu Val Pro Tyr His
            180                 185                 190

Ser Trp Arg Ile Ser His Gly Lys His Asn Asn Thr Gly Ser Cys
        195                 200                 205

Glu Asn Asp Glu Val Phe Ala Pro Pro Ile Lys Glu Glu Leu Met Asp
    210                 215                 220

Glu Ile Leu Leu His Ser Pro Leu Ala Asn Leu Val Gln Ile Ile Ile
225                 230                 235                 240

Met Leu Thr Ile Gly Trp Met Pro Gly Tyr Leu Leu Leu Asn Ala Thr
            245                 250                 255

Gly Pro Arg Lys Tyr Lys Gly Leu Ser Asn Ser His Phe Asn Pro Asn
```

|     |     |     | 260 |     |     |     | 265 |     |     |     | 270 |     |     |
| --- | --- | --- | --- | --- | --- | --- | --- | --- | --- | --- | --- | --- | --- |
| Ser | Ala | Leu | Phe | Ser | Pro | Lys | Asp | Arg | Leu | Asp | Ile | Ile | Trp | Ser | Asp |
|     |     |     | 275 |     |     |     | 280 |     |     |     | 285 |     |     |

Ile Gly Phe Phe Val Ala Leu Ala Cys Val Val Tyr Ala Cys Val Gln
          290                 295                 300

Phe Gly Phe Gln Thr Val Gly Lys Tyr Tyr Leu Pro Tyr Met Val
305                 310                 315                 320

Val Asn Tyr His Leu Val Leu Ile Thr Tyr Leu Gln His Thr Asp Val
              325                 330                 335

Phe Ile Pro His Phe Arg Gly Ser Glu Trp Thr Trp Phe Arg Gly Ala
              340                 345                 350

Leu Cys Thr Val Asp Arg Ser Phe Gly Trp Leu Leu Asp His Thr Phe
              355                 360                 365

His His Ile Ser Asp Thr His Val Cys His Ile Phe Ser Lys Met
          370                 375                 380

Pro Phe Tyr His Ala Gln Glu Ala Ser Glu His Ile Arg Lys Ala Leu
385                 390                 395                 400

Gly Asp Tyr Tyr Leu Lys Asp Asp Thr Pro Ile Trp Lys Ala Leu Trp
              405                 410                 415

Arg Ser Tyr Thr Leu Cys Lys Tyr Val Asp Ser Glu Glu Thr Thr Val
              420                 425                 430

Phe Tyr Lys Gln Arg Ala
          435

<210> SEQ ID NO 40
<211> LENGTH: 1317
<212> TYPE: DNA
<213> ORGANISM: Nannochloropsis oculata

<400> SEQUENCE: 40

```
atgggacgcg gcggtgagaa gacggtgacc cctcttcgca aaaaaaccct cctggatgcc    60
gcttccacga tcagcggcac agtcagacca agcaaggcag tagaggccct gcccacggag   120
gagctgcgta agaaggccgc acaataccgg tatcaacactt cggtcgaccg cgaaacactg   180
ctgagggagc tggctcccta cggcgatatc ctcctccgca atgacgcccc taaatccctg   240
ccccttgccc ctcctccttt caccctctcc gacatcaaga acgctgttcc ccgtcactgc   300
tttgagcgtt ccctctccac ctcccctcttc cacttgacca tcgacttgat ccaagtcgct   360
gtcctcgggt accttgcctc attactgggc cactccgacg tcccgcccat gtctcgttat   420
attctatggc cgttgtactg gtacgcgcaa ggctctgtgc tgacgggagt gtgggtcatt   480
gcccacgagt gcgggcacca atcgtttttcg ccttacgaga gcgtgaacaa cttctttggg   540
tggctcttgc actcggcctt gcttgtgccc tatcactctt ggaggatttc ccatggaaag   600
caccacaaca cacggggag ctgcgagaat gacgaggtct tgcgccgcc tattaaggag   660 gaactgatgg acgagatttt gcttcactcc cctttggcga atctggtgca gataatcata   720
atgttgacca tcgatggat gccggggtac ctgctcctga acgctacggg gcctaggaaa   780
tacaagggac tgagcaatag ccactttaac ccaaattcgg cgttgttttc tccgaaggac   840
cgtctggaca ttatttggtc cgacattggg ttttttcgtgg ccttggcctg cgtggtatat   900
gcctgtgtgc agtttggatt tcaaacggtg ggaaagtatt acctgctgcc gtacatggtg   960
gtcaattatc acctggtcct catcacgtac ctgcagcaca cggacgtctt catcccccac  1020 tttcgggga gcgagtggac gtggtttagg ggcgcccttt gcacggtcga ccgatccttc  1080
```

-continued

```
ggctggcttt tggaccatac gtttcaccat atcagtgaca ctcatgtgtg ccaccacatc    1140
ttcagcaaga tgccgttcta ccacgcgcag gaggcgagtg agcacattcg caaggcgttg    1200
ggcgactatt atttgaagga tgatacccg atttggaagg cattgtggcg aagttatacc     1260
ctgtgcaagt acgtggactc ggaggagacg acggtattct acaagcagcg ggcatag       1317
```

<210> SEQ ID NO 41
<211> LENGTH: 474
<212> TYPE: PRT
<213> ORGANISM: Nannochloropsis oculata

<400> SEQUENCE: 41

```
Met Gly Arg Gly Gly Glu Arg Val Glu Thr Thr Glu Ser Leu Ser Phe
1               5                   10                  15

Thr Ala Asp Lys Ala Gly Thr Ile Lys Gln Arg Gly Gly Lys Ile Thr
            20                  25                  30

Trp Asp Glu Val Arg Gln His Lys Thr Pro Gln Asp Ala Trp Leu Val
        35                  40                  45

Tyr Arg Asn Lys Val Tyr Asp Val Ser Gly Trp Gln Asp His Pro Gly
    50                  55                  60

Gly Asn Val Ile Phe Thr His Ala Gly Gly Asp Cys Thr Asp Ile Phe
65                  70                  75                  80

Ala Ala Phe His Pro Leu Gly Ala Thr Ser Tyr Leu Asp Pro Phe Tyr
                85                  90                  95

Ile Gly Glu Leu Glu Pro Gly Ser Asp Lys Lys Pro Ala Ala Gln Ala
            100                 105                 110

Asn Phe Glu Arg Ala Tyr Arg Asp Leu Arg Gly Lys Leu Ile Ala Gly
        115                 120                 125

Gly Phe Phe Lys Ala Asn Pro Leu Tyr Tyr Val Trp Lys Val Val Ser
    130                 135                 140

Thr Val Ala Leu Ala Val Gly Ala Trp Met Leu Val Ala Trp Ser Gln
145                 150                 155                 160

Asn Leu Gly Val Gln Met Leu Ser Ala Phe Leu Val Ala Leu Phe Trp
                165                 170                 175

Gln Gln Cys Gly Trp Leu Ala His Asp Phe Leu His His Gln Val Phe
            180                 185                 190

Lys Asn Arg Ala Leu Gly Asp Leu Ala Gly Ile Val Ile Gly Asn Val
        195                 200                 205

Phe Gln Gly Phe Ser Val Ala Trp Trp Lys Asn Lys His Asn Thr His
    210                 215                 220

His Ala Val Pro Asn Leu Val Glu Ser Ser Pro Asp Ala Gln Asp Gly
225                 230                 235                 240

Asp Pro Asp Ile Asp Thr Met Pro Ile Leu Ala Trp Ser Leu Lys Met
                245                 250                 255

Ala Asp Arg Ala Gln Gln Tyr Ser Trp Gly Pro Phe Phe Val Arg His
            260                 265                 270

Gln Ser Leu Leu Tyr Phe Pro Ile Leu Leu Val Ala Arg Ile Ser Trp
        275                 280                 285

Leu Met Gln Ser Phe Leu Phe Val Phe Asp Ser Val Pro Gly Ala Ser
    290                 295                 300

Leu Trp Ala Thr Lys Gly Ala Thr Ala Glu Arg Gln Ala Ile Lys Asn
305                 310                 315                 320

Val Gly Leu Glu Lys Val Gly Leu Val Ala His Tyr Leu Trp Tyr Gly
                325                 330                 335
```

```
Ala Leu Met Leu Cys His Met Ser Leu Ala Arg Ala Leu Leu Tyr Phe
            340                 345                 350

Leu Ala Ser Gln Met Met Cys Gly Phe Leu Leu Ala Leu Val Phe Gly
        355                 360                 365

Leu Gly His Asn Gly Met Ala Val Tyr Asp Ala Asp Ala Arg Pro Asp
    370                 375                 380

Phe Trp Lys Leu Gln Val Thr Thr Arg Asn Val Thr Gly Ser Trp
385                 390                 395                 400

Leu Val Gln Trp Phe Cys Gly Gly Leu Gly Tyr Gln Val Asp His His
                405                 410                 415

Leu Phe Pro Met Ile Pro Arg His Arg Leu Gly Lys Leu His Gly Leu
            420                 425                 430

Val Glu Gly Phe Cys Lys Asp His Gly Val Lys Tyr His Glu Thr Asn
        435                 440                 445

Met Trp Glu Gly Thr Lys Glu Val Leu Ala His Leu Ser Ser Val Thr
    450                 455                 460

Lys Glu Phe Val Ala Asp Phe Pro Ala Met
465                 470
```

<210> SEQ ID NO 42
<211> LENGTH: 1425
<212> TYPE: DNA
<213> ORGANISM: Nannochloropsis oculata

<400> SEQUENCE: 42

```
atgggacgcg gtggcgagcg ggtcgagacg acggagtctt tgagcttcac ggccgacaag     60
gcggggacca tcaagcagcg tggggggaag atcacatggg atgaggtgcg tcagcacaag    120
acgcctcagg acgcttggct cgtgtatagg aataaggtct acgacgtgtc gggctggcaa    180
gatcaccccg gggggaacgt catcttcact cacgccggcg gggactgcac ggatattttc    240
gcggcgttcc accctcttgg cgccacctct tatcttgatc cattttacat tggcgagctg    300
gagccgggct cggacaagaa gcccgcagcg caggcgaact tgagcgggc ctacagggat     360
ctcaggggga agcttatcgc gggtgggttt ttcaaggcga atcctttgta ctatgtctgg    420
aaggtagtat cgacagttgc ccttgctgta ggtgcgtgga tgctggtggc ttggtcgcag    480
aacctgggcg tgcagatgct gtctgcgttt ttggtggctc tgttctggca gcaatgtggc    540
tggttggccc atgacttcct gcaccaccag gtatttaaga accgtgcgtt gggtgacctg    600
gccggcatcg ttatcggcaa tgtcttccag ggtttctccg tggcatggtg aagaacaag     660
cataacactc accacgcggt gcccaacctc gtcgagtcct ctccggacgc gcaagacgga    720
gaccctgaca ttgacaccat gcccatactg gcctggtcgc tcaagatggc cgacagggcg    780
cagcaatact catggggacc cttctttgtc aggcatcagt cgctgctata cttccccatc    840
ctgctcgtgg cgcggatttc atggttgatg cagtcgttct tgtttgtctt tgactccgtc    900
cctggagcga gtctgtgggc aaccaagggc gcgacggctg agagacaggc gatcaagaat    960
gtcgggttgg agaaggtggg gctggttgcg cactacctgt ggtacggtgc gctgatgctg   1020
tgccacatgt ccctggcccg cgccctgctg tacttcctgg cgagccagat gatgtgcggg   1080
ttcttgctcg cgcttgtttt cgggcttggg cacaacggca tggctgttta cgacgcggac   1140
gcccggcccg acttctggaa gctgcaggtg acgacgacga ggaacgtgac gggctcgtgg   1200
ttggtgcagt ggttctgtgg cggcctcggc taccaggtgg accaccacct gttccccatg   1260
atcccgcggc accgcctagg gaagctccac gggctcgtgg agggtttctg caaggatcac   1320
```

```
ggggtgaagt accacgagac gaatatgtgg gaggggacca aagaggtgtt ggctcacttg   1380
agcagtgtga cgaaagagtt cgtggccgat ttccccgcca tgtaa                  1425
```

<210> SEQ ID NO 43
<211> LENGTH: 410
<212> TYPE: PRT
<213> ORGANISM: Nannochloropsis oculata

<400> SEQUENCE: 43

```
Met Val Glu Gln Thr Leu Pro Thr Leu Ser Gln Ile Lys Lys Ala Ile
1               5                   10                  15

Pro Glu Lys Cys Phe Gln Lys Ser Leu Leu Arg Ser Phe Tyr Tyr Met
            20                  25                  30

Leu Arg Asp Phe Ala Ala Leu Ala Ala Leu Tyr Phe Val Tyr Pro Thr
        35                  40                  45

Val Gln Ala Lys Tyr Gly Leu Pro Gly Leu Phe Val Trp Trp Asn Leu
    50                  55                  60

Ala Gly Phe Phe Met Trp Cys Leu Phe Val Ile Gly His Asp Cys Gly
65                  70                  75                  80

His Gly Ser Phe Ser Glu Tyr Lys Trp Leu Asn Asp Ile Cys Gly His
                85                  90                  95

Ile Cys His Ala Pro Leu Met Val Pro Tyr Trp Pro Trp Gln Lys Ser
            100                 105                 110

His Arg Leu His His Met Tyr His Asn His Leu Thr Lys Asp Met Ser
        115                 120                 125

His Pro Trp Met Thr Lys Glu Val Phe Glu Asp Leu Thr Pro Phe Glu
    130                 135                 140

Gln Ala Leu Leu Glu Asn Pro Leu Ser Leu Phe Ile Lys Tyr Thr Phe
145                 150                 155                 160

Leu Tyr Leu Phe Ala Gly Lys Met Asp Gly Ser His Val Val Pro Phe
                165                 170                 175

Ser Pro Leu Phe Thr Asp Thr Lys Glu Arg Val Gln Cys Ala Val Ser
            180                 185                 190

Thr Leu Gly Met Val Val Ala Gly Ala Leu Val Tyr Ile Gly Leu Glu
        195                 200                 205

Gly Gly Lys Glu Gly Gly Met Ala Arg Ile Gly Ser Ile Tyr Val Val
    210                 215                 220

Pro Leu Leu Val Phe Asn Ala Trp Ile Thr Met Val Thr Tyr Leu Gln
225                 230                 235                 240

His His Asp Glu Asp Thr Lys Val Tyr Ala Glu Gly Glu Trp Asn Tyr
                245                 250                 255

Ile Lys Gly Ala Leu Glu Thr Ile Asp Arg Glu Tyr Gly Met Gly Ile
            260                 265                 270

Asp Asp Leu Ser His Asn Ile Thr Asp Gly His Val Ala His His Leu
        275                 280                 285

Phe Phe Thr Gln Ile Pro His Tyr His Leu Thr Ala Ala Thr Ala Ala
    290                 295                 300

Val Arg Gln Cys Leu Gln Pro Thr Gly Thr Tyr Lys Lys Arg Arg Ser
305                 310                 315                 320

Trp Asn Phe Leu Ala Arg Phe Thr Glu Leu Asn Tyr Arg Leu Lys Tyr
                325                 330                 335

Val Ala Gly Gln Gly Val Leu Ser Tyr Val Asp Trp Glu Val Ala Arg
            340                 345                 350

Lys Thr Pro Ala Ser Ala Val Thr Ser Ser Phe Ser Ser Ser Ser Ser
```

```
             355                 360                 365
Ser Ser Leu Pro Ala Glu Ala Ala Val Lys Ala Ala Ala Val Pro
        370                 375                 380

Val Ala Val Ala Ala Pro Val Arg Glu Gly Arg Pro Thr Arg Lys
385                 390                 395                 400

Arg Ser Pro Thr Arg Ser Ser Pro Pro
                405                 410

<210> SEQ ID NO 44
<211> LENGTH: 1233
<212> TYPE: DNA
<213> ORGANISM: Nannochloropsis oculata

<400> SEQUENCE: 44
atggttgagc aaacgttacc gaccttgtcc cagatcaaga aagccatccc cgagaaatgc      60
ttccagaaat ccctcctccg ctccttttac tacatgctga gggacttcgc ggccttggcg     120
gcactctact ttgtttatcc cacagttcag gccaagtatg gattgcctgg tttgtttgtg     180
tggtggaacc tcgcaggctt tttcatgtgg tgcctcttcg tgataggcca cgattgcggc     240
catggctcct tctccgagta caagtggctc aatgacattt gcggtcacat ttgccacgcc     300
cccttgatgg tgccttactg gccttggcag aagtcccacc gccttcacca catgtaccac     360
aaccacctga ctaaggacat gtcacacccg tggatgacca aggaggtgtt cgaggacttg     420
accccattcg agcaggcgtt gctggagaac ccgctgtccc tcttcatcaa gtacaccttc     480
ctttacctct tgcgggcaa gatggatggc agccatgtag ttccattctc ccccctcttc     540
accgacacca aggagcgggt gcaatgcgca gtgtcgacgc tgggtatggt cgtcgcaggc     600
gcccttgtgt acatcgggct cgagggcggg aaggagggag ggatggcgag ataggatcc     660 atttatgtgg tgccgttgct ggtgttcaat gcctggatca cgatggtgac ataccctgcag   720 caccacgatg aggacaccaa ggtttatgca gaggggagt ggaactacat caaggggcc      780 ctggagacga tcgaccgcga atacggcatg gggattgacg acctctccca caatatcacg     840
gatggccacg tggcgcacca cctcttcttc acgcagatcc cgcactacca cctgacggcg     900
gccacggccg ctgtgagaca atgcctgcaa cctacgggga cctacaagaa gaggaggagc     960 tggaatttc tcgctcgttt cacggagctt aactaccgtt tgaaatacgt cgcgggccag    1020
ggcgtgctct cctatgtgga ttggaggtc gctcgcaaga cccctgcttc cgccgtcacc    1080 tcctcttct cttcctcctc ctcttcctcc cttccggcag aggctgctgt caaggcggct    1140
gctgccgttc ccgttgctgc tgttgctgct cccgtccgag aaggaagacc aacacgcaag    1200
cgctctccca cccgttcatc ctcccctccg taa                                1233

<210> SEQ ID NO 45
<211> LENGTH: 526
<212> TYPE: PRT
<213> ORGANISM: Nannochloropsis oculata

<400> SEQUENCE: 45

Met Pro Pro Gln Asn Asp Ala Ala Leu Gly Gly Gly Phe Phe Arg Asn
1               5                   10                  15

Arg Phe Thr Arg Lys Asn Ser Thr Ser Ser Leu Ile Ile Asp Asp Thr
            20                  25                  30

Pro Ala Thr Ser Thr Glu Ser Val Ala Ala Glu Ala Thr Val Ala
        35                  40                  45

Ala Thr Ala Ala Ala Ala Ala Gly Gly Lys Thr Tyr Thr Trp Glu Glu
```

```
                50                  55                  60
Val Ala Glu His Asn Thr Glu Lys Ser Leu Trp Val Thr Val Arg Gly
 65                  70                  75                  80

Lys Val Tyr Asp Ile Ser Ser Trp Val Asn Asn His Pro Gly Gly Lys
                 85                  90                  95

Glu Ile Leu Leu Leu Ala Ala Gly Arg Asp Ile Thr Tyr Ala Phe Asp
                100                 105                 110

Ser Tyr His Pro Phe Thr Glu Lys Pro Thr Gln Val Leu Gly Lys Phe
                115                 120                 125

Glu Ile Gly Thr Val Ser Ser His Glu Phe Pro Gln Tyr Lys Pro Asp
                130                 135                 140

Thr Arg Gly Phe Tyr Lys Thr Leu Cys Thr Arg Val Gly Asp Tyr Phe
145                 150                 155                 160

Lys Gln Glu Lys Leu Asn Pro Lys Asp Pro Phe Pro Gly Ile Trp Arg
                165                 170                 175

Met Leu Leu Val Ala Met Val Ala Val Ala Ser Phe Met Val Cys Asn
                180                 185                 190

Gly Trp Val Gly Leu Glu Gly Gly Val Leu Ala Gly Trp Gly Ala Arg
                195                 200                 205

Phe Val Ala Ala Val Val Phe Gly Val Cys Gln Ala Leu Pro Leu Leu
                210                 215                 220

His Val Met His Asp Ser Ser His Leu Ala Phe Gly Asn Thr Glu Arg
225                 230                 235                 240

Trp Trp Gln Met Gly Gly Arg Leu Ala Met Asp Phe Phe Ala Gly Ala
                245                 250                 255

Asn Met Thr Ser Trp His Asn Gln His Val Ile Gly His His Ile Tyr
                260                 265                 270

Thr Asn Val Phe Met Ala Asp Pro Asp Leu Pro Asp Lys Ser Ala Gly
                275                 280                 285

Asp Pro Arg Arg Leu Val Lys Lys Gln Ala Trp Glu Gly Met Tyr Lys
                290                 295                 300

Trp Gln His Leu Tyr Leu Pro Pro Leu Tyr Gly Ile Leu Gly Ile Lys
305                 310                 315                 320

Phe Arg Val Gln Asp Val Met Glu Thr Tyr Gly Ser Gly Ser Asn Gly
                325                 330                 335

Pro Val Arg Val Asn Pro Leu Ser Pro Trp Gln Trp Gly Glu Met Ile
                340                 345                 350

Phe Thr Lys Leu Phe Trp Phe Gly Trp Arg Val Val Phe Pro Leu Met
                355                 360                 365

Ser Ala Ser Phe Arg Thr Ser Met Ala Thr Phe Trp Pro Leu Phe Phe
                370                 375                 380

Val Ser Glu Phe Met Thr Gly Tyr Phe Leu Ala Phe Asn Phe Gln Val
385                 390                 395                 400

Ser His Val Ser Ser Glu Cys Asp Tyr Pro Leu Gly Glu Ala Pro Arg
                405                 410                 415

Glu Glu Ala Val Glu Gly Ser Ala Gly Gly Lys Glu Gly Ile Lys Asp
                420                 425                 430

Glu Trp Ala Val Ser Gln Val Lys Ser Ser Val Asp Tyr Ala His Asn
                435                 440                 445

Asn Ala Leu Thr Thr Phe Leu Cys Gly Ala Leu Asn Tyr Gln Val Thr
                450                 455                 460

His His Leu Phe Pro Thr Val Ser Gln Tyr His Tyr Pro Lys Ile Ala
465                 470                 475                 480
```

```
Pro Ile Ile Gln Glu Val Cys Lys Glu Phe Asn Val Asp Tyr Lys Val
                485                 490                 495

Leu Pro Asp Phe Val Thr Ala Phe His Ala His Ile Ala His Leu Lys
            500                 505                 510

Ala Leu Gly Glu Arg Gly Glu Ala Ala Glu Val His Met Gly
        515                 520                 525

<210> SEQ ID NO 46
<211> LENGTH: 1581
<212> TYPE: DNA
<213> ORGANISM: Nannochloropsis oculata

<400> SEQUENCE: 46
atgcctcccc agaacgacgc tgctcttgga ggcggttttt ttcgcaaccg cttcacccga      60
aagaactcca cttcctccct catcatcgat gacacgccgg ccaccagcac tgagtccgtg     120
gcggcagcag aagcaacagt agcagcgaca gcagccgccg ccgccggcgg taagacctac     180
acatgggagg aagtggcgga gcacaacact gagaagagcc tgtgggtgac cgtgcgagga     240
aaggtgtatg acatcagcag ctgggtgaac aaccacccgg agggaaggga gattctgttg     300
ttggcggcgg gcagggatat cacctatgcc ttcgactctt accacccttt cacggagaag     360
ccgacgcagg tcctgggcaa gtttgagatc ggcactgtgt cctcccacga attcccgcag     420
tacaaacccg acacccgggg cttctacaag acgctgtgca cgcgcgtagg tgactacttt     480
aagcaggaga agttgaaccc taaggaccct ttcccaggga tatggcggat gctcctggtg     540
gcgatggtgg ccgtagcctc ctttatggtg tgcaacgggt gggtggggct ggaaggaggg     600
gtactggcag gatggggagc gaggtttgtg gcggcggtgg tgtttggtgt gtgccaggcg     660
ttgccccttc tgcacgtcat gcacgactca tcccacctgg cgttcgggaa cacggagagg     720
tggtggcaaa tgggggggag gctggccatg gatttcttcg cggggcgaaa catgacgagt     780
tggcacaatc agcacgtgat agggcatcac atttatacga atgtgttcat ggctgacccg     840
gacttgcccg ataagagcgc tggggacccg aggcggctgg ttaagaagca ggcatgggag     900
gggatgtaca agtggcagca cctctacttg ccacctttgt acggcatcct gggcatcaag     960
ttccgggtgc aagacgtgat ggagacgtac gggagcgggt cgaatgggcc ggtgagggtt    1020
aaccccttga gccctggca gtgggggag atgatcttca ccaagctctt ctggttcggc    1080
tggcgcgtgg tgttcccgct catgtcggca gctttcggac gagcatggc cacgttctgg    1140 cccttgttct tcgtgagtga gttcatgacg ggatacttcc tggcgttcaa tttccaggtg    1200
tcacacgtct cgtccgagtg cgattatccg ctgggcgagg cgccgaggga ggaagcggta    1260
gagggctcgg caggagggaa ggaaggtatc aaggacgaat gggccgtgag ccaggtgaag    1320
agtagcgtgg actacgccca caataacgct ttgacgacct tcctgtgcgg ggctttgaac    1380
taccaggtga cgcaccacct gttccccact gtaagtcagt accactaccc caagatcgcg    1440
cccatcatcc aggaggtatg caaggagttt aacgtcgact acaaggtcct gcccgatttt    1500
gtgacggcgt tccatgcgca cattgcgcat ttgaaggcct gggagagag gggcgaggcg    1560 gcggaggtgc acatgggtta g                                              1581

<210> SEQ ID NO 47
<211> LENGTH: 359
<212> TYPE: PRT
<213> ORGANISM: Nannochloropsis oculata

<400> SEQUENCE: 47
```

```
Met Val Phe Gln Leu Ala Arg Asp Ser Val Ser Ala Leu Val Tyr His
1               5                   10                  15

Phe Lys Glu Gly Asn Leu Asn Trp Pro Met Ile Ile Tyr Leu Val Leu
            20                  25                  30

Val His Leu Ala Gly Tyr Ile Gly Leu Thr Thr Ile Leu Ala Cys Lys
        35                  40                  45

Trp Gln Thr Leu Leu Glu Ala Phe Ile Leu Trp Pro Ile Thr Gly Leu
    50                  55                  60

Gly Ile Thr Ala Gly Val His Arg Leu Trp Ala His Arg Ser Tyr Asn
65              70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
130             135                 140

Val Glu Gly Gly Lys Gln Leu Asp Phe Ser Asp Leu Ala Ala Asp Pro
145             150                 155                 160

Val Val Arg Phe Gln Arg Asp Trp Asp Pro Trp Phe Ala Gln Phe Met
                165                 170                 175

Cys Phe Val Met Pro Ala Leu Val Ala Ser Arg Phe Trp Gly Glu Ala
            180                 185                 190

Phe Trp Asn Ala Phe Trp Val Ala Gly Ala Leu Arg Tyr Met Leu Val
        195                 200                 205

Leu His Phe Thr Trp Met Val Asn Ser Ala Ala His Leu Tyr Gly Asp
    210                 215                 220

His Pro Tyr Asp Pro Thr Met Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Gln Gln Phe Asn Pro
            260                 265                 270

Thr Lys Ala Phe Ile Asp Phe Phe Ala Ala Ile Gly Met Val Thr Asn
        275                 280                 285

Arg Lys Arg Ala Thr Gly Ala Trp Ala Lys Leu Lys Glu Ser Arg Ala
290             295                 300

Arg Asp Ala Ala Asn Gly Lys Ser Met Lys Asp Phe Lys Gly Arg Gly
305                 310                 315                 320

Ser Gly Ser Asp Tyr Gly Thr Thr Asn Thr Tyr Ala Val Ser Asn
            325                 330                 335

Lys Thr Val Val Thr Asp Lys Gly Ala Gln Gln Pro Gly Trp Glu Glu
        340                 345                 350

Ser Asn His Pro Lys Tyr Asn
            355
```

<210> SEQ ID NO 48
<211> LENGTH: 1080
<212> TYPE: DNA
<213> ORGANISM: Nannochloropsis oculata

<400> SEQUENCE: 48
atggtcttcc agctcgcccg agactctgtc tcggccctgg tctatcattt caaagaagga    60

```
aaccttaact ggcctatgat tatctacctc gtccttgtcc acttggcggg ctacatcggt    120
ctgactacca ttctggcttg caaatggcaa actctcctcg aagcgttcat cctatggccc    180
atcaccgggc tggggattac tgccggcgta caccgacttt gggcacaccg ttcgtacaat    240
gccacgttgc cttatcgcat cctgttgatg ttgttcaact caattgcgaa ccaaggcagc    300
atctaccact ggtcccggga ccaccgcgtg caccacaagt actccgagac tgatgctgac    360
ccacataacg ccaccgtgg cttcttcttc gcgcacatgg gctggctcat tgttaagaag    420
caccccaagg tcgtcgaagg ggggaagcaa ctcgatttct ccgatttggc tgccgatccc    480
gtggtgcgat tccagcgtga ttgggatccg tggttcgccc agtttatgtg ctttgtcatg    540
ccggcgcttg ttgcatcgag gttctggggt gaggcgttct ggaacgcctt tgggtggcg    600
ggggctttga ggtatatgtt ggtgctgcac ttcacctgga tggttaacag tgcggcgcac    660
ttgtatggcg accaccgta cgaccctacc atgtggccgg cggagaaccc gttggtatcg    720
gtagtggcga tcggagaagg ctggcataac tggcaccatc gttacccta cgactacgcg    780
gcttccgagt ttgggatttc gcagcagttc aacccgacca aggcgttcat tgatttttt    840
gcggccatag ggatggtgac gaaccgaaaa cgtgcgacgg gggcttgggc aaagctcaag    900
gaatccaggg caagggatgc ggcgaatggg aagagcatga aagatttcaa gggaagaggc    960
tcggggtcag actatggtac gacaaacacc aattacgcgg tgtcgaacaa gacagtggtg   1020
accgacaagg gggcgcaaca accagggtgg gaggagagca atcaccccaa gtacaactaa   1080
```

<210> SEQ ID NO 49
<211> LENGTH: 452
<212> TYPE: PRT
<213> ORGANISM: Nannochloropsis gaditana

<400> SEQUENCE: 49

Met Gly Arg Gly Gly Glu Lys Thr Val Thr Pro Pro Ser Lys Ser Phe
1               5                   10                  15

His Ala His Gly His Ser Leu Thr Ala Ser Asp Leu Ser Arg Ala Asp
            20                  25                  30

Ala Ala Ser Thr Ile Ser Ser Val Arg Pro Ser Lys Ser Leu Glu
        35                  40                  45

Ala Met Pro Thr Glu Glu Leu Arg Lys Lys Ala Leu Gln Tyr Gly His
    50                  55                  60

Asp Ala Ser Ala Asp Arg Ala Ser Leu Leu Gln Ile Leu Ala Pro Tyr
65                  70                  75                  80

Gly Asp Ile Leu Leu Arg Thr Asp Ala Pro Pro Ser Leu Pro Leu Ala
                85                  90                  95

Pro Pro Pro Phe Thr Leu Ala Asp Ile Lys Ala Ala Val Pro Arg His
            100                 105                 110

Cys Phe Glu Arg Ser Leu Thr Thr Ser Phe Phe His Leu Ala Cys Asp
        115                 120                 125

Leu Val Leu Val Ala Leu Leu Gly Tyr Leu Ala Thr Leu Ile Gly His
    130                 135                 140

Pro Asp Val Pro Thr Met Ser Arg Tyr Leu Leu Trp Pro Leu Tyr Trp
145                 150                 155                 160

Tyr Ala Gln Gly Ser Val Leu Thr Gly Val Trp Val Ile Ala His Glu
                165                 170                 175

Cys Gly His Gln Ser Phe Ser Pro Tyr Glu Arg Val Asn Asn Leu Val
            180                 185                 190

```
Gly Trp Val Leu His Ser Ala Leu Leu Val Pro Tyr His Ser Trp Arg
            195                 200                 205

Ile Ser His Gly Lys His Asn Asn Thr Gly Ser Cys Glu Asn Asp
    210                 215                 220

Glu Val Phe Ala Pro Pro Ile Lys Glu Asp Leu Met Asp Glu Ile Leu
225                 230                 235                 240

Leu His Ser Pro Leu Ala Asn Leu Ala Gln Ile Ile Met Leu Thr
                245                 250                 255

Val Gly Trp Met Pro Gly Tyr Leu Leu Met Asn Ala Thr Gly Pro Arg
            260                 265                 270

Lys Tyr Lys Gly Lys Asn Asn Ser His Phe Asp Pro Asn Ser Ala Leu
    275                 280                 285

Phe Ser Pro Lys Asp Arg Leu Asp Ile Ile Trp Ser Asp Ile Gly Phe
290                 295                 300

Phe Leu Ala Leu Ala Gly Val Val Trp Ala Cys Thr Gln Tyr Gly Phe
305                 310                 315                 320

Ser Thr Val Gly Lys Tyr Tyr Leu Leu Pro Tyr Met Val Val Asn Tyr
            325                 330                 335

His Leu Val Leu Ile Thr Tyr Leu Gln His Thr Asp Val Phe Ile Pro
                340                 345                 350

His Phe Arg Gly Ala Glu Trp Ser Trp Phe Arg Gly Ala Leu Cys Thr
            355                 360                 365

Val Asp Arg Ser Phe Gly Trp Leu Leu Asp His Thr Phe His His Ile
    370                 375                 380

Ser Asp Thr His Val Cys His His Ile Phe Ser Lys Met Pro Phe Tyr
385                 390                 395                 400

His Ala Gln Glu Ala Ser Glu His Ile Lys Lys Ala Leu Gly Pro Tyr
                405                 410                 415

Tyr Leu Lys Asp Asp Thr Pro Ile Trp Lys Ala Leu Trp Arg Ser Tyr
            420                 425                 430

Thr Leu Cys Lys Tyr Val Asp Thr Asp Lys Asn Ala Val Phe Tyr Lys
    435                 440                 445

His Arg Ala Ser
    450

<210> SEQ ID NO 50
<211> LENGTH: 1359
<212> TYPE: DNA
<213> ORGANISM: Nannochloropsis gaditana

<400> SEQUENCE: 50
atggggcgtg gcggtgagaa aactgtcaca cctccatcaa atccttcca tgctcatggc    60 cactctctga ccgccagtga cctttctcga gcggatgccg catccactat ctcgagctcg   120
gttaggccca gtaagtcgtt ggaggcaatg cccacggaag aattgcgaaa gaaggcactg   180
caatacggac acgacgcctc cgcggacagg gcctcgttgc ttcaaatact ggccccatat   240
ggcgacattc ttcttcgtac ggacgcgcct ccctccctcc cctcgcccc tcctcccttc    300 acccttgcgg atatcaaagc cgccgtaccc aggcattgct cgaacgctc cttgaccacc    360 tccttcttcc acctcgcttg tgacctcgtc ctggttgctc tgctcggata cttggccacg   420
ctcatcgggc acccggacgt gccgaccatg tcccgctacc tactgtggcc tctctactgg   480
tacgcgcagg gctcggtgct gacaggcgtg tgggtcattg cccatgaatg tgggcatcag   540
tctttttccc cgtacgaacg ggtgaacaac ctggtggggt gggtcctgca ctccgccctc   600
```

```
ctcgtcccgt accattcctg gcgcatctcc cacggcaagc accacaacaa cacggggagc    660
tgcgagaacg acgaggtgtt cgcgccgcca atcaaggaag acctgatgga cgagatcctc    720
ctccactccc ccttggccaa cctcgcccaa atcatcatca tgttgaccgt gggatggatg    780
cccggctacc tgttgatgaa tgccacggga cctcgaaagt acaagggcaa gaacaacagc    840
cacttcgatc cgaattcggc gctgttctcc cccaaggacc gcttggatat catctggtcg    900
gacataggct tcttcctcgc tttggccggc gtggtgtggg cctgcaccca gtacgggttc    960
tccacggtgg gcaagtacta cctgctcccc tacatggtgg tgaactatca cctggtgctc   1020
atcacctatc tccagcacac ggacgtcttc atccctcatt ccgcggggc agagtggtca    1080
tggttccggg gggctctttg cactgtcgac cgctccttcg gctggctgct cgaccatacg   1140
ttccaccaca tctcggacac gcacgtctgc catcatatct ttagtaagat gcctttctat   1200
cacgcgcaag aagcgagtga gcacatcaag aaggcgctgg ggccgtacta cctgaaggac   1260
gacaccccga tatggaaagc gttgtggcga agttatacgc tttgcaagta tgtggacacg   1320
gataaaaatg ccgttttta caagcaccga gcatcatag                            1359
```

<210> SEQ ID NO 51
<211> LENGTH: 475
<212> TYPE: PRT
<213> ORGANISM: Nannochloropsis gaditana

<400> SEQUENCE: 51

```
Met Gly Arg Gly Gly Glu Arg Val Glu Thr Gln Glu Ser Ile Ala Thr
1               5                   10                  15

Tyr Ser Ala Ser Lys Ser Gly Asp Ile Arg Gln His Gly Gly Lys Ile
            20                  25                  30

Thr Trp Asp Glu Val Arg Gln His Lys Thr Pro Gln Asp Ala Trp Leu
        35                  40                  45

Val Tyr Arg Asn Lys Val Tyr Asp Val Ser Gly Trp Gln Asp His Pro
    50                  55                  60

Gly Gly Asn Val Ile Phe Thr His Ala Gly Gly Asp Cys Thr Asp Ile
65                  70                  75                  80

Phe Ala Ala Phe His Pro Leu Gly Ala Thr Ser Tyr Met Asp Pro Phe
                85                  90                  95

Tyr Ile Gly Glu Leu Val Pro Gly Ser Asp Lys Lys Pro Glu Ala Gln
            100                 105                 110

Ala Ser Phe Glu Arg Ala Tyr Arg Asp Leu Arg Gly Lys Leu Ile Thr
        115                 120                 125

Gly Gly Phe Phe Lys Ala Ser Pro Leu Tyr Tyr Val Trp Lys Val Val
    130                 135                 140

Ser Thr Val Ala Leu Ala Val Gly Ala Trp Met Leu Val Gly Trp Ser
145                 150                 155                 160

Gln Ala Leu Ser Ile Gln Met Leu Ser Ala Phe Ile Leu Ala Leu Phe
                165                 170                 175

Trp Gln Gln Cys Gly Trp Leu Ala His Asp Phe Leu His His Gln Val
            180                 185                 190

Phe Lys Glu Arg Ala Tyr Gly Asp Leu Ala Gly Ile Met Ile Gly Asn
        195                 200                 205

Val Phe Gln Gly Phe Ser Val Ala Trp Trp Lys Asn Lys His Asn Thr
    210                 215                 220

His His Ala Val Pro Asn Leu Val Glu Ser Ser Pro Asp Ala Gln Asp
225                 230                 235                 240
```

Gly Asp Pro Asp Ile Asp Thr Met Pro Ile Leu Ala Trp Ser Leu Lys
            245                 250                 255

Met Ala Asp Arg Ala Lys Glu Tyr Ser Trp Gly Pro Phe Phe Leu Arg
        260                 265                 270

His Gln Ala Phe Leu Tyr Phe Pro Ile Leu Leu Val Ala Arg Ile Ser
            275                 280                 285

Trp Leu Leu Gln Ser Phe Leu Phe Val Phe Glu His Val Pro Gly Ala
        290                 295                 300

Ser Leu Trp Ala Thr Lys Gly Ala Thr Thr Glu Arg Gln Ala Ile Lys
305                 310                 315                 320

Asn Val Gly Leu Glu Lys Ala Gly Leu Leu Tyr Tyr Leu Trp Tyr
                325                 330                 335

Gly Ala Leu Met Phe Cys Asn Met Ser Leu Thr Arg Val Leu Ile Tyr
            340                 345                 350

Phe Val Ala Ser Gln Met Met Cys Gly Phe Leu Leu Ala Leu Val Phe
        355                 360                 365

Gly Leu Gly His Asn Gly Met Ala Val Tyr Asp Ala Asp Ala Arg Pro
    370                 375                 380

Asp Phe Trp Lys Leu Gln Val Thr Thr Thr Arg Asn Val Thr Gly Gly
385                 390                 395                 400

Trp Leu Ile Gln Trp Phe Cys Gly Gly Leu Gly Tyr Gln Val Asp His
                405                 410                 415

His Leu Phe Pro Met Ile Pro Arg His Arg Leu Gly Gln Leu His Gly
            420                 425                 430

Leu Val Glu Ser Phe Cys Lys Glu His Gly Val Lys Tyr His Glu Thr
        435                 440                 445

Ser Met Trp Glu Gly Thr Arg Glu Val Leu Ala His Leu Ala Ser Val
    450                 455                 460

Thr Lys Glu Phe Val Thr Asp Phe Pro Ala Met
465                 470                 475

<210> SEQ ID NO 52
<211> LENGTH: 1428
<212> TYPE: DNA
<213> ORGANISM: Nannochloropsis gaditana

<400> SEQUENCE: 52
atgggacgcg gtggtgaaag agtggagacg caagagtcta tagctactta ctcggcaagc    60
aaaagtggtg acatcaggca gcatgggggt aaaattactt gggatgaggt gcgtcaacac   120
aagacccctc aagatgcgtg gctcgtctac cgcaacaaag tctacgacgt gtcaggctgg   180
caagatcatc ctggggggaa tgtcatcttt acgcatgcgg ggggtgactg tactgacatc   240
tttgcagcct ccaccccttt gggtgcgaca tcttacatgg atcccttcta cattggcgag   300
ctcgttcccg gctctgacaa aaagcccgag gcgcaagcca gcttcgagcg agcgtatcga   360
gacttgaggg ggaaactcat cacgggcggg ttcttcaagg cgagtccttt gtactatgtg   420
tggaaagtcg tgtccaccgt cgccctggcc gtgggtgcct ggatgctcgt cggctggtcc   480
caagccctgt cgattcagat gctctctgcc ttcatcctcg ccctcttctg gcagcagtgc   540
gggtggctgg cccatgactt cttgcaccat caagttttca aagagcgagc atacggcgat   600
ctcgcgggga tcatgatcgg caatgtattc cagggcttct cggtggcctg gtggaagaac   660
aagcacaaca ctcatcacgc cgtgcccaac cttgtcgagt cctctccaga cgcccaggac   720
ggtgatcccg acattgacac catgcccatc ctggcctggt ccctgaagat ggcggaccgc   780

```
gcaaaggaat actcgtgggg cccttctc tccggcatc aggctttcct ctactttccc    840
atcctccttg tcgcccgcat ctcctggctc ttgcaatcct tccttttgt cttcgaacac    900 gtccccggtg caagcttatg ggctacgaaa ggcgcaacga ccgagcgaca ggccataaag    960
aacgtgggac tagagaaagc ggggcttctc ctttactatt tgtggtacgg cgctctcatg   1020
ttctgcaaca tgtctcttac gcgggtcctg atctacttcg tggcttctca gatgatgtgc   1080
ggctttctct tggcccctcgt cttcggcctc ggccacaacg gcatggcggt ctacgacgcc   1140
gacgcccgcc cggacttctg gaaactgcaa gtgacgacca cgagaaatgt gacggggggc   1200
tggttgatac aatggttctg tggcggtctt ggctaccaag tagaccacca cctttttcca   1260
atgattccgc gccaccgtct tggtcagtta cacggtttgg tggaatcttt ctgcaaggag   1320
catggggtaa agtatcacga gacaagtatg tgggaaggga cacgggaggt gttggcccac   1380
ttggcgagcg tgacaaaaga attcgtaaca gatttcccag caatgtag                1428
```

<210> SEQ ID NO 53
<211> LENGTH: 407
<212> TYPE: PRT
<213> ORGANISM: Nannochloropsis gaditana

<400> SEQUENCE: 53

```
Met Val Glu Gln Thr Leu Pro Thr Leu Ser Gln Leu Lys Lys Ala Ile
1               5                   10                  15

Pro Glu Lys Cys Phe Gln Lys Ser Leu Leu Arg Ser Val Tyr Tyr Met
                20                  25                  30

Leu Arg Asp Phe Ala Ala Leu Ala Ala Leu Tyr Ile Ile Tyr Pro Ser
            35                  40                  45

Val Gln Ala Asn Phe Gly Leu Ala Gly Leu Phe Val Trp Trp Asn Leu
        50                  55                  60

Ala Gly Phe Phe Met Trp Cys Leu Phe Val Ile Gly His Asp Cys Gly
65                  70                  75                  80

His Gly Ser Phe Ser Glu Tyr Lys Trp Phe Asn Asp Val Cys Gly His
                85                  90                  95

Ile Cys His Ala Pro Leu Met Val Pro Tyr Trp Pro Trp Gln Lys Ser
                100                 105                 110

His Arg Leu His His Met Tyr His Asn His Leu Thr Lys Asp Met Ser
            115                 120                 125

His Pro Trp Met Thr Gln Glu Ile Phe Glu Asp Leu Thr Pro Phe Glu
        130                 135                 140

Gln Ala Leu Leu Glu Asn Pro Leu Ser Leu Phe Ile Lys Tyr Thr Phe
145                 150                 155                 160

Leu Tyr Leu Phe Ala Gly Lys Leu Asp Gly Ser His Val Leu Pro Thr
                165                 170                 175

Ser Pro Leu Phe Ser Asp Thr Lys Glu Arg Ile Gln Cys Ala Val Ser
                180                 185                 190

Thr Leu Cys Met Leu Val Ala Gly Val Leu Ile Tyr Val Gly Leu Glu
            195                 200                 205

Gly Gly Ala Glu Gly Gly Leu Ala Arg Ile Gly Ser Met Tyr Leu Ile
        210                 215                 220

Pro Leu Leu Val Phe Asn Ala Trp Ile Thr Met Val Thr Tyr Leu Gln
225                 230                 235                 240

His His Asp Glu Asp Thr Lys Val Tyr Ala Glu Gly Glu Trp Ser Tyr
                245                 250                 255

Ile Lys Gly Ala Leu Glu Thr Ile Asp Arg Glu Tyr Gly Met Gly Ile
```

```
        260                 265                 270
Asp Asp Leu Ser His Asn Ile Thr Asp Gly His Val Ala His His Leu
            275                 280                 285

Phe Phe Thr Gln Ile Pro His Tyr His Leu Lys Asp Ala Thr Ala Ala
            290                 295                 300

Val Arg Gln Leu Leu Thr Pro Thr Gly Thr Tyr Lys Lys Lys Gln Ser
305                 310                 315                 320

Trp Asn Phe Leu Gly Lys Phe Thr Glu Leu Asn Tyr Lys Leu Lys Tyr
                325                 330                 335

Val Ala Gly Gln Gly Val Leu Ser Tyr Val Asp Trp Glu Ala Ile Gln
            340                 345                 350

Lys Gly Ala Ser Pro Pro Val Cys Ser Thr Asp Ala Ser Pro Ala Thr
            355                 360                 365

Pro Ala Ala Pro Leu Pro Lys Val Ala Val Thr Cys Ala Thr Glu Pro
            370                 375                 380

Leu Ile Ala Leu Glu Ala Lys Gly Arg Ser Thr Arg Lys Arg Ser Pro
385                 390                 395                 400

Ala Arg Ser Ser Ser Pro Pro
                405
```

```
<210> SEQ ID NO 54
<211> LENGTH: 1224
<212> TYPE: DNA
<213> ORGANISM: Nannochloropsis gaditana

<400> SEQUENCE: 54
atggttgagc aaacgctacc gacactttct caattgaaga aagccattcc cgagaaatgc     60
ttccagaaat cacttctccg ctctgtgtac tacatgctgc gagactttgc cgccctggca    120
gctctgtata ttatataccc cagcgtgcag gctaattttg gccttgccgg actctttgtg    180
tggtggaacc tggcgggatt ttttatgtgg tgtctctttg tgatcggtca cgactgtggt    240
cacggctcct tctcggagta taagtggttc aacgacgtct gtggccatat ttgccacgcc    300
ccgctcatgg tgccctactg gccctggcag aagtcccatc gcctgcacca catgtaccac    360
aaccacctga cgaaagacat gtcacatcca tggatgacgc aagagatctt cgaggaccta    420
acaccgttcg agcaagcctt gctggagaac ccactctccc tcttcatcaa atacacattc    480
ctctacctct tcgcgggcaa actcgacggc agccacgtcc tgcccacctc ccccctcttc    540
agcgatacca aggagcgcat ccagtgcgcc gtctccaccc tctgcatgct cgtggccggg    600
gtcctcattt atgtgggcct tgaaggaggg gcggagggag ggctggctcg gatcggctcc    660
atgtatttga tcccgctgtt ggtgttcaac gcctggatca ccatggtcac gtacctgcag    720
catcacgacg aggacacgaa ggtgtacgcg gaggggagt ggagctacat caaggggcg    780 ctcgagacca tcgatcggga gtatgggatg ggcattgatg acctgtcgca caacatcacg    840
gacggccacg tcgcccacca cctcttcttc acccagatcc cgcactacca cctgaaggac    900
gctacggccg ccgtacggca gctcttgacg cccacgggca cctacaagaa gaagcaatcc    960
tggaattttc tgggaaaatt cactgagttg aactacaagt tgaagtatgt tgcgggacaa   1020
ggggtgctct cctacgtgga ctggaggct attcagaagg gtgcttcccc cccggtttgt   1080
tccaccgacg cctcccctgc cactcccgca gcgcccctac ctaaggtggc tgtcacctgc   1140
gcgacagaac cgttaatcgc ccttgaagcg aagggaagat caacccgaaa gcgctctccg   1200
gcacgctcct cttcacctcc gtag                                          1224
```

<210> SEQ ID NO 55
<211> LENGTH: 515
<212> TYPE: PRT
<213> ORGANISM: Nannochloropsis gaditana

<400> SEQUENCE: 55

Met Pro Pro Gln Asn Asp Ala Ala Leu Gly Ser Gly Leu Phe Arg Asn
1               5                   10                  15

Arg Phe Gly Arg Lys Ser Ser Ala Ser Ser Leu Leu Val Asn Asp Gly
            20                  25                  30

Ser Met Gly Ser Thr Glu Pro Val Leu Ser Thr Ala Ala Val Pro Ala
        35                  40                  45

Thr Glu Pro Ala Gly Lys Ser Tyr Thr Trp Gln Glu Val Ala Glu His
    50                  55                  60

Asn Thr Glu Lys Ser Leu Trp Val Thr Val Arg Gly Lys Val Tyr Asp
65                  70                  75                  80

Ile Ser Ser Trp Val Asp Asn His Pro Gly Gly Lys Glu Ile Leu Leu
                85                  90                  95

Leu Ala Ala Gly Arg Asp Ile Thr Tyr Ala Phe Asp Ser Tyr His Pro
            100                 105                 110

Phe Thr Glu Lys Pro Thr Gln Val Leu Asn Lys Phe Glu Ile Gly Arg
        115                 120                 125

Val Thr Ser Tyr Glu Phe Pro Gln Tyr Lys Ala Asp Thr Arg Gly Phe
    130                 135                 140

Tyr Lys Ala Leu Cys Thr Arg Val Asn Asp Tyr Phe Val Ala His Lys
145                 150                 155                 160

Leu Asn Pro Lys Asp Pro Ile Pro Gly Ile Trp Arg Met Cys Leu Val
                165                 170                 175

Ala Leu Val Ala Leu Ala Ser Phe Val Val Cys Asn Gly Tyr Val Gly
            180                 185                 190

Val Glu Gly Thr Trp Ala Gly Thr Thr Trp Ala Arg Leu Val Ala Ala
        195                 200                 205

Val Val Phe Gly Ile Cys Gln Ala Leu Pro Leu Leu His Val Met His
    210                 215                 220

Asp Ser Ser His Leu Ala Phe Gly Asn Thr Glu Arg Trp Trp Gln Val
225                 230                 235                 240

Gly Gly Arg Leu Ala Met Asp Phe Phe Ala Gly Ala Asn Met Thr Ser
                245                 250                 255

Trp His Asn Gln His Val Ile Gly His His Ile Tyr Thr Asn Val Phe
            260                 265                 270

Leu Ala Asp Pro Asp Leu Pro Asp Lys Ala Ala Gly Asp Pro Arg Arg
        275                 280                 285

Leu Val Gln Lys Gln Ala Trp Gln Ala Met Tyr Lys Trp Gln His Leu
    290                 295                 300

Tyr Leu Pro Pro Leu Tyr Gly Ile Leu Gly Ile Lys Phe Arg Val Gln
305                 310                 315                 320

Asp Ile Met Glu Thr Phe Gly Ser Gly Thr Asn Gly Pro Val Arg Val
                325                 330                 335

Asn Pro Leu Ser Phe Phe Gln Ala Glu Met Ile Phe Thr Lys Met
        340                 345                 350

Phe Trp Ala Gly Trp Arg Ile Ala Phe Pro Leu Leu Ser Pro Ser Phe
    355                 360                 365

His Thr Gly Trp Ala Ala Phe Ser Ala Leu Phe Leu Val Ser Glu Phe
370                 375                 380

```
Met Thr Gly Tyr Phe Leu Ala Phe Asn Phe Gln Val Ser His Val Ser
385                 390                 395                 400

Ser Glu Cys Asp Tyr Pro Leu Gly Glu Ala Pro Arg Glu Gly Glu Asp
            405                 410                 415

Gly Asn Ile Val Asp Glu Trp Ala Val Ser Gln Ile Lys Ser Ser Val
            420                 425                 430

Asp Tyr Ala His Asn Asn Pro Val Thr Thr Phe Leu Cys Gly Ala Leu
            435                 440                 445

Asn Tyr Gln Val Thr His His Leu Phe Pro Thr Val Ser Gln Tyr His
            450                 455                 460

Tyr Pro Ala Ile Ala Pro Ile Ile Gln Asp Val Cys Arg Glu Phe Asn
465                 470                 475                 480

Val Asp Tyr Lys Val Leu Pro Asp Phe Val Thr Ala Phe His Ala His
                485                 490                 495

Ile Ala His Leu Lys Thr Leu Gly Glu Arg Gly Glu Ala Ala Glu Val
            500                 505                 510

His Met Gly
        515

<210> SEQ ID NO 56
<211> LENGTH: 1548
<212> TYPE: DNA
<213> ORGANISM: Nannochloropsis gaditana

<400> SEQUENCE: 56
atgcctccgc agaacgacgc tgccctcgga agtggtctct tcggaaccg cttcggtcgc      60 aaaagctccg cttcttccct tcttgtcaat gacggcagta tgggaagcac cgagcctgtc     120 cttccacgg cggccgtacc ggcaacgag ccggcgggga atcctacac atggcaagaa       180 gtagccgagc acaacacaga gaaaagtttg tgggtcactg tgcgagggaa ggtgtacgac     240
atatccagtt gggtggacaa ccatccgggg ggcaaggaga tcctgctgtt ggcggcgggg    300
agggacatca cgtacgcctt cgattcctac cacccgttca cggagaaacc gacgcaggtg    360
ctcaacaagt tgagatcgg ccgggtcacc tcctacgaat cccccagta caaggcggac     420 actcgtggtt tctacaaggc cctgtgcacc cgcgtgaatg actactttgt ggcccacaag   480
ctcaacccta aggacccaat ccccggcatc tggcgcatgt gcctcgtcgc cctggtggcc   540
ttggcctctt tcgtggtctg caacggctac gtgggtgtgg aagggacatg ggccgggact  600
acgtgggccc ggctagtggc ggcggtggtg tttgggatct gtcaggccct tccttttgttg 660 cacgtcatgc acgactcctc ccacctggcg tttggcaata cagaacgctg gtggcaggtg   720
gggggggcgc tggcgatgga tttcttcgcc ggggcgaaca tgaccagctg gcacaaccaa   780
cacgtgatcg gccaccatat ctacacgaat gtcttcctcg ccgacccgga tttacccgac   840
aaagccgcgg gagatccgag aagattggtg cagaaacagg cgtggcaagc catgtataaa   900
tggcagcact tgtaccttcc ccctctgtac ggcatcctgg ggatcaaatt cgagtccaa    960 gatatcatgg agaccttcgg aagtggcacg aacgggcccg tacgggtgaa ccccttgtcc  1020
tttttccaat gggccgagat gattttcacc aaaaatgtttt gggcaggatg gaggatcgcg 1080
ttccccttgc tctccccgtc tttccacacc ggctgggctg cttttccgc cctcttcctg    1140 gtcagcgagt ttatgaccgg gtacttcctc gcctttaatt ccaagtctc ccacgtctcc    1200 tccgaatgcg actaccccct gggcgaagcc ccccgagagg gagaggatgg caacatcgtg  1260
gacgaatggg cggtctccca aataaagagc agtgtggact atgcgcacaa caacccagta   1320
```

-continued

```
accaccttcc tctgcggcgc cctgaactac caagtcactc accatctgtt ccccactgtg    1380
agtcaatacc actacccagc catcgcgccc atcatccaag acgtgtgtcg ggagttcaat    1440
gtggattaca aggttctgcc ggattttgtg acggctttcc acgcccacat agcgcatctg    1500
aagacgttgg gggagcgggg ggaggcagca gaagttcaca tgggctaa                1548
```

<210> SEQ ID NO 57
<211> LENGTH: 340
<212> TYPE: PRT
<213> ORGANISM: Nannochloropsis gaditana

<400> SEQUENCE: 57

```
Met Val Phe Gln Leu Ala Arg Asp Ala Leu Ser Ala Leu Val Tyr His
1               5                   10                  15

Tyr Lys Glu Gly Asn Leu Asn Trp Pro Met Ile Ile Tyr Leu Val Leu
            20                  25                  30

Ala His Leu Ala Ala Tyr Met Gly Leu Val Ser Ile Pro Ser Cys Lys
        35                  40                  45

Trp Gln Thr Leu Leu Glu Ala Phe Ile Leu Trp Pro Ile Thr Gly Leu
    50                  55                  60

Gly Ile Thr Ala Gly Val His Arg Leu Trp Ala His Arg Ser Tyr Thr
65                  70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
    130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Arg Tyr Phe Trp Gly Glu Ala
            180                 185                 190

Phe Trp Asn Ala Phe Trp Val Ala Gly Gly Leu Arg Tyr Cys Leu Val
        195                 200                 205

Leu His Phe Thr Trp Met Val Asn Ser Ala Ala His Leu Tyr Gly Asp
    210                 215                 220

His Pro Tyr Asp Pro Thr Ile Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Arg Gln Phe Asn Pro
            260                 265                 270

Thr Lys Ala Phe Ile Asp Phe Phe Ala Ala Ile Gly Met Val Ser Asn
        275                 280                 285

Arg Lys Arg Ala Thr Gly Ala Trp Ala Lys Leu Arg Glu Ser Arg Ala
    290                 295                 300

Lys Asp Glu Ala Asn Gly Lys Ser Ile Lys Asp Phe Arg Gly Arg Gly
305                 310                 315                 320

Val Val Gln Gly Thr Ala Gln Pro Pro Gly Trp Glu Gln Ser Ala His
                325                 330                 335
```

Pro Lys Tyr Asn
            340

<210> SEQ ID NO 58
<211> LENGTH: 1023
<212> TYPE: DNA
<213> ORGANISM: Nannochloropsis gaditana

<400> SEQUENCE: 58

```
atggtcttcc agttggctcg cgatgccttg tcggcgcttg tctaccacta caaagagggc     60
aacctgaatt ggcccatgat catctaccta gtcctcgcgc accttgccgc ctacatgggg    120
ctggtctcca tcccttcatg caagtggcag acccttctgg aggccttcat cctgtggccc    180
atcaccgggt tgggcatcac ggccggcgtc atcgtctgt gggcgcatcg ctcctacact     240
gccaccttgc cgtaccgcat cctcctcatg ctcttcaatt cgattgcgaa tcaaggcagc    300
atctaccact ggtcccggga tcatcgcgtt caccacaagt actcggagac agatgcggat    360
cctcacaatg ccaccgtgg cttcttcttc gcgcacatgg ggtggcttat cgttaagaaa     420
cacccgaagg tagtagaagg cggcaaacag ttggatttct ctgatcttgc tgcggacccg    480
gtggtccgtt ccagcgtga ctgggacccg tggttcgcgc aattcatgtg cttcgtcatg     540
ccggcgctgg tcgccagata tttctggggt gaggcctttt ggaacgcatt ttgggttgca    600
gggggcctcc gctactgtct ggtcctgcat ttcacctgga tggtgaactc cgccgcccac    660
ttatacggcg atcaccccta cgaccccacc atctggcccg ccgagaaccc gctagtatcg    720
gtggtggcca tcggggaggg atggcacaat tggcatcacc ggtatcccta cgactatgcg    780
gcatctgagt tcgggatctc ccgacaattt aaccctacga aggctttcat tgacttcttt    840
gctgccatcg gtatggtctc gaatcgaaag cgggcgacag gggcctgggc caagctcagg    900
gagtcacggg cgaaggacga ggcgaacggg aagagcatca agattttcg aggacgagga    960
gttgtccaag caccgcaca gccaccggga tgggaacaaa gcgcgcaccc caagtacaac    1020
tga                                                                 1023
```

<210> SEQ ID NO 59
<211> LENGTH: 274
<212> TYPE: PRT
<213> ORGANISM: Nannochloropsis gaditana

<400> SEQUENCE: 59

Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

```
Phe Leu Gln Tyr His Leu Ile His Glu Thr Leu Arg Gly Lys Glu Lys
            130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
                180                 185                 190

Phe Phe Ala Ala Asn Lys Gly Asn Gly Phe Thr Ala Asn Leu Thr Ile
                195                 200                 205

Asn Tyr Lys Arg Pro Ile Ile Cys Gly Thr Glu Ile Lys Val Leu Ala
            210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
                260                 265                 270

Ile Ser

<210> SEQ ID NO 60
<211> LENGTH: 287
<212> TYPE: PRT
<213> ORGANISM: Nannochloropsis oculata

<400> SEQUENCE: 60

Met Thr Pro Leu Ala Phe Thr Val Leu Gly Lys Leu Gly Gly Thr Leu
1               5                   10                  15

Thr Phe Ala Cys Val Arg Arg Leu Tyr His Leu Leu Arg Arg Ala
                20                  25                  30

Thr Leu Ser Ser His Tyr Gln Val Thr Arg Pro Tyr Gly His Ser Asn
            35                  40                  45

Ser Gly Cys Ser His Ser Thr Thr Leu Arg Thr Ser Phe Pro Val
        50                  55                  60

Leu Phe Ala Gln Leu Ala Ala Thr Ala Ala Val Val Ala Ala Ile
65                  70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
                100                 105                 110

Glu Ala Thr Ser Ser Ala Thr Cys Asn Pro Ser Leu Phe Glu His His
            115                 120                 125

Asp Arg Val Asp Thr Lys Leu His Arg Ala Tyr Pro Glu Phe Leu Lys
            130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
            195                 200                 205

Ala Lys Arg Gly Asn Gly Phe Thr Ala Asn Leu Thr Ile Asn Tyr Lys
        210                 215                 220
```

```
Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
            245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
            275                 280                 285

<210> SEQ ID NO 61
<211> LENGTH: 285
<212> TYPE: PRT
<213> ORGANISM: Nannochloropsis granulata

<400> SEQUENCE: 61

Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
                20                  25                  30

Ala Ser Ser Ser Gln Val Thr Arg Pro Tyr Ser His Ser Thr Ala Asn
            35                  40                  45

Ser Thr His Ser Thr Thr Thr Leu Ser Asn Ser Phe Pro Val Leu Phe
        50                  55                  60

Ala Gln Leu Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285

<210> SEQ ID NO 62
<211> LENGTH: 35
<212> TYPE: DNA
```

<210> SEQ ID NO 63
<211> LENGTH: 38
<212> TYPE: DNA
<213> ORGANISM: Artificial Sequence
<220> FEATURE:
<223> OTHER INFORMATION: Primer No. 62

<400> SEQUENCE: 62
cagcccgcat caacaatggt cttccagctc gcccg                            35

<210> SEQ ID NO 63
<211> LENGTH: 38
<212> TYPE: DNA
<213> ORGANISM: Artificial Sequence
<220> FEATURE:
<223> OTHER INFORMATION: Primer No. 63

<400> SEQUENCE: 63
ctcttccaca gaagcttagt tgtacttggg gtgattgc                         38

<210> SEQ ID NO 64
<211> LENGTH: 35
<212> TYPE: DNA
<213> ORGANISM: Artificial Sequence
<220> FEATURE:
<223> OTHER INFORMATION: Primer No. 64

<400> SEQUENCE: 64
cagcccgcat caacaatggg acgcggcggt gagaa                            35

<210> SEQ ID NO 65
<211> LENGTH: 35
<212> TYPE: DNA
<213> ORGANISM: Artificial Sequence
<220> FEATURE:
<223> OTHER INFORMATION: Primer No. 65

<400> SEQUENCE: 65
ctcttccaca gaagcctatg cccgctgctt gtaga                            35

<210> SEQ ID NO 66
<211> LENGTH: 35
<212> TYPE: DNA
<213> ORGANISM: Artificial Sequence
<220> FEATURE:
<223> OTHER INFORMATION: Primer No. 66

<400> SEQUENCE: 66
cagcccgcat caacaatggg acgcggtggc gagcg                            35

<210> SEQ ID NO 67
<211> LENGTH: 35
<212> TYPE: DNA
<213> ORGANISM: Artificial Sequence
<220> FEATURE:
<223> OTHER INFORMATION: Primer No. 67

<400> SEQUENCE: 67
ctcttccaca gaagcttaca tggcggggaa atcgg                            35

<210> SEQ ID NO 68
<211> LENGTH: 35
<212> TYPE: DNA
<213> ORGANISM: Artificial Sequence
<220> FEATURE:
<223> OTHER INFORMATION: Primer No. 68

<400> SEQUENCE: 68
cagcccgcat caacaatggt tgagcaaacg ttacc                            35

<210> SEQ ID NO 69
<211> LENGTH: 35
<212> TYPE: DNA
<213> ORGANISM: Artificial Sequence
<220> FEATURE:
<223> OTHER INFORMATION: Primer No. 69

<400> SEQUENCE: 69
ctcttccaca gaagcttacg gaggggagga tgaac         35

<210> SEQ ID NO 70
<211> LENGTH: 822
<212> TYPE: DNA
<213> ORGANISM: Artificial Sequence
<220> FEATURE:
<223> OTHER INFORMATION: Paromomycin resistance gene

<400> SEQUENCE: 70
atggtcgaga ttcgaagcat ggacgatgcg ttgcgtgcac tgcggggtcg gtatcccggt    60
tgtgagtggg ttgttgtgga ggatggggcc tcggggctg gtgtttatcg cttcggggt    120 ggtgggcggg agttgtttgt caaggtggca gctctggggg ccggggtggg cttgttgggt   180
gaggctgaac ggctggtgtg gttggcggag gtggggattc ccgtacctcg tgttgtggag   240
ggtggtgggg acgagagggt cgcctggttg gtcaccgaag cggttccggg gcgtccggcc   300
agtgcgcggt ggccgcggga gcagcggctg gacgtggcgg tggcgctcgc ggggctcgct   360
cgttcgctgc acgcgctgga ctgggagcgg tgtccgttcg atcgcagtct cgcggtgacg   420
gtgccgcagg cggcccgtgc tgtcgctgaa gggagcgtcg acttggagga tctggacgag   480
gagcggaagg ggtggtcggg ggagcggctt ctcgccgagc tggagcggac tcggcctgcg   540
gacgaggatc tggcggtttg ccacggtgac ctgtgcccgg acaacgtgct gctcgaccct   600
cgtacctgcg aggtgaccgg gctgatcgac gtggggcggg tcggccgtgc ggaccggcac   660
tccgatctcg cgctggtgct gcgcgagctg gcccacgagg aggacccgtg gttcgggccg   720
gagtgttccg cggcgttcct gcgggagtac gggcgcgggt gggatggggc ggtatcggag   780
gaaaagctgg cgttttaccg gctgttggac gagttcttct ga                      822

<210> SEQ ID NO 71
<211> LENGTH: 35
<212> TYPE: DNA
<213> ORGANISM: Artificial Sequence
<220> FEATURE:
<223> OTHER INFORMATION: Primer No. 71

<400> SEQUENCE: 71
cttttttgtg aagcaatggt cgagattcga agcat         35

<210> SEQ ID NO 72
<211> LENGTH: 35
<212> TYPE: DNA
<213> ORGANISM: Artificial Sequence
<220> FEATURE:
<223> OTHER INFORMATION: Primer No. 72

<400> SEQUENCE: 72
tttcccccat cccgatcaga agaactcgtc aaca         35

<210> SEQ ID NO 73
<211> LENGTH: 28
<212> TYPE: DNA

```
<213> ORGANISM: Artificial Sequence
<220> FEATURE:
<223> OTHER INFORMATION: Primer No. 73

<400> SEQUENCE: 73
tgcttcacaa aaaagacagc ttcttgat                                          28

<210> SEQ ID NO 74
<211> LENGTH: 25
<212> TYPE: DNA
<213> ORGANISM: Artificial Sequence
<220> FEATURE:
<223> OTHER INFORMATION: Primer No. 74

<400> SEQUENCE: 74
tcgggatggg ggaaaaaaac ctctg                                             25

<210> SEQ ID NO 75
<211> LENGTH: 40
<212> TYPE: DNA
<213> ORGANISM: Artificial Sequence
<220> FEATURE:
<223> OTHER INFORMATION: Primer No. 75

<400> SEQUENCE: 75
cgagctcggt acccggtgtg tcctgcgtgt tgatcagtag                             40

<210> SEQ ID NO 76
<211> LENGTH: 29
<212> TYPE: DNA
<213> ORGANISM: Artificial Sequence
<220> FEATURE:
<223> OTHER INFORMATION: Primer No. 76

<400> SEQUENCE: 76 tttttaggggg tggtcgagtt gctgtggtg                                        29

<210> SEQ ID NO 77
<211> LENGTH: 24
<212> TYPE: DNA
<213> ORGANISM: Artificial Sequence
<220> FEATURE:
<223> OTHER INFORMATION: Primer No. 77

<400> SEQUENCE: 77
gaaagatcca agagagacga gtag                                              24

<210> SEQ ID NO 78
<211> LENGTH: 30
<212> TYPE: DNA
<213> ORGANISM: Artificial Sequence
<220> FEATURE:
<223> OTHER INFORMATION: Primer No. 78

<400> SEQUENCE: 78
aggaccgaat cgaggctctg ataaatgagg                                        30

<210> SEQ ID NO 79
<211> LENGTH: 1000
<212> TYPE: DNA
<213> ORGANISM: Nannochloropsis oculata

<400> SEQUENCE: 79
gtgtgtcctg cgtgttgatc agtagatgcg caagataccg tcagttagcc agtcgcgtgt       60
gatacactca tcacgaattg aaaaaaaagg gggagggagg aaacgaaggg ccaattgctt      120
```

```
acctggccgt gtgcttcatg tgtaaaacaa atacagtat  ggcttcttgt caacctgtcc      180
cccggcactt ccagcttgcc tgccaaggta ctaggcatat ttggtttcgt agaagtagag      240
tcttcatata tgaatgctgt cccggacctt ctcaagggct gcagctcgtt ggcgattggt      300
gaatctatgc ccaattcatc cgactctttg tcgggttccg agaggaggac ttgtcatgaa      360
agagataggg gctttggtct tgcacacgcc cgcgttccag ctttccccccc gcaacctcgc     420 gcgtcgacca tgcgttgttg cctttgcatg acgcgcggtc ataatctact gtagatgctg      480 gcgaccttt  cctttttttt catctttgaa cacaacagat atacgctgag gcgtcgggaa      540
agcgcaaaat accgcgcgct gttgacgtcc gcttatttg  ttggcccgcc ccgcgctctt      600
ccttgtgcct tcgcaggtcc atctgtggat tcgcgtccca agaccaagca ccattgtctt      660
tcatagctgc catgcatggt tgtggcacgc caggggaggc gaatcccata gccaccaaac      720
ctcgtggctg tgccgagtgc cgtgcacccc aaggagtatc cttgcactca tgcggcctgc      780
gttgccttcg tgctcatgcc cccatgagac gcgcaaaggc agcaaagacc tgagctagcg      840
gaatctttga tttcacaagg catgtaaaat gtatcaaggt cctgggcgca gggcttttgc      900
ctcacgcagc aacacattcc aatcctatct cacatgtcca atccttcatt catcacctcc      960
ggccctccgc acaccacagc aactcgacca cccctaaaa                            1000

<210> SEQ ID NO 80
<211> LENGTH: 938
<212> TYPE: DNA
<213> ORGANISM: Nannochloropsis oculata

<400> SEQUENCE: 80
gaaagatcca agagagacga gtagagattt tttttttggg attgatgttt gtcgttcttt       60
gagttgtcgt cgagttacgc cttttgtaag aatgttccgc aggagaggag gaggatgggc      120
atgagtgagg gtgagagggc ttgcccgctt ttttttttaa aaacgctgaa gacgtggttg      180
tcaaacaaac cccccataga aacgattttg ttacggtgcg gtccagacgt cacttgaatg      240
gctccgcgga aaggccaggg agggaagggg ggagggagga acatgaaaac atgttgaacg      300
gctcaacagg gtttggggga caagagaggt agcgccctga tggactgctc cctcccctcc      360
tttccctcaa tgtctcattc atccatgctt ccccttctc  tctctcccct ccgttccatc      420
ccccgcgggc gtggtagtgg cgtgatggga tccactaaaa tgtacgtgta agaaaagccg      480
gtgagcttac gcttttgtga agtgggagt  acgagtgttg tgtgtgtgtg tagtggtttc      540
agaccccaga cagaggcgaa gcagaaaaag cagacgatga agacgacgaa gaaatgagca      600
gtctattttt atcgtggaaa cagaagaggt gatatcgtct cgttctttgt tatcacctac      660
cccgcgtgca tgtacatgca gccttttat  tttgtaatct ttcccgaaaa atcaaccgcc      720 acctccccccc gccttctct  cacccatcat cttctcctgt ttatcttcta ctttacacta      780
gatcgcatgg cacatctccc tcgcaatcca tcggtgcaac catcatcgat cccactcctc      840
cctccctccc tccctccctc ctcccctctc ttctaagaaa tccgctagct gcgaacccag      900
ctcacctacc tcatttatca gagcctcgat tcggtcct                             938

<210> SEQ ID NO 81
<211> LENGTH: 39
<212> TYPE: DNA
<213> ORGANISM: Artificial Sequence
<220> FEATURE:
<223> OTHER INFORMATION: Primer No. 81
```

<400> SEQUENCE: 81
cctcgattcg gtcctttctt ccgcttgttg ctgccgatg    39

<210> SEQ ID NO 82
<211> LENGTH: 37
<212> TYPE: DNA
<213> ORGANISM: Artificial Sequence
<220> FEATURE:
<223> OTHER INFORMATION: Primer No. 82

<400> SEQUENCE: 82
gaccaccccc taaaaatggt cttccagctc gcccgag    37

<210> SEQ ID NO 83
<211> LENGTH: 38
<212> TYPE: DNA
<213> ORGANISM: Artificial Sequence
<220> FEATURE:
<223> OTHER INFORMATION: Primer No. 83

<400> SEQUENCE: 83
tctcttggat ctttcttagt tgtacttggg gtgattgc    38

<210> SEQ ID NO 84
<211> LENGTH: 38
<212> TYPE: DNA
<213> ORGANISM: Artificial Sequence
<220> FEATURE:
<223> OTHER INFORMATION: Primer No. 84

<400> SEQUENCE: 84
gaccaccccc taaaaatggt tgagcaaacg ttaccgac    38

<210> SEQ ID NO 85
<211> LENGTH: 37
<212> TYPE: DNA
<213> ORGANISM: Artificial Sequence
<220> FEATURE:
<223> OTHER INFORMATION: Primer No. 85

<400> SEQUENCE: 85
tctcttggat ctttcttacg gaggggagga tgaacgg    37

<210> SEQ ID NO 86
<211> LENGTH: 39
<212> TYPE: DNA
<213> ORGANISM: Artificial Sequence
<220> FEATURE:
<223> OTHER INFORMATION: Primer No. 86

<400> SEQUENCE: 86
gaccaccccc taaaaatggg acgcggtggc gagcgggtc    39

<210> SEQ ID NO 87
<211> LENGTH: 39
<212> TYPE: DNA
<213> ORGANISM: Artificial Sequence
<220> FEATURE:
<223> OTHER INFORMATION: Primer No. 87

<400> SEQUENCE: 87
tctcttggat ctttcttaca tggcggggaa atcggccac    39

<210> SEQ ID NO 88
<211> LENGTH: 34

-continued

```
<212> TYPE: DNA
<213> ORGANISM: Artificial Sequence
<220> FEATURE:
<223> OTHER INFORMATION: Primer No. 88

<400> SEQUENCE: 88
gtgtgtcctg cgtgttgatc agtagatgcg caag                          34
```

METHOD OF PRODUCING LIPID

TECHNICAL FIELD

The present invention relates to a method of producing lipids. Further, the present invention also relates to a transformant for use in this method.

BACKGROUND ART

Fatty acids are one of the principal components of lipids. In vivo, fatty acids are bonded to glycerin via an ester bond to form lipids such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents, disinfectants, or the like. Cationic surfactants such as alkylamine salts and mono- or dialkyl-quaternary amine salts, as other higher alcohol derivatives, are commonly used for fiber treatment agents, hair conditioning agents, disinfectants, or the like. Further, benzalkonium type quaternary ammonium salts are commonly used for disinfectants, antiseptics, or the like. Furthermore, fats and oils derived from plants are also used as raw materials of biodiesel fuels.

Further, long-chain fatty acids having 18 or more carbon atoms are different in chemical properties depending on a degree of unsaturation, and used in various applications. For example, most of polyunsaturated fatty acids (hereinafter, also referred to as "PUFA"), such as an eicosapentaenoic acid, are known to be essential fatty acids which are unable to be synthesized in vivo in animals. Accordingly, PUFA is particularly useful in nutritional use and utilized as physiologically functional food and the like. As mentioned above, fatty acids are widely used in various applications. Therefore, attempts have been made on improving productivity of the fatty acids or the lipids in vivo by using plants and the like. Furthermore, applications and usefulness of the fatty acids depend on the number of carbon atoms (chain length) or unsaturated bonds (degree of unsaturation) thereof. Therefore attempts have been made also on controlling the number of carbon atoms or unsaturated bonds of the fatty acids.

In recent years, researches and developments on renewable energy have been promoted toward realization of a sustainable society. In particular, photosynthetic microorganisms are expected as biofuel organisms without competing with grain in addition to an effect on reducing carbon dioxide.

Especially recently, algae attract attention due to its usefulness in biofuel production. The algae can produce lipids that can be used as the biodiesel fuels through photosynthesis. Further, the microalgae in the algae attract attention as next-generation biomass resources, because the microalgae do not compete with foods. Moreover, it is also reported that the algae have higher lipid productivity and lipid accumulation ability in comparison with plants. Research has started on a lipid synthesis and accumulation mechanism of the algae and lipid production technologies utilizing the mechanism, but unclear parts remain in many respects.

Generally, a fatty acid synthetic pathway of plants is localized in the chloroplast. In the chloroplast, an elongation reaction of the carbon chain is repeated starting from an acetyl-acyl-carrier-protein (hereinafter, also referred to as "ACP"), and finally a fatty acid having about 18 carbon atoms is synthesized. In this synthetic pathway of the fatty acids, the ACP functions as a carrier of the fatty acids.

So far, methods of utilizing the ACP for control of the number of carbon atoms (chain length) of the fatty acids have been proposed in a biosynthesis of the fatty acids. For example, Non-Patent Literature 1 describes a method for improving productivity of unsaturated fatty acids having 18 carbon atoms by overexpressing a gene encoding the ACP derived from an olive, which is introduced into a chloroplast genome or a nuclear genome of tobacco. Moreover, Non-Patent Literature 2 describes a method for improving productivity of α-linolenic acid, which is one kind of the unsaturated fatty acids having 18 carbon atoms, by overexpressing, in *Arabidopsis*, a gene encoding the ACP derived from *Arabidopsis*.

CITATION LIST

Non-Patent Literatures

Non-Patent Literature 1: Transgenic Research, 2016, vol. 25(1), p. 45-61

Non-Patent Literature 2: Plant Physiol., 2001, vol. 127(1), p. 222-229

SUMMARY OF INVENTION

The present invention relates to a method of producing lipids, containing the steps of:

culturing a transformant into which a gene encoding at least one of the proteins selected from the group consisting of the following proteins (A) to (C) is introduced; and producing fatty acids or lipids containing the same as components:

(A) a protein consisting of the amino acid sequence of the $23^{rd}$ to $146^{th}$ amino acids set forth in SEQ ID NO: 1;

(B) a protein consisting of an amino acid sequence having 70% or more identity with the amino acid sequence of the protein (A), and having acyl carrier protein activity; and (C) a protein containing the amino acid sequence of the protein (A) or (B), and having acyl carrier protein activity.

Further, the present invention relates to a method of producing lipids, containing the steps of: culturing a transformant into which a gene encoding at least one of the proteins selected from the group consisting of the proteins (A) to (C) is introduced; and improving the productivity of long-chain fatty acids or lipids containing the same as components, produced in a cell of the transformant.

Further, the present invention relates to a method of modifying fatty acid composition, containing the steps of: culturing a transformant into which a gene encoding at least one of the proteins selected from the group consisting of the proteins (A) to (C) is introduced; and increasing the proportion of long-chain fatty acids in whole fatty acids produced in a cell of the transformant.

Further, the present invention relates to the proteins (A) to (C).

Further, the present invention relates to a gene encoding any one of the proteins (A) to (C).

Furthermore, the present invention relates to a transformant containing a gene encoding any one of the proteins (A) to (C).

Other and further features and advantages of the invention will appear more fully from the following description.

MODE FOR CARRYING OUT THE INVENTION

The present invention relates to providing a method of producing lipids, which improves productivity of long-chain fatty acids or lipids containing the same as components.

Further, the present invention relates to providing a transformant in which the productivity of long-chain fatty acids or lipids containing the same as components is improved.

The present inventor diligently conducted study on the aforesaid points.

Firstly, the present inventor newly identified an ACP, as enzymes involved in fatty acid synthesis, from the algae of the genus *Nannochloropsis* being one kind of algae. Then, the present inventor found that the productivity of long-chain fatty acids or lipids containing the same as components to be produced is significantly improved by enhancing expression of a gene encoding the newly identified ACP.

The present invention was completed based on these findings.

According to the method of producing the lipids of the present invention, the productivity of long-chain fatty acids or lipids containing the same as components can be improved.

Moreover, the transformant of the present invention is excellent in the productivity of long-chain fatty acids or lipids containing the same as components.

The term "lipid(s)" in the present specification, covers a simple lipid such as a neutral lipid (monoacylglycerol (MAG), diacylglycerol (DAG), triacylglycerol (TAG), or the like), wax, and a ceramide; a complex lipid such as a phospholipid, a glycolipid, and a sulfolipid; and a derived lipid obtained from the lipid such as a fatty acid (free fatty acid), alcohols, and hydrocarbons.

The fatty acids categorized into the derived lipid generally refer to the fatty acids per se and mean "free fatty acids". In the present invention, the fatty acid group or the acyl group in molecules of a simple lipid and a complex lipid is expressed as "fatty acid residue". Then, unless otherwise specified, a term "fatty acid" is used as a generic term for "free fatty acid" and "fatty acid residue".

Moreover, a term "fatty acids or lipids containing the same as components" in the present specification is generically used including "free fatty acids" and "lipids having the fatty acid residues". Further, a term "fatty acid composition" in the present specification means a weight proportion of each fatty acid relative to the weight of whole fatty acids (total fatty acids) obtained by totaling the free fatty acids and the fatty acid residues described above regarding as fatty acids. The weight (production amount) of the fatty acids or the fatty acid composition can be measured according to the method used in Examples.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in the present specification, the "stringent conditions" includes, for example, the method described in Molecular Cloning—A LABORATORY MANUAL THIRD EDITION [Joseph Sambrook and David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH 7.0), 0.5% SDS, 5×Denhardt's solution and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

As described above, the present inventor newly identified the protein consisting of the amino acid sequence set forth in SEQ ID NO: 1 as the ACP, from an alga of the genus *Nannochloropsis*. The protein consisting of the amino acid sequence set forth in SEQ ID NO: 1 is a protein derived from *Nannochloropsis oculata* strain NIES-2145 being algae belonged to the genus *Nannochloropsis*. The ACP functions as a scaffold (carrier) of a biosynthetic reaction of the fatty acids (elongation reaction of the fatty acids). The acyl group of the fatty acids forms a thioester bond with a phosphopantetheine group bonded to a serine residue of the ACP. The fatty acids are elongated in this state.

However, as shown in Examples mentioned later, in the algae belonging to the genus *Nannochloropsis*, no change of the productivity of the long-chain fatty acids was able to be confirmed by only reinforcing expression of the protein consisting of the amino acid sequence set forth in SEQ ID NO: 1.

Accordingly, the present inventor conducted study on the localization site of the newly identified ACP by utilizing a subcellular localization prediction site TargetP (http://www.cbs.dtu.dk/services/TargetP/). As a result, it was estimated that the amino acid sequence set forth in SEQ ID NO: 1 includes a mitochondrial localization signal, and the amino acid sequence of the $1^{st}$ to $22^{nd}$ amino acids in the amino acid sequence set forth in SEQ ID NO: 1 is the amino acid sequence of the mitochondrial localization signal. Therefore, it was estimated that the protein consisting of the amino acid sequence set forth in SEQ ID NO: 1 is not localized in a chloroplast which is a main site of the fatty acid synthesis of *Nannochloropsis*, and therefore does not influence on the productivity of the fatty acids. Accordingly, the present inventor prepared a transformant in which the mitochondrial localization signal was deleted from the amino acid sequence set forth in SEQ ID NO: 1 and expression of a gene encoding a partial sequence of the ACP to which a chloroplast transit signal sequence functioning within *Nannochloropsis* was added on an N-terminal side is enhanced. As a result, the present inventor found that the productivity of the long-chain fatty acids or the lipids containing the same as components to be produced in the transformant prepared is significantly improved.

In the transformant of the present invention, the expression of at least one of the proteins selected from the group consisting of the proteins (A) to (C), or the expression of a gene encoding at least one of the proteins selected from the group consisting of the proteins (A) to (C) is enhanced. The productivity of long-chain fatty acids or lipid containing the same as components produced in a transformant cell is improved by culturing the transformant of the present invention.

In the transformant of the present invention, the productivity of long-chain fatty acids or lipids containing the same as components, especially a proportion of long-chain fatty acids or lipids containing the same as components in the total fatty acids or lipids to be produced is significantly improved, in comparison with that in a wild type itself. Moreover, as a result, in the transformant of the present invention, the fatty acid composition in the lipid to be produced is modified. Therefore, the transformant of the present invention can be preferably applied to production of fatty acids having specific number of carbon atoms or lipids containing the same as components, particularly long-chain fatty acids or lipids containing the same as components, preferably fatty acids having 18 or more carbon atoms or lipids containing the same as components, more preferably fatty acids having 18 or 20 carbon atoms or lipid containing the same as components, further preferably unsaturated fatty acids having 18 or 20 carbon atoms or lipid containing the same as components, further preferably oleic acid, linoleic acid, α-linolenic acid, γ-linolenic acid, stearidonic acid, dihomo-γ-linolenic acid, eicosatetraenoic acid, arachidonic acid or eicosapentaenoic acid, or lipids containing the same as components, further preferably oleic acid, arachidonic acid or eicosapentaenoic acid, or lipids containing the same as components, and further preferably arachidonic acid or eicosapentaenoic acid, or lipids containing the same as components.

Hereinafter, in the present specification, a cell in which the expression of at least one of the proteins selected from the group consisting of the proteins (A) to (C), or the expression of a gene encoding the same is enhanced is also referred to as the "transformant". On the other hand, a cell in which the expression of at least one of the proteins selected from the group consisting of the proteins (A) to (C), or the expression of a gene encoding the same is not enhanced is also referred to as the "host" or "wild type strain".

Note that, in the present specification, the term "long-chain" means that the number of carbon atoms of the acyl group is 18 or more, and preferably 18 or 20. The productivity of fatty acids and lipids of the transformant can be measured by the method used in Examples described below.

All of the proteins (A) to (C) (hereinafter, also referred to as "ACP1" or "NoACP1") have the acyl-carrier-protein activity (hereinafter, also referred to as "ACP activity"). In the present specification, "ACP activity" means activity which functions as the scaffold of the elongation reaction of the fatty acids by forming the thioester bond with the acyl group of the fatty acids.

A recombinant protein having at least an amino acid sequence of the $23^{rd}$ to $146^{th}$ amino acids set forth in SEQ ID NO: 1 acts as an ACP as demonstrated in the working Examples below. Therefore, the region from $23^{rd}$ to 146th amino acids of the amino acid sequence set forth in SEQ ID NO: 1 is considered to be a sufficient region for the ACP activity.

In the protein (B), the identity with the amino acid sequence of the protein (A) (hereinafter, also referred to as "ACP1(Δ1-22)" or "NoACP1(Δ1-22)") is preferably 75% or more, more preferably 80% or more, further preferably 85% or more, further preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of ACP activity.

Further, specific examples of the protein (B) include a protein in which 1 or several (for example 1 or more and 38 or less, preferably 1 or more and 31 or less, more preferably 1 or more and 25 or less, further preferably 1 or more and 19 or less, furthermore preferably 1 or more and 13 or less, furthermore preferably 1 or more and 10 or less, furthermore preferably 1 or more and 9 or less, furthermore preferably 1 or more and 8 or less, furthermore preferably 1 or more and 7 or less, furthermore preferably 1 or more and 5 or less, furthermore preferably 1 or more and 4 or less, furthermore preferably 1 or more and 3 or less, and furthermore preferably 1 or more and 2 or less) amino acids are deleted, substituted, inserted or added to the amino acid sequence of the protein (A), and having ACP activity.

The protein (C) contains the amino acid sequence of the protein (A) or (B) as a part of the amino acid sequence of the protein (C), and exhibits ACP activity.

In the amino acid sequence constituting the above-described protein (C), a sequence other than the amino acid sequence of the above-described protein (A) or (B) can be appropriately selected within the range in which advantageous effects of the invention are not adversely affected. The examples thereof include the arbitrary amino acid sequence of $1^{st}$ to $22^{nd}$ amino acids of the amino acid sequence set forth in SEQ ID NO: 1, an amino acid sequence in which 1 or several (preferably 1 or more and 20 or less, more preferably 1 or more and 15 or less, further preferably 1 or more and 10 or less, furthermore preferably 1 or more and 5 or less, and furthermore preferably 1 or more and 3 or less) mutations are introduced into the amino acid sequence, and the like. The examples of the mutation include deletion, substitution, insertion and addition of amino acids. These sequences are preferably added to the N-terminal side of the amino acid sequence of the protein (A) or (B).

Alternatively, the above-described protein (C) may be a protein consisting of the amino acid sequence in which a portion on the N-terminal side is deleted in an arbitrary position of the $1^{st}$ to $22^{nd}$ amino acids of the amino acid sequence set forth in SEQ ID NO: 1 in the amino acid sequence set forth in SEQ ID NO: 1. Moreover, the protein (C) also preferably includes a protein consisting of an amino acid sequence formed such that a signal peptide involved in transport or secretion of the protein is added to the amino acid sequence of the protein (A) or (B).

The protein (C) is preferably the following protein (C1). In a case where the host of the transformant of the present invention is microalgae or the like, the protein (A) or (B) is transported to the chloroplast which is the site of the fatty acid synthesis, and localized therein, resulting in increase in a concentration of the protein (A) or (B) in the chloroplast in comparison with that in the host, and the productivity of the long-chain fatty acids is improved.

(C1) A protein wherein the chloroplast transit signal peptide functioning in a host cell is added to the N-terminal side of the amino acid sequence of the protein (A) or (B).

The chloroplast transit signal peptide that can be used in the present invention can be appropriately selected from ordinary chloroplast transit signal peptides. Specific examples thereof include a chloroplast transit signal sequence of a violaxanthin/chlorophyll a binding protein of *Nannochloropsis oculata* strain NIES-2145 (SEQ ID NO: 29; the nucleotide sequence encoding the same, SEQ ID NO: 30), a chloroplast transit signal sequence of an ACP2 (this ACP is a different type of the above-described NoACP) derived from *Nannochloropsis oculata* strain NIES-2145

(SEQ ID NO: 31; the nucleotide sequence encoding the same, SEQ ID NO: 32), a chloroplast transit signal sequence of a β-ketoacyl-ACP synthase III (hereinafter, also referred to as "NoKASIII") derived from *Nannochloropsis oculata* strain NIES-2145 (SEQ ID NO: 33; the nucleotide sequence encoding the same, SEQ ID NO: 34), a chloroplast transit signal sequence of a β-ketoacyl-ACP synthase II (hereinafter, also referred to as "NoKASII") (SEQ ID NO: 27; the nucleotide sequence encoding the same, SEQ ID NO: 28), a chloroplast transit signal sequence of a β-ketoacyl-ACP synthase IV (hereinafter, also referred to as "NoKASIV") (SEQ ID NO: 35; the nucleotide sequence encoding the same, SEQ ID NO: 36), and a chloroplast transit signal sequence of an acyl-ACP thioesterase derived from *Nannochloropsis oculata* strain NIES-2145 (hereinafter, also referred to as "NoTE2") (SEQ ID NO: 37; the nucleotide sequence encoding the same, SEQ ID NO: 38), and the peptide consisting of an amino acid sequence in which 1 or several (preferably 1 or more and 10 or less, more preferably 1 or more and 8 or less, further preferably 1 or more and 6 or less, furthermore preferably 1 or more and 4 or less, and furthermore preferably 1 or more and 2 or less) mutations are introduced into any one of the chloroplast transit signal sequences. The examples of the mutation include deletion, substitution, insertion and addition of amino acids.

Note that the amino acid sequence of $1^{st}$ to $33^{rd}$ amino acids on a side of an N-terminus of the violaxanthin/chlorophyll a binding protein, the amino acid sequence of $1^{st}$ to $44^{th}$ amino acids on a side of an N-terminus of the ACP2, the amino acid sequence of $1^{st}$ to $70^{th}$ amino acids on a side of an N-terminus of the NoKASIII, the amino acid sequence of $1^{st}$ to $33^{rd}$ amino acids on a side of an N-terminus of the NoKASII, the amino acid sequence of $1^{st}$ to $28^{th}$ amino acids on a side of an N-terminus of the NoKASIV, and the amino acid sequence of $1^{st}$ to $73^{rd}$ amino acids on a side of an N-terminus of the NoTE2, are considered to be chloroplast transit signal, respectively. Further, the present inventor confirmed that the amino acid sequence of $1^{st}$ to $33^{rd}$ amino acids on a side of an N-terminus of the violaxanthin/chlorophyll a binding protein, the amino acid sequence of $1^{st}$ to $70^{th}$ amino acids on a side of an N-terminus of the ACP2, the amino acid sequence of $1^{st}$ to $70^{th}$ amino acids on a side of an N-terminus of the NoKASIII, the amino acid sequence of $1^{st}$ to $70^{th}$ amino acids on a side of an N-terminus of the NoKASII, the amino acid sequence of $1^{st}$ to $70^{th}$ amino acids on a side of an N-terminus of the NoKASIV, and the amino acid sequence of $1^{st}$ to $73^{rd}$ amino acids on a side of an N-terminus of the NoTE2 are sufficient for functioning respectively as chloroplast transit signals in a host cell, when the alga belonging to the genus *Nannochloropsis* is used as a host.

The ACP activity of the protein can be confirmed by, for example, introducing a DNA produced by linking a gene encoding the protein to the downstream of a promoter which functions in a host cell, into an ACP gene deletion strain to complement the synthesis ability of fatty acids. Alternatively, the ACP activity can be confirmed by introducing a DNA produced by linking a gene encoding the protein to the downstream of a promoter which functions in a host cell, into a host cell, culturing the thus-obtained cell under the conditions suitable for the expression of the introduced gene, and analyzing any change caused thereby in the fatty acid composition of the host cell or in the cultured liquid by an ordinary technique. Alternatively, the ACP activity can be confirmed by allowing the above-described protein to react with a coenzyme A (CoA) and suitable ACP synthase (phosphopantetheinyl transferase) to form holo-ACP in which the phosphopantetheine group is bonded therewith with reference to literature such as Biochemistry, 2011, vol. 50(25), p. 5704-5717. Alternatively, the ACP activity can be confirmed by allowing the above-described holo-ACP to react with the fatty acids and suitable acyl-ACP synthetase to form acyl-ACP in which the acyl group is bonded therewith with reference to literature such as The Journal of Biological Chemistry, 1979, vol. 254(15), p. 7123-7128.

In general, it is known that an amino acid sequence encoding an enzyme protein does not necessarily exhibit enzyme activity unless the sequence in the whole region is conserved, and there exists a region in which the enzyme activity is not influenced even if the amino acid sequence is changed. In such a region which is not essential to the enzyme activity, even if the mutation of the amino acid, such as deletion, substitution, insertion and addition thereof is introduced thereinto, the activity inherent to the enzyme can be maintained. Also in the present invention, such a protein can be used in which the desired activity is kept and a part of the amino acid sequence is subjected to mutation.

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR, the ODA method, and the Kunkel method. Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) to (C) can be obtained by chemical techniques, genetic engineering techniques or the like that are ordinarily carried out. For example, a natural product-derived protein can be obtained through isolation, purification and the like from *Nannochloropsis oculata*. In addition, the proteins (A) to (C) can be obtained by artificial chemical synthesis based on the amino acid sequence set forth in SEQ ID NO: 1. Alternatively, as recombinant proteins, proteins (A) to (C) may also be produced by gene recombination technologies. In the case of producing a recombinant protein, the acyl carrier protein gene described below can be used.

Note that the algae such as *Nannochloropsis oculata* can be obtained from culture collection such as private or public research institutes or the like. For example, *Nannochloropsis oculata* strain NIES-2145 can be obtained from National Institute for Environmental Studies (NIES).

An example of the gene encoding at least one of the proteins selected from the group consisting of the proteins (A) to (C) (hereinafter, also referred to as "ACP1 gene" or "NoACP1 gene") includes a gene consisting of at least one of the following DNAs (a) to (c):

(a) a DNA consisting of the nucleotide sequence of the $67^{th}$ to $438^{th}$ nucleotides set forth in SEQ ID NO: 2;
(b) a DNA consisting of a nucleotide sequence having 70% or more identity with the nucleotide sequence of the DNA (a), and encoding a protein having ACP activity; and
(c) a DNA containing the nucleotide sequence of the DNA (a) or (b), and encoding a protein having ACP activity.

The gene consisting of the DNA (a) (hereinafter, also referred to as "NoACP1(Δ1-22) gene") is a gene encoding the protein (A). Note that, the nucleotide sequence encoding the mitochondrial localization signal (the amino acid sequence of the $1^{st}$ to $22^{nd}$ amino acids set forth in SEQ ID NO: 1) is a nucleotide sequence corresponding to the $1^{st}$ to $66^{th}$ nucleotides set forth in SEQ ID NO: 2.

In the DNA (b), the identity with the nucleotide sequence of the DNA (a) is preferably 75% or more, more preferably 80% or more, further preferably 85% or more, further preferably 90% or more, further preferably 92% or more, further preferably 93% or more, further preferably 94% or more, further preferably 95% or more, further preferably 96% or more, further preferably 97% or more, further preferably 98% or more, and furthermore preferably 99% or more, in view of ACP activity.

Further, the DNA (b) is also preferably a DNA in which 1 or several (for example 1 or more and 112 or less, preferably 1 or more and 93 or less, more preferably 1 or more and 75 or less, further preferably 1 or more and 56 or less, further preferably 1 or more and 38 or less, further preferably 1 or more and 30 or less, further preferably 1 or more and 27 or less, further preferably 1 or more and 23 or less, further preferably 1 or more and 19 or less, further preferably 1 or more and 15 or less, further preferably 1 or more and 12 or less, further preferably 1 or more and 8 or less, and furthermore preferably 1 or more and 4 or less) nucleotides are deleted, substituted, inserted or added to the nucleotide sequence of the DNA(a), and encoding the protein (A) or (B) having ACP activity.

Furthermore, the DNA (b) is also preferably a DNA capable of hybridizing with a DNA consisting of the nucleotide sequence complementary with the DNA (a) under a stringent condition, and encoding the protein (A) or (B) having ACP activity.

The DNA (c) contains the nucleotide sequence of the DNA (a) or (b) as a part of the nucleotide sequence thereof, and encodes a protein having ACP activity.

In the nucleotide sequence of the DNA (c), a nucleotide sequence other than the nucleotide sequence of the DNA (a) or (b) can be appropriately selected within the range in which the advantageous effects of the present invention are not adversely affected. The examples thereof include an arbitrary nucleotide sequence of $1^{st}$ to $66^{th}$ nucleotides set forth in SEQ ID NO: 2, and a nucleotide sequence in which 1 or several (preferably 1 or more and 60 or less, more preferably 1 or more and 45 or less, further preferably 1 or more and 30 or less, furthermore preferably 1 or more and 15 or less, and furthermore preferably 1 or more and 9 or less) mutations are introduced into the nucleotide sequence, and the like. The examples of the mutation include deletion, substitution, insertion and addition of nucleotides. These sequences are preferably added to the 5' end side of the nucleotide sequence of the DNA (a) or (b).

Alternatively, the DNA (c) may be a DNA consisting of the nucleotide sequence in which a portion on the 5' end side is deleted in an arbitrary position of the $1^{st}$ to $66^{th}$ nucleotides of the nucleotide sequence set forth in SEQ ID NO: 2 in the amino acid sequence set forth in SEQ ID NO: 2. Moreover, a nucleotide sequence encoding a signal peptide involved in transport or secretion of the protein is preferably added to the 5' end side of the nucleotide sequence of DNA (a) or (b).

The DNA (c) is preferably the following DNA (c1). In the case where the host of the transformant of the present invention is microalgae or the like, the protein (A) or (B) is transported to the chloroplast which is the site of the fatty acid synthesis, and localized therein, resulting in increase in a concentration of the protein (A) or (B) in the chloroplast, in comparison with that in the host, and the productivity of the long-chain fatty acids is improved.

(c1) A DNA wherein the nucleotide sequence encoding the chloroplast transit signal peptide functioning in a host cell is added to the 5' end side of the nucleotide sequence of DNA (a) or (b).

The nucleotide sequence encoding the chloroplast transit signal peptide that can be used in the present invention can be appropriately selected from ordinary nucleotide sequence encoding the chloroplast transit signal peptides. Specific examples thereof include nucleotide sequences encoding the above-described chloroplast transit signal peptides.

The method of enhancing the expression of the NoACP1 can be appropriately selected from ordinary method, and a method of enhancing the expression of the NoACP1 gene is preferred. Specific methods thereof include a method of introducing the NoACP1 gene into a host. Moreover, in the case where host has a chloroplast genome, a method of introducing the NoACP1 gene into the chloroplast genome (see CN 103834640 A) is also preferred.

The method of introducing the NoACP1 gene into a host to enhance the expression of the NoACP1 gene is described.

The NoACP1 gene can be obtained by genetic engineering techniques that are ordinarily carried out. For example, the NoACP1 gene can be artificially synthesized based on the amino acid sequence set forth in SEQ ID NO: 1 or the nucleotide sequence set forth in SEQ ID NO: 2. In the present invention, it is preferable to use a plasmid or a cassette for NoACP1 gene expression, which is prepared by operably linking the NoACP1 gene to the downstream of the nucleotide sequence encoding the chloroplast transit signal.

The synthesis of the NoACP1 gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant of the present invention can be prepared by introducing the NoACP1 gene into a host according to an ordinarily method. Specifically, the transformant can be produced by preparing a recombinant vector or a gene expression cassette which is capable of expressing the NoACP1 gene in a host cell, introducing this vector or cassette into a host cell, and thereby transforming the host cell.

The host for the transformant can be appropriately selected from ordinarily used hosts. For example, microorganisms (including algae and microalgae), plants or animals can be used as the host in the present invention. Among these, microorganisms are preferable, and microalgae are more preferable as a host, from the viewpoints of production efficiency and the usability of lipids to be obtained.

As the microorganisms, prokaryotes and eukaryotes can be used, and microorganisms belonging to the genus *Escherichia*, microorganisms belonging to the genus *Bacillus*, microorganisms belonging to the genus *Synechocystis*, microorganisms belonging to the genus *Synechococcus*, eukaryotic microorganisms such as yeast and filamentous fungi, or the like can be used. Among these, from a viewpoint of the productivity of lipids, *Escherichia coli, Bacillus*

*subtilis, Rhodosporidium toruloides*, or *Mortierella* sp., is preferred, and *Escherichia coli* is more preferred.

As the algae or microalgae, from a viewpoint of establishment of a gene recombination technique, algae belonging to the genus *Chlamydomonas*, algae belonging to the genus *Chlorella*, algae belonging to the genus *Phaeodactylum*, or algae belonging to the genus *Nannochloropsis* are preferred, and algae belonging to the genus *Nannochloropsis* are more preferred. Specific examples of the algae belonging to the genus *Nannochloropsis* include *Nannochloropsis oculata, Nannochloropsis gaditana, Nannochloropsis salina, Nannochloropsis oceanica, Nannochloropsis atomus, Nannochloropsis maculata, Nannochloropsis granulata,* and *Nannochloropsis* sp. Among these, from a viewpoint of the productivity of lipids, *Nannochloropsis oculata* or *Nannochloropsis gaditana* is preferred, and *Nannochloropsis oculata* is more preferred.

As the plants, from a viewpoint of a high lipid content of seeds, *Arabidopsis thaliana, Brassica napus, Brassica raga, Cocos nucifera, Elaeis quineensis, cuphea, Glycine max, Zea mays, Oryza sativa, Helianthus annuus, Cinnamomum camphora*, or *Jatropha curcas* is preferred, and *Arabidopsis thaliana* is more preferred.

A vector for use as the plasmid for gene expression or a vector containing the gene expression cassette (plasmid) may be any vector capable of introducing the gene encoding the target protein into a host, and expressing the target gene in the host cell. For example, a vector which has expression regulation regions such as a promoter and a terminator in accordance with the type of the host to be used, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, in the case of using a microorganism as the host, pBluescript (pBS) II SK(-) (manufactured by Stratagene), a pSTV-based vector (manufactured by Takara Bio), a pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (1986, Plasmid 15(2), p. 93-103), pBR322 (manufactured by Takara Bio), pRS403 (manufactured by Stratagene), and pMW218/219 (manufactured by Nippon Gene). In particular, in the case of using *Escherichia coli* as the host, pBluescript II SK(-) or pMW218/219 is preferably used.

When the algae or the microalgae are used as the host, specific examples of the vector include pUC19 (manufactured by Takara Bio), P66 (*Chlamydomonas* Center), P-322 (*Chlamydomonas* Center), pPha-T1 (see Journal of Basic Microbiology, 2011, vol. 51, p. 666-672) and pJET1 (manufactured by COSMO BIO). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Proceedings of the National Academy of Sciences of the United States of America, 2011, vol. 108(52), by using the DNA fragment (gene expression cassette) consisting of the target gene, a promoter and a terminator.

In the case of using a plant cell as the host, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host, a pRI-based vector or a pBI-based vector is preferably used.

Specific examples of this DNA fragment include a DNA fragment amplified by PCR method, and a restriction enzyme-cut DNA fragment. Introduction of the gene encoding a target protein to the vector can be conducted by an ordinary technique such as restriction enzyme treatment and ligation.

Moreover, a kind of promoter regulating the expression of the gene encoding a target protein, which is introduced into the expression vector, can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), Rubisco operon (rbc), PSI reaction center protein (psaAB), D1 protein of PSII (psbA), cauliflower mosaic virus 35S RNA promoter, promoters for housekeeping genes (e.g., tubulin promoter, actin promoter and ubiquitin promoter), *Brassica napus* or *Brassica rapa*-derived Napin gene promoter, plant-derived Rubisco promoter, a promoter of a violaxanthin/(chlorophyll a)-binding protein gene derived from the genus *Nannochloropsis* (VCP1 promoter, VCP2 promoter) (Proceedings of the National Academy of Sciences of the United States of America, 2011, vol. 108(52)), and a promoter of an oleosin-like protein LDSP (lipid droplet surface protein) gene derived from the genus *Nannochloropsis* (PLOS Genetics, 2012, vol. 8(11): e1003064. DOI: 10.1371). In the case of using *Nannochloropsis* as the host in the present invention, the promoter of violaxanthin/(chlorophyll a)-binding protein gene, or the promoter of an oleosin-like protein LDSP gene derived from the genus *Nannochloropsis* can be preferably used.

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

The method for transformation can be appropriately selected from ordinary techniques according to a kind of the host to be used. Examples of the method for transformation include a transformation method of using calcium ion, a general competent cell transformation method, a protoplast transformation method, an electroporation method, an LP transformation method, a method of using *Agrobacterium*, a particle gun method, and the like. When the algae belonging to the genus *Nannochloropsis* are used as the host, transformation can also be performed by using the electroporation method described in Nature Communications, DOI: 10.1038/ncomms1688, 2012, or the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR method using a genome as a template or the like.

In the transformant of the present invention, also expression of a β-Ketoacyl-ACP synthase (hereinafter, also referred to as "KAS") is preferably enhanced.

The KAS is one kind of fatty acid synthetic enzymes which catalyze the condensation reaction of an acyl-ACP with a malonyl-ACP, and is involved in the synthesis of acyl-ACP. In the chloroplast, the elongation reaction of the carbon chain is repeated starting from an acetyl-ACP (or acetyl-CoA), and finally an acyl-ACP having 16 or 18 carbon atoms is synthesized. Then, an acyl-ACP thioesterase (hereinafter, also merely referred to as "TE") hydrolyzes the thioester bond of the acyl-ACP to form a free fatty acid.

In the first stage of the fatty acid synthesis, an acetoacetyl-ACP is formed by a condensation reaction between the acetyl-ACP (or acetyl-CoA) and a malonyl-ACP. The KAS catalyzes this reaction. Then, the keto group of the acetoacetyl-ACP is reduced by a β-ketoacyl-ACP reductase, to produce a hydroxybutyryl-ACP. Subsequently, the hydroxybutyryl-ACP is dehydrated by a β-hydroxyacyl-ACP dehydrase, to produce a crotonyl-ACP. Finally, the crotonyl-ACP is reduced by an enoyl-ACP reductase, to produce a butyryl-ACP. The butyryl-ACP in which two carbon atoms are added to the carbon chain of the acyl group of the acetyl-ACP is produced by a series of these reactions. Hereinafter, the similar reactions are repeated to cause elongation of the carbon chain of the acyl-ACP, and an acyl-ACP having 16 or 18 carbon atoms is finally synthesized.

Therefore, the productivity of the lipids, particularly the productivity of the fatty acids in the transformant used for producing the lipids can be further improved by enhancing expression of a gene encoding the KAS (hereinafter, also referred to as "KAS gene").

The KAS that can be preferably used in the present invention merely needs to be the protein having β-ketoacyl-ACP synthase activity (hereinafter, also referred to as "KAS activity"). Herein, the term "KAS activity" means the activity to catalyze the condensation reaction of the acetyl-ACP or the acyl-ACP with the malonyl-ACP.

The KAS activity of the protein can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or in the cultured liquid by an ordinary technique. Alternatively, the KAS activity can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction which uses acyl-ACPs, as substrates.

KAS is categorized into KAS I, KAS II, KAS III and KAS IV according to their substrate specificity. For example, KAS III uses an acetyl-ACP (or acetyl-CoA) having 2 carbon atoms as the substrate to catalyze the elongation reaction that the number of carbon atoms is increased from 2 to 4. KAS I mainly catalyzes the elongation reaction that the number of carbon atoms is increased from 4 to 16, to synthesize the palmitoyl-ACP having 16 carbon atoms. KAS II mainly catalyzes the elongation reaction to the long-chain acyl group having 18 carbon atoms or more, to synthesize a long-chain acyl-ACP. KAS IV mainly catalyzes the elongation reaction that the number of carbon atoms is increased from 6 to 14, to synthesize a medium-chain acyl-ACP.

Therefore, the productivity of long-chain fatty acids is further improved by enhancing expression of a gene encoding a KAS II.

The KAS, which can be preferably used in the present invention, can be appropriately selected from the normal KAS or proteins functionally equivalent thereto, according to a kind of host or the like. Specific examples thereof include the NoKAS II (SEQ ID NO: 27; the nucleotide sequence of the gene encoding the same, SEQ ID NO: 28). Moreover, as the proteins functionally equivalent thereto, a protein consisting of an amino acid sequence having 50% or more (preferably 70% or more, more preferably 80% or more, and further preferably 90% or more) identity with the amino acid sequence of the NoKASII, and having KAS activity, can be also used.

Further, in the transformant of the present invention, the expression of at least one kind of genes selected from the group consisting of a gene encoding a desaturase (hereinafter, also referred to as "desaturase gene"), and a gene encoding an elongase (hereinafter, also referred to as "elongase gene").

It is known that long-chain fatty acids having 18 or more carbon atoms, particularly, long-chain PUFA, is synthesized by a number of desaturases or elongases outside the chloroplast such as an endoplasmic reticula. Therefore, the productivity of long-chain fatty acids, especially long-chain PUFA, is further improved also by enhancing expression of a gene encoding the desaturase or the elongase.

The desaturase or elongase, which can be preferably used in the present invention, can be appropriately selected from the normal desaturase or elongase, or proteins functionally equivalent to the desaturase or elongase, according to a kind of host or the like. For example, the desaturase or elongase derived from *Nannochloropsis* described in WO 2012/149457 or US 2012/0277418 can be preferably used.

Examples of the desaturase which can be used in the present invention include a Δ12-desaturase (hereinafter, also referred to as "Δ12-DES"), a Δ6-desaturase (hereinafter, also referred to as "Δ6-DES"), an ω3-desaturase (hereinafter, also referred to as "ω3-DES"), a Δ5-desaturase (hereinafter, also referred to as "Δ5-DES"), and a Δ9-desaturase (hereinafter, also referred to as "Δ9-DES").

In addition, in the present invention, the desaturase may be used alone or in combination with two or more kinds thereof.

In the present specification, the term "Δ12-DES" means a protein (enzyme) that catalyzes a reaction of introducing an unsaturated bond into a Δ12-position of oleic acid to produce linoleic acid (hereinafter, also denoted as "C18:2Δ(9, 12)"). Then, in the present specification, the term "Δ12-desaturase activity" (hereinafter, also referred to as "Δ12-DES activity") means activity for introducing the unsaturated bond into the Δ12-position of oleic acid (hereinafter, also denoted as "C18:1(Δ9)"). It can be confirmed that the protein has the Δ12-DES activity by a system using a Δ12-DES gene deletion strain, for example. Alternatively, it can also be confirmed by examining formation of linoleic acid by introducing the DNA of which a gene encoding the above-described protein is ligated downstream of a promoter functioning in a host cell, into the Δ12-DES gene deletion strain. Alternatively, it can also be confirmed by measuring a decrease of oleic acid amount or an increase of linoleic acid amount according to an ordinary method by preparing the Δ12-DES or cell lysate containing the same to react the resultant material with the reaction solution containing oleic acid, oleoyl-CoA, an ester compound with oleic acid and glycerol, or the like.

As shown in Examples mentioned later, a proportion of the amount of PUFA such as C18:2(Δ9,12) in the total amount of the fatty acids is further improved by enhancing the expression of the Δ12-DES in the transformant of the present invention.

The Δ12-DES, which can be preferably used in the present invention, can be appropriately selected from the normal Δ12-DES or proteins functionally equivalent thereto, according to a kind of host or the like. Specific examples thereof include a Δ12-DES derived from *Nannochloropsis oculata* (hereinafter, also referred to as "NoΔ12-DES") (SEQ ID NO: 39) or a Δ12-DES derived from *Nannochloropsis gaditana* (hereinafter, also referred to as "NgΔ12-DES") (SEQ ID NO: 49). Moreover, as the proteins functionally equivalent thereto, a protein consisting of an amino acid sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the amino acid sequence of the NoΔ12-DES or the NgΔ12-DES, and having Δ12-DES activity, can be also used.

Further, a protein in which 1 or several (for example 1 or more and 176 or less, preferably 1 or more and 154 or less, more preferably 1 or more and 132 or less, further preferably 1 or more and 110 or less, furthermore preferably 1 or more and 88 or less, furthermore preferably 1 or more and 66 or less, furthermore preferably 1 or more and 44 or less, furthermore preferably 1 or more and 36 or less, furthermore preferably 1 or more and 22 or less, furthermore preferably 1 or more and 9 or less, and furthermore preferably 1 or more and 5 or less) amino acids are deleted, substituted, inserted or added to the amino acid sequence of the protein consisting of the amino acid sequence set forth in SEQ ID NO: 39, and having Δ12-DES activity can be also used. Alternatively, a protein in which 1 or several (for example 1 or more and 181 or less, preferably 1 or more and 159 or less, more preferably 1 or more and 136 or less, further preferably 1 or more and 113 or less, furthermore preferably 1 or more and 91 or less, furthermore preferably 1 or more and 68 or less, furthermore preferably 1 or more and 46 or less, furthermore preferably 1 or more and 37 or less, furthermore preferably 1 or more and 23 or less, furthermore preferably 1 or more and 10 or less, and furthermore preferably 1 or more and 5 or less) amino acids are deleted, substituted, inserted or added to the amino acid sequence of the protein consisting of the amino acid sequence set forth in SEQ ID NO: 49, and having Δ12-DES activity can be also used.

Examples of a gene encoding the NoΔ12-DES include a gene consisting of a DNA consisting of the nucleotide sequence set forth in SEQ ID NO: 40, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 40, and encoding a protein having Δ12-DES activity. Examples of a gene encoding the NgΔ12-DES include a gene consisting of a DNA consisting of the nucleotide sequence set forth in SEQ ID NO: 50, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 50, and encoding a protein having Δ12-DES activity.

Further, a gene consisting of a DNA in which 1 or several (for example 1 or more and 527 or less, preferably 1 or more and 461 or less, more preferably 1 or more and 396 or less, further preferably 1 or more and 330 or less, further preferably 1 or more and 264 or less, further preferably 1 or more and 198 or less, further preferably 1 or more and 132 or less, further preferably 1 or more and 106 or less, further preferably 1 or more and 66 or less, further preferably 1 or more and 27 or less, and furthermore preferably 1 or more and 14 or less) nucleotides are deleted, substituted, inserted or added to the nucleotide sequence of the DNA consisting of the nucleotide sequence set forth in SEQ ID NO: 40, and encoding a protein having Δ12-DES activity, can be also used. Alternatively, a gene consisting of a DNA in which 1 or several (for example 1 or more and 544 or less, preferably 1 or more and 476 or less, more preferably 1 or more and 408 or less, further preferably 1 or more and 340 or less, further preferably 1 or more and 272 or less, further preferably 1 or more and 204 or less, further preferably 1 or more and 136 or less, further preferably 1 or more and 109 or less, further preferably 1 or more and 68 or less, further preferably 1 or more and 28 or less, and furthermore preferably 1 or more and 14 or less) nucleotides are deleted, substituted, inserted or added to the nucleotide sequence of the DNA consisting of the nucleotide sequence set forth in SEQ ID NO: 50, and encoding a protein having Δ12-DES activity, can be also used.

Furthermore, a gene consisting of a DNA capable of hybridizing with a DNA consisting of the nucleotide sequence complementary with the DNA consisting of the nucleotide sequence set forth in SEQ ID NO: 40 or 50 under a stringent condition, and encoding a protein having Δ12-DES activity, can be also used.

In the present specification, the term "Δ6-DES" means a protein (enzyme) that catalyzes a reaction of introducing an unsaturated bond into a Δ6-position of linoleic acid (hereinafter, also denoted as "C18:2Δ9,12") to produce γ-linolenic acid (hereinafter, also denoted as "C18:3Δ6,9,12"). Then, in the present specification, the term "Δ6-desaturase activity" (hereinafter, also referred to as "Δ6-DES activity") means activity for introducing the unsaturated bond into the Δ6-position of linoleic acid. It can be confirmed that the protein has the Δ6-DES activity by a system using a Δ6-DES gene deletion strain, for example. Alternatively, it can also be confirmed by examining formation of γ-linolenic acid by introducing the DNA of which a gene encoding the above-described protein is ligated downstream of a promoter functioning in a host cell, into the Δ6-DES gene deletion strain. Alternatively, it can also be confirmed by measuring a decrease of linoleic acid amount or an increase of γ-linolenic acid amount according to an ordinary method by preparing the Δ6-DES or cell lysate containing the same to react the resultant material with the reaction solution containing linoleic acid, linoleoyl-CoA, an ester compound with linoleic acid and glycerol, or the like.

As shown also in Examples mentioned later, a proportion of the amount of PUFA such as C18:3(Δ6,9,12), dihomo-γ-linolenic acid (hereinafter, also denoted as "C20:3(Δ8,11, 14)") and arachidonic acid (hereinafter, also denoted as "C20:4(Δ5,8,11,14)") in the total amount of the fatty acids is further improved by enhancing the expression of the Δ6-DES together with the above-mentioned Δ12 DES in the transformant of the present invention.

The Δ6-DES, which can be preferably used in the present invention, can be appropriately selected from the normal Δ6-DES or proteins functionally equivalent thereto, according to a kind of host or the like. Specific examples thereof include a Δ6-DES derived from *Nannochloropsis oculata* (hereinafter, also referred to as "NoΔ6-DES") (SEQ ID NO: 41) or a Δ6-DES derived from *Nannochloropsis gaditana* (hereinafter, also referred to as "NgΔ6-DES") (SEQ ID NO: 51). Moreover, as the proteins functionally equivalent thereto, a protein consisting of an amino acid sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the amino acid sequence of the NoΔ6-DES or the NgΔ6-DES, and having Δ6-DES activity, can be also used.

Further, a protein in which 1 or several (for example 1 or more and 190 or less, preferably 1 or more and 166 or less, more preferably 1 or more and 143 or less, further preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less) amino acids are deleted, substituted, inserted or added to the amino acid sequence of the protein consisting of the amino acid sequence set forth in SEQ ID NO: 41, and having Δ6-DES activity can be also used. Alternatively, a protein in which 1 or several (for example 1 or more and 190 or less, preferably 1 or more and 166 or less, more preferably 1 or more and 143 or less, further preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less) amino acids are deleted, substituted, inserted or added to the amino acid sequence of the protein consisting of the amino acid sequence set forth in SEQ ID NO: 51, and having Δ6-DES activity can be also used.

Examples of a gene encoding the NoΔ6-DES include a gene consisting of a DNA consisting of the nucleotide sequence set forth in SEQ ID NO: 42, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 42, and encoding a protein having Δ6-DES activity. Examples of a gene encoding the NgΔ6-DES include a gene consisting of a DNA consisting of the nucleotide sequence set forth in SEQ ID NO: 52, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 52, and encoding a protein having Δ6-DES activity.

Further, a gene consisting of a DNA in which 1 or several (for example 1 or more and 570 or less, preferably 1 or more and 499 or less, more preferably 1 or more and 428 or less, further preferably 1 or more and 357 or less, further preferably 1 or more and 285 or less, further preferably 1 or more and 214 or less, further preferably 1 or more and 143 or less, further preferably 1 or more and 114 or less, further preferably 1 or more and 72 or less, further preferably 1 or more and 29 or less, and furthermore preferably 1 or more and 15 or less) nucleotides are deleted, substituted, inserted or added to the nucleotide sequence of the DNA consisting of the nucleotide sequence set forth in SEQ ID NO: 42, and encoding a protein having Δ6-DES activity, can be also used. Alternatively, a gene consisting of a DNA in which 1 or several (for example 1 or more and 572 or less, preferably 1 or more and 500 or less, more preferably 1 or more and 429 or less, further preferably 1 or more and 357 or less, further preferably 1 or more and 286 or less, further preferably 1 or more and 215 or less, further preferably 1 or more and 143 or less, further preferably 1 or more and 115 or less, further preferably 1 or more and 72 or less, further preferably 1 or more and 29 or less, and furthermore preferably 1 or more and 15 or less) nucleotides are deleted, substituted, inserted or added to the nucleotide sequence of the DNA consisting of the nucleotide sequence set forth in SEQ ID NO: 52, and encoding a protein having Δ6-DES activity, can be also used.

Furthermore, a gene consisting of a DNA capable of hybridizing with a DNA consisting of the nucleotide sequence complementary with the DNA consisting of the nucleotide sequence set forth in SEQ ID NO: 42 or 52 under a stringent condition, and encoding a protein having Δ6-DES activity, can be also used.

In the present specification, the term "ω3-DES" means a protein (enzyme) that catalyzes a reaction of introducing an unsaturated bond into an ω3-position of arachidonic acid to produce eicosapentaenoic acid (hereinafter, also denoted as "EPA" or "C20:5Δ5,8,11,14,17"). Then, in the present specification, the term "ω3-desaturase activity" (hereinafter, also referred to as "ω3-DES activity") means activity for introducing the unsaturated bond into the ω3-position of arachidonic acid. It can be confirmed that the protein has the ω3-DES activity by a system using an ω3-DES gene deletion strain, for example. Alternatively, it can also be confirmed by examining formation of EPA by introducing the DNA of which a gene encoding the above-described protein is ligated downstream of a promoter functioning in a host cell, into the ω3-DES gene deletion strain. Alternatively, it can also be confirmed by measuring a decrease of arachidonic acid amount or an increase of EPA amount according to an ordinary method by preparing the ω3-DES or cell lysate containing the same to react the resultant material with the reaction solution containing arachidonic acid derivatives (a thioester compound with CoA, an ester compound with glycerol, or the like).

As shown in Examples mentioned later, a proportion of the amount of PUFA such as C20:5(Δ5,8,11,14,17) in the total amount of the fatty acids is further improved by enhancing the expression of the ω3-DES in the transformant of the present invention. Moreover, a proportion of the amount of PUFA such as C20:5(Δ5,8,11,14,17) in the total amount of the fatty acids is further improved by enhancing the expression of the ω3-DES together with the Δ12-DES mentioned above.

The ω3-DES, which can be preferably used in the present invention, can be appropriately selected from the normal ω3-DES or proteins functionally equivalent thereto, according to a kind of host or the like. Specific examples thereof include an ω3-DES derived from *Nannochloropsis oculata* (hereinafter, also referred to as "Noω3-DES") (SEQ ID NO: 43) or an ω3-DES derived from *Nannochloropsis gaditana* (hereinafter, also referred to as "Ngω3-DES") (SEQ ID NO: 53). Moreover, as the proteins functionally equivalent thereto, a protein consisting of an amino acid sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the amino acid sequence of the Noω3-DES or the Ngω3-DES, and having ω3-DES activity, can be also used.

Further, a protein in which 1 or several (for example 1 or more and 164 or less, preferably 1 or more and 144 or less, more preferably 1 or more and 123 or less, further preferably 1 or more and 103 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less) amino acids are deleted, substituted, inserted or added to the amino acid sequence of the protein consisting of the amino acid sequence set forth in SEQ ID NO: 43, and having ω3-DES activity can be also used. Alternatively, a protein in which 1 or several (for example 1 or more and 163 or less, preferably 1 or more and 143 or less, more preferably 1 or more and 123 or less, further preferably 1 or more and 102 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less) amino acids are deleted, substituted, inserted or added to the amino acid sequence of the protein consisting of the amino acid sequence set forth in SEQ ID NO: 53, and having ω3-DES activity can be also used.

Examples of a gene encoding the Noω3-DES include a gene consisting of a DNA consisting of the nucleotide sequence set forth in SEQ ID NO: 44, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 44, and encoding a protein having ω3-DES activity. Examples of a gene encoding the Ngω3-DES include a gene consisting of a DNA consisting of the nucleotide sequence set forth in SEQ ID NO: 54, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 54, and encoding a protein having ω3-DES activity.

Further, a gene consisting of a DNA in which 1 or several (for example 1 or more and 494 or less, preferably 1 or more and 432 or less, more preferably 1 or more and 370 or less, further preferably 1 or more and 309 or less, further preferably 1 or more and 247 or less, further preferably 1 or more and 185 or less, further preferably 1 or more and 124 or less, further preferably 1 or more and 99 or less, further preferably 1 or more and 62 or less, further preferably 1 or more and 25 or less, and furthermore preferably 1 or more and 13 or less) nucleotides are deleted, substituted, inserted or added to the nucleotide sequence of the DNA consisting of the nucleotide sequence set forth in SEQ ID NO: 44, and encoding a protein having ω3-DES activity, can be also used. Alternatively, a gene consisting of a DNA in which 1 or several (for example 1 or more and 490 or less, preferably 1 or more and 429 or less, more preferably 1 or more and 368 or less, further preferably 1 or more and 306 or less, further preferably 1 or more and 245 or less, further preferably 1 or more and 184 or less, further preferably 1 or more and 123 or less, further preferably 1 or more and 98 or less, further preferably 1 or more and 62 or less, further preferably 1 or more and 25 or less, and furthermore preferably 1 or more and 13 or less) nucleotides are deleted, substituted, inserted or added to the nucleotide sequence of the DNA consisting of the nucleotide sequence set forth in SEQ ID NO: 54, and encoding a protein having ω3-DES activity, can be also used.

Furthermore, a gene consisting of a DNA capable of hybridizing with a DNA consisting of the nucleotide sequence complementary with the DNA consisting of the nucleotide sequence set forth in SEQ ID NO: 44 or 54 under a stringent condition, and encoding a protein having ω3-DES activity, is also preferred.

In the present specification, the term "Δ5-DES" means a protein (enzyme) that catalyzes a reaction of introducing an unsaturated bond into a Δ5-position of dihomo-γ-linolenic acid to produce arachidonic acid. Then, in the present specification, the term "Δ5-desaturase activity" (hereinafter, also referred to as "Δ5-DES activity") means activity for introducing the unsaturated bond into the Δ5-position of dihomo-γ-linolenic acid. It can be confirmed that the protein has the Δ5-DES activity by a system using a Δ5-DES gene deletion strain, for example. Alternatively, it can also be confirmed by examining formation of arachidonic acid by introducing the DNA of which a gene encoding the above-described protein is ligated downstream of a promoter functioning in a host cell, into the Δ5-DES gene deletion strain. Alternatively, it can also be confirmed by measuring a decrease of dihomo-γ-linolenic acid amount or an increase of arachidonic acid amount according to an ordinary method by preparing the Δ5-DES or cell lysate containing the same to react the resultant material with the reaction solution containing dihomo-γ-linolenic acid derivatives (a thioester compound with CoA, an ester compound with glycerol, or the like).

The Δ5-DES, which can be preferably used in the present invention, can be appropriately selected from the normal Δ5-DES or proteins functionally equivalent thereto, according to a kind of host or the like. Specific examples thereof include a Δ5-DES derived from *Nannochloropsis oculata* (hereinafter, also referred to as "NoΔ5-DES") (SEQ ID NO: 45) or a Δ5-DES derived from *Nannochloropsis gaditana* (hereinafter, also referred to as "NgΔ5-DES") (SEQ ID NO: 55). Moreover, as the proteins functionally equivalent thereto, a protein consisting of an amino acid sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the amino acid sequence of the NoΔ5-DES or the NgΔ5-DES, and having Δ5-DES activity, can be also used.

Further, a protein in which 1 or several (for example 1 or more and 211 or less, preferably 1 or more and 185 or less, more preferably 1 or more and 158 or less, further preferably 1 or more and 132 or less, furthermore preferably 1 or more and 106 or less, furthermore preferably 1 or more and 79 or less, furthermore preferably 1 or more and 53 or less, furthermore preferably 1 or more and 43 or less, furthermore preferably 1 or more and 27 or less, furthermore preferably 1 or more and 11 or less, and furthermore preferably 1 or more and 6 or less) amino acids are deleted, substituted, inserted or added to the amino acid sequence of the protein consisting of the amino acid sequence set forth in SEQ ID NO: 45, and having Δ5-DES activity can be also used. Alternatively, a protein in which 1 or several (for example 1 or more and 206 or less, preferably 1 or more and 181 or less, more preferably 1 or more and 155 or less, further preferably 1 or more and 129 or less, furthermore preferably 1 or more and 103 or less, furthermore preferably 1 or more and 78 or less, furthermore preferably 1 or more and 52 or less, furthermore preferably 1 or more and 42 or less, furthermore preferably 1 or more and 26 or less, furthermore preferably 1 or more and 11 or less, and furthermore preferably 1 or more and 6 or less) amino acids are deleted, substituted, inserted or added to the amino acid sequence of the protein consisting of the amino acid sequence set forth in SEQ ID NO: 55, and having Δ5-DES activity can be also used.

Examples of a gene encoding the NoΔ5-DES include a gene consisting of a DNA consisting of the nucleotide sequence set forth in SEQ ID NO: 46, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 46, and encoding a protein having Δ5-DES activity. Examples of a gene encoding the NgΔ5-DES include a gene consisting of a DNA consisting of the nucleotide sequence set forth in SEQ ID NO: 56, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 56, and encoding a protein having Δ5-DES activity.

Further, a gene consisting of a DNA in which 1 or several (for example 1 or more and 633 or less, preferably 1 or more and 554 or less, more preferably 1 or more and 475 or less, further preferably 1 or more and 396 or less, further preferably 1 or more and 317 or less, further preferably 1 or more and 238 or less, further preferably 1 or more and 159 or less, further preferably 1 or more and 127 or less, further preferably 1 or more and 80 or less, further preferably 1 or more and 32 or less, and furthermore preferably 1 or more and 16 or less) nucleotides are deleted, substituted, inserted or added to the nucleotide sequence of the DNA consisting of the nucleotide sequence set forth in SEQ ID NO: 46, and encoding a protein having Δ5-DES activity, can be also used. Alternatively, a gene consisting of a DNA in which 1 or several (for example 1 or more and 620 or less, preferably 1 or more and 542 or less, more preferably 1 or more and 465 or less, further preferably 1 or more and 387 or less, further preferably 1 or more and 310 or less, further preferably 1 or more and 233 or less, further preferably 1 or more and 155 or less, further preferably 1 or more and 124 or less, further preferably 1 or more and 78 or less, further preferably 1 or more and 31 or less, and furthermore preferably 1 or more and 16 or less) nucleotides are deleted, substituted, inserted or added to the nucleotide sequence of the DNA consisting of the nucleotide sequence set forth in SEQ ID NO: 56, and encoding a protein having Δ5-DES activity, can be also used.

Furthermore, a gene consisting of a DNA capable of hybridizing with a DNA consisting of the nucleotide sequence complementary with the DNA consisting of the nucleotide sequence set forth in SEQ ID NO: 46 or 56 under a stringent condition, and encoding a protein having Δ5-DES activity, is also preferred.

In the present specification, the term "Δ9-DES" means a protein (enzyme) that catalyzes a reaction of introducing an unsaturated bond into a Δ9-position of stearic acid (hereinafter, also denoted as "C18:0") to produce oleic acid (hereinafter, also denoted as "C18:1(Δ9)"). Then, in the present specification, the term "Δ9-desaturase activity" (hereinafter, also referred to as "Δ9-DES activity") means activity for introducing the unsaturated bond into the Δ9-position of stearic acid. It can be confirmed that the protein has the Δ9-DES activity by a system using a Δ9-DES gene deletion strain, for example. Alternatively, it can also be confirmed by examining formation of oleic acid by introducing the DNA of which a gene encoding the above-described protein is ligated downstream of a promoter functioning in a host cell, into the Δ9-DES gene deletion strain. Alternatively, it can also be confirmed by measuring a decrease of stearic acid amount or an increase of oleic acid amount according to an ordinary method by preparing the Δ9-DES or cell lysate containing the same to react the resultant material with the reaction solution containing stearic acid, stearoyl-CoA, or the like.

As shown in Examples mentioned later, a proportion of the amount of long-chain fatty acids such as C18:1(Δ9) in the total amount of the fatty acids is further improved by enhancing the expression of the Δ9-DES in the transformant of the present invention. Moreover, a proportion of the amount of long-chain fatty acids such as linoleic acid (hereinafter, also denoted as "C18:2Δ9,12") in the total amount of the fatty acids is further improved by enhancing the expression of the Δ9-DES together with the Δ12-DES mentioned above.

The Δ9-DES, which can be preferably used in the present invention, can be appropriately selected from the normal Δ9-DES or proteins functionally equivalent thereto, according to a kind of host or the like. Specific examples thereof include a Δ9-DES derived from *Nannochloropsis oculata* (hereinafter, also referred to as "NoΔ9-DES") (SEQ ID NO: 47) or a Δ9-DES derived from *Nannochloropsis gaditana* (hereinafter, also referred to as "NgΔ9-DES") (SEQ ID NO: 57). Moreover, as the proteins functionally equivalent thereto, a protein consisting of an amino acid sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the amino acid sequence of the NoΔ9-DES or the NgΔ9-DES, and having Δ9-DES activity, can be also used.

Further, a protein in which 1 or several (for example 1 or more and 144 or less, preferably 1 or more and 126 or less, more preferably 1 or more and 108 or less, further preferably 1 or more and 90 or less, furthermore preferably 1 or more and 72 or less, furthermore preferably 1 or more and 54 or less, furthermore preferably 1 or more and 36 or less, furthermore preferably 1 or more and 29 or less, furthermore preferably 1 or more and 18 or less, furthermore preferably 1 or more and 8 or less, and furthermore preferably 1 or more and 4 or less) amino acids are deleted, substituted, inserted or added to the amino acid sequence of the protein consisting of the amino acid sequence set forth in SEQ ID NO: 47, and having Δ9-DES activity can be also used. Alternatively, a protein in which 1 or several (for example 1 or more and 136 or less, preferably 1 or more and 119 or less, more preferably 1 or more and 102 or less, further preferably 1 or more and 85 or less, furthermore preferably 1 or more and 68 or less, furthermore preferably 1 or more and 51 or less, furthermore preferably 1 or more and 34 or less, furthermore preferably 1 or more and 28 or less, furthermore preferably 1 or more and 17 or less, furthermore preferably 1 or more and 7 or less, and furthermore preferably 1 or more and 4 or less) amino acids are deleted, substituted, inserted or added to the amino acid sequence of the protein consisting of the amino acid sequence set forth in SEQ ID NO: 57, and having Δ9-DES activity can be also used.

Examples of a gene encoding the NoΔ9-DES include a gene consisting of a DNA consisting of the nucleotide sequence set forth in SEQ ID NO: 48, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 48, and encoding a protein having Δ9-DES activity. Examples of a gene encoding the NgΔ9-DES include a gene consisting of a DNA consisting of the nucleotide sequence set forth in SEQ ID NO: 58, and a gene consisting of a DNA consisting of a nucleotide sequence having 60% or more (preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more) identity with the nucleotide sequence set forth in SEQ ID NO: 58, and encoding a protein having Δ9-DES activity.

Further, a gene consisting of a DNA in which 1 or several (for example 1 or more and 432 or less, preferably 1 or more and 378 or less, more preferably 1 or more and 324 or less, further preferably 1 or more and 270 or less, further preferably 1 or more and 216 or less, further preferably 1 or more and 162 or less, further preferably 1 or more and 108 or less, further preferably 1 or more and 87 or less, further preferably 1 or more and 54 or less, further preferably 1 or more and 22 or less, and furthermore preferably 1 or more and 11 or less) nucleotides are deleted, substituted, inserted or added to the nucleotide sequence of the DNA consisting of the nucleotide sequence set forth in SEQ ID NO: 48, and encoding a protein having Δ9-DES activity, can be also used. Alternatively, a gene consisting of a DNA in which 1 or several (for example 1 or more and 410 or less, preferably 1 or more and 359 or less, more preferably 1 or more and 307 or less, further preferably 1 or more and 256 or less, further preferably 1 or more and 205 or less, further preferably 1 or more and 154 or less, further preferably 1 or more and 103 or less, further preferably 1 or more and 82 or less, further preferably 1 or more and 52 or less, further preferably 1 or more and 21 or less, and furthermore preferably 1 or more and 11 or less) nucleotides are deleted, substituted, inserted or added to the nucleotide sequence of the DNA consisting of the nucleotide sequence set forth in SEQ ID NO: 58, and encoding a protein having Δ9-DES activity, can be also used.

Furthermore, a gene consisting of a DNA capable of hybridizing with a DNA consisting of the nucleotide sequence complementary with the DNA consisting of the nucleotide sequence set forth in SEQ ID NO: 48 or 58 under a stringent condition, and encoding a protein having Δ9-DES activity, is also preferred.

In the transformant of the present invention, from a view point of more improving the productivity of long-chain fatty acids, the expression of one or more enzyme selected from the group consisting of the Δ12-DES, the Δ6-DES, the ω3-DES, and the Δ9-DES is preferably enhanced, and two or more enzymes selected from the group consisting of the Δ12-DES, the Δ6-DES, the ω3-DES, and the Δ9-DES are further preferably enhanced.

Moreover, the transformant of the present invention preferably has enhancing expression of a TE, and preferably also has enhancing expression of a gene encoding the TE (hereinafter, also referred to as "TE gene").

As described above, TE is an enzyme that hydrolyzes the thioester bond of the acyl-ACP synthesized by a fatty acid synthetic enzyme such as the KAS to produce a free fatty acid. The function of the TE terminates the fatty acid synthesis on the ACP, and then the thus-hydrolyzed fatty acid is supplied to the synthesis of PUFA, triacylglycerol or the like. Therefore, lipid productivity, particularly productivity of the fatty acids of the transformant to be used for the lipid production can be further improved by enhancing the expression of the TE, preferably by enhancing the expression of the TE gene.

The TE that can be used in the present invention merely needs to be the protein having acyl-ACP thioesterase activity (hereinafter, also referred to as "TE activity"). Herein, the term "TE activity" means an activity of hydrolyzing the thioester bond of the acyl-ACP.

To date, several TEs having different reaction specificities depending on the number of carbon atoms and the number of unsaturated bonds of the acyl group (fatty acid residue) constituting the acyl-ACP substrate are identified. Therefore, TE is considered to be an important factor in determining the fatty acid composition of an organism. In particular, when a host originally having no genes encoding a TE is used in the transformation, introduction of genes encoding a TE, preferably genes encoding a TE having substrate specificity to the long-chain acyl-ACP is effective. The productivity of PUFA is further improved by introducing such a gene.

The TE that can be used in the present invention can be appropriately selected from ordinary TEs and proteins functionally equivalent thereto, according to a kind of host or the like. Specific examples thereof include a TE derived from *Nannochloropsis gaditana* (SEQ ID NO: 59); a TE derived from *Nannochloropsis oculata* (SEQ ID NO: 60 or 37); and a TE derived from *Nannochloropsis granulata* (SEQ ID NO: 61). Moreover, as the proteins functionally equivalent thereto, a protein consisting of an amino acid sequence having 50% or more (preferably 70% or more, more preferably 80% or more, and further preferably 90% or more) identity with the amino acid sequence of any one of the TEs described above, and having TE activity, can be also used.

The amino acid sequence information of the KAS, the desaturase, the elongase and the TE, and the nucleotide sequence information of the genes encoding the same can be obtained from, for example, National Center for Biotechnology Information (NCBI), or the like.

Further, the transformant in which the expression of the KAS gene, the desaturase gene, the elongase gene, or the TE gene is enhanced can be prepared by an ordinary method. For example, the transformant can be prepared by a method similar to the above-described method for enhancing the expression of the NoACP1 gene, such as a method for introducing the each gene into a host, a method for modifying expression regulation regions (promoter, terminator, or the like) of the gene in the host having the each gene on a genome, or the like.

In the transformant of the present invention, productivity of long-chain fatty acids or lipids containing the same as components is improved in comparison with that in the host in which the expression of any one of the proteins (A) to (C) is not enhanced. Accordingly, if the transformant of the present invention is cultured under suitable conditions and then the long-chain fatty acids or the lipids containing the same as components are collected from an obtained cultured product or an obtained growth product, the long-chain fatty acids or the lipids containing the same as components can be efficiently produced. Herein, the term "cultured product" means liquid medium and a transformant subjected to cultivation, and the term "growth product" means a transformant subjected to growth.

The culture condition of the transformant of the present invention can be appropriately selected in accordance with the type of the host, and any ordinary used culture condition for the host can be employed. Further, from a viewpoint of the production efficiency of fatty acids, for example, precursor substances involved in the fatty acid biosynthesis system, such as glycerol, acetic acid or glucose, may be added to the medium.

For example, in the case of using *Escherichia coli* as the host, culturing of *Escherichia coli* may be carried out in LB medium or Overnight Express Instant TB Medium (Novagen) at 30 to 37° C. for half a day to 1 day.

In the case of using *Arabidopsis* as the host, for example, growth of *Arabidopsis* may be carried out at soil under the temperature conditions of 20 to 25° C., by continuously irradiating white light or under light illumination conditions of a light period of 16 hours and a dark period of 8 hours, for one to two months.

In the case of using algae as the host, medium based on natural seawater or artificial seawater may be used. Alternatively, commercially available culture medium may also be used. Specific examples of the culture medium include f/2 medium, ESM medium, Daigo's IMK medium, L1 medium and MNK medium. Above all, from viewpoints of an improvement in the lipid productivity and a nutritional ingredient concentration, f/2 medium, ESM medium or Daigo's IMK medium is preferred, f/2 medium or Daigo's IMK medium is more preferred, and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the algae to be seeded to the culture medium is appropriately selected. In view of viability, the amount is preferably 1% (vol/vol) or more, per culture medium. The upper limit thereof is preferably 50% (vol/vol) or less, and more preferably 10% (vol/vol) or less. The range of an amount of the transformant to be seeded is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the temperature is preferably 10° C. or more, and more preferably 15° C. or more. The upper limit thereof is preferably 35° C. or less, and more preferably 30° C. or less. The range of the culture temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably 100 lx or more, more preferably 300 lx or more, and further preferably 1,000 lx or more. The upper limit thereof is preferably 50,000 lx or less, more preferably 10,000 lx or less, and further preferably 6,000 lx or less. The range of irradiance during the light irradiation is preferably 100 to 50,000 lx, more preferably 300 to 10,000 lx, and further preferably 1,000 to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably 8 hours or more, and more preferably 10 hours or more. The upper limit thereof is preferably 24 hours or less, and more preferably 18 hours or less. The range of the light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the concentration is preferably 0.03% (which is the same degree as the concentration under atmospheric conditions) or more, more preferably 0.05% or more, further preferably 0.1% or more, and furthermore preferably 0.3% or more. The upper limit thereof is preferably 10% or less, more preferably 5% or less, further preferably 3% or less, and furthermore preferably 1% or less. The range of the concentration of carbon dioxide is preferably from 0.03 to 10%, more preferably from 0.05 to 5%, further preferably from 0.1 to 3%, and furthermore preferably from 0.3 to 1%. A concentration of carbonate is not particularly limited. When sodium hydrogen carbonate is used, for example, from viewpoints of the growth promotion and the improvement in the productivity of fatty acids, the concentration is preferably 0.01% by mass or more, more preferably 0.05% by mass or more, and further preferably 0.1% by mass or more. The upper limit thereof is preferably 5% by mass or less, more preferably 2% by mass or less, and further preferably 1% by mass or less. The range of the concentration of sodium hydrogen carbonate is preferably from 0.01 to 5% by mass, more preferably from 0.05 to 2% by mass, and further preferably from 0.1 to 1% by mass.

Culture time is not particularly limited, and the culture may be performed for a long time (for example, about 150 days) so that an alga body in which the lipids are accumulated at a high concentration can grow at a high concentration. The culture time is preferably 3 days or more, and more preferably 7 days or more. The upper limit thereof is preferably 90 days or less, and more preferably 30 days or less. The range of the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, aerated and agitated culture or shaking culture is preferred, and aerated and agitated culture is more preferred.

A method of collecting the lipids from the cultured product or growth product is appropriately selected from an ordinary method. For example, lipid components can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scale culturing, lipids can be obtained by collecting oil components from the cultured product or growth product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain fatty acids or fatty acid compounds, and more preferably contain fatty acids or fatty acid ester compounds, in view of usability thereof. The fatty acid ester compound is preferably at least one kind selected from the group consisting of MAG, DAG, and TAG, and more preferably TAG.

In view of usability for a surfactant or the like, and from a nutritional viewpoint, the fatty acid or the ester compound thereof contained in the lipid is preferably a long-chain fatty acid or an ester compound thereof. Specifically, the fatty acid or the ester compound thereof contained in the lipid is preferably a fatty acid having 18 or more carbon atoms or an ester compound thereof, more preferably a fatty acid having 18 or 20 carbon atoms or an ester compound thereof, more preferably an unsaturated fatty acid having 18 or 20 carbon atoms or an ester compound thereof, more preferably an oleic acid, a linoleic acid, an α-linolenic acid, a γ-linolenic acid, a stearidonic acid, a dihomo-γ-linolenic acid, an eicosatetraenoic acid, an arachidonic acid or an eicosapentaenoic acid, or an ester compound thereof, more preferably an oleic acid, an arachidonic acid or an eicosapentaenoic acid, or an ester thereof, and further preferably an arachidonic acid or an eicosapentaenoic acid, or an ester thereof.

From a viewpoint of the productivity, the fatty acid ester compound is preferably a simple lipid or a complex lipid, more preferably a simple lipid, and further preferably a triacylglycerol.

The lipid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing lipids, methods of modifying fatty acid composition of lipids to be produced, proteins, genes, recombinant vectors or DNA cassettes, transformants and methods of preparing the same, described below.

<1> A method of producing lipids, containing the steps of:
  culturing a transformant into which a gene encoding at least one of the proteins selected from the group consisting of the following proteins (A) to (C) is introduced; and
  producing fatty acids or lipids containing the same as components:
(A) A protein consisting of the amino acid sequence of the $23^{rd}$ to $146^{th}$ amino acids set forth in SEQ ID NO: 1;
(B) A protein consisting of an amino acid sequence having 70% or more, preferably 75% or more, more preferably 80% or more, more preferably 85% or more, more preferably 90% or more, more preferably 92% or more, more preferably 93% or more, more preferably 94% or more, more preferably 95% or more, more preferably 96% or more, more preferably 97% or more, more preferably 98% or more, and further preferably 99% or more identity with the amino acid sequence of the protein (A), and having ACP activity; and
(C) A protein containing the amino acid sequence of the protein (A) or (B), and having ACP activity.

<2> A method of producing lipids, containing the steps of:
  culturing a transformant into which a gene encoding at least one of the proteins selected from the group consisting of the proteins (A) to (C) is introduced; and
  improving productivity of long-chain fatty acids or lipids containing the same as components to be produced in a cell of the transformant.

<3> A method of modifying fatty acid composition, containing the steps of:
  culturing a transformant into which a gene encoding at least one of the proteins selected from the group consisting of the proteins (A) to (C) is introduced; and
  increasing a proportion of long-chain fatty acids in the whole fatty acids to be produced in a cell of the transformant.

<4> A method of producing lipids, containing the steps of:
  culturing a transformant wherein the expression of a gene encoding at least one of the proteins selected from the group consisting of the proteins (A) to (C) is enhanced; and
  producing fatty acids or lipids containing the same as components.

<5> A method of producing lipids, containing the steps of:
culturing a transformant wherein the expression of a gene encoding at least one of the proteins selected from the group consisting of the proteins (A) to (C) is enhanced; and
improving the productivity of long-chain fatty acids or lipids containing the same as components, produced in a cell of the transformant.
<6> A method of modifying fatty acid composition, containing the steps of:
culturing a transformant wherein the expression of a gene encoding at least one of the proteins selected from the group consisting of the proteins (A) to (C) is enhanced; and
increasing a proportion of long-chain fatty acids in the whole fatty acids to be produced in a cell of the transformant.
<7> The method described in any one of the above items <4> to <6>, wherein the gene encoding at least one of the proteins selected from the group consisting of the proteins (A) to (C) is introduced into a host, to enhance the expression of the gene.
<8> The method described in any one of the above items <1> to <7>, wherein the gene encoding at least one of the proteins selected from the group consisting of the proteins (A) to (C) is incorporated into a chloroplast genome of the transformant.
<9> The method described in any one of the above items <1> to <8>, wherein a concentration of at least one of the proteins selected from the group consisting of the proteins (A) to (C) is increased in the transformant, in comparison with that in the host.
<10> The method described in any one of the above items <1> to <9>, wherein the protein (B) consists of an amino acid sequence in which 1 or several, preferably 1 or more and 38 or less, more preferably 1 or more and 31 or less, further preferably 1 or more and 25 or less, furthermore preferably 1 or more and 19 or less, furthermore preferably 1 or more and 13 or less, furthermore preferably 1 or more and 10 or less, furthermore preferably 1 or more and 9 or less, furthermore preferably 1 or more and 8 or less, furthermore preferably 1 or more and 7 or less, furthermore preferably 1 or more and 5 or less, furthermore preferably 1 or more and 4 or less, furthermore preferably 1 or more and 3 or less, and furthermore preferably 1 or more and 2 or less amino acids are deleted, substituted, inserted or added to the amino acid sequence of the protein (A).
<11> The method described in any one of the above items <1> to <10>, wherein the protein (C) is the following protein (C1):
(C1) A protein wherein a chloroplast transit signal peptide functioning in a host cell is added to the N terminal side of the amino acid sequence of the protein (A) or (B).
<12> The method described in the above item <11>, wherein the chloroplast transit signal peptide is a chloroplast transit signal sequence of a VCP1 of *Nannochloropsis oculata* strain NIES-2145, a chloroplast transit signal sequence of an ACP derived from *Nannochloropsis oculata* strain NIES-2145, a chloroplast transit signal sequence of a β-ketoacyl-ACP synthase III derived from *Nannochloropsis oculata* strain NIES-2145, a chloroplast transit signal sequence of a β-ketoacyl-ACP synthase II derived from *Nannochloropsis oculata* strain NIES-2145, a chloroplast transit signal sequence of a β-ketoacyl-ACP synthase IV derived from *Nannochloropsis oculata* strain NIES-2145 or a chloroplast transit signal sequence of an acyl-ACP thioesterase derived from *Nannochloropsis oculata* strain NIES-2145, or the peptide consisting of an amino acid sequence in which 1 or several, preferably 1 or more and 10 or less, more preferably 1 or more and 8 or less, further preferably 1 or more and 6 or less, furthermore preferably 1 or more and 4 or less, and furthermore preferably 1 or more and 2 or less mutations are introduced thereinto.
<13> The method described in any one of the above items <1> to <12>, wherein the gene encoding at least one of the proteins selected from the group consisting of the proteins (A) to (C) is a gene consisting of any one of the following DNAs (a) to (c):
(a) a DNA consisting of the nucleotide sequence of the $67^{th}$ to $438^{th}$ nucleotides set forth in SEQ ID NO: 2;
(b) a DNA consisting of a nucleotide sequence having 70% or more, preferably 75% or more, more preferably 80% or more, further preferably 85% or more, furthermore preferably 90% or more, furthermore preferably 92% or more, furthermore preferably 93% or more, furthermore preferably 94% or more, furthermore preferably 95% or more, furthermore preferably 96% or more, furthermore preferably 97% or more, furthermore preferably 98% or more, and furthermore preferably 99% or more identity with the nucleotide sequence of the DNA (a), and encoding a protein having ACP activity; and
(c) a DNA containing the nucleotide sequence of the DNA (a) or (b), and encoding a protein having ACP activity.
<14> The method described in the above item <13>, wherein the DNA (b) is a DNA consisting of a nucleotide sequence in which 1 or several, preferably 1 or more and 112 or less, more preferably 1 or more and 93 or less, further preferably 1 or more and 75 or less, furthermore preferably 1 or more and 56 or less, furthermore preferably 1 or more and 38 or less, furthermore preferably 1 or more and 30 or less, furthermore preferably 1 or more and 27 or less, furthermore preferably 1 or more and 23 or less, furthermore preferably 1 or more and 19 or less, furthermore preferably 1 or more and 15 or less, furthermore preferably 1 or more and 12 or less, furthermore preferably 1 or more and 8 or less, and furthermore preferably 1 or more and 4 or less nucleotides, are deleted, substituted, inserted or added to the nucleotide sequence of the DNA (a), and encoding the protein (A) or (B) having ACP activity, or a DNA capable of hybridizing with a DNA consisting of the nucleotide sequence complementary with the DNA (a) under a stringent condition, and encoding the protein (A) or (B) having ACP activity.
<15> The method described in the above item <13> or <14>, wherein the DNA (c) is the following DNA (c1):
(c1) a DNA wherein a nucleotide sequence encoding a chloroplast transit signal functioning in a host cell is added to the 5' end side of the nucleotide sequence of the DNA (a) or (b).
<16> The method described in the above item <15>, wherein the nucleotide sequence encoding a chloroplast transit signal peptide is a nucleotide sequence encoding a chloroplast transit signal sequence of a VCP1 in *Nannochloropsis oculata* strain NIES-2145, a chloroplast transit signal sequence of an ACP derived from *Nannochloropsis oculata* strain NIES-2145, a chloroplast transit signal sequence of a β-ketoacyl-ACP synthase III derived from *Nannochloropsis oculata* strain NIES-2145, a chloroplast transit signal sequence of a β-ketoacyl-ACP synthase II derived from *Nannochloropsis oculata* strain NIES-2145, a chloroplast transit signal sequence of a β-ketoacyl-ACP synthase IV derived from *Nannochloropsis oculata* strain NIES-2145 or a chloroplast transit signal sequence of an acyl-ACP thioesterase derived from *Nannochloropsis oculata* strain NIES-2145.

<17> The method described in any one of the above items <1> to <16>, wherein the transformant is a transformant of microorganism.
<18> The method described in the above item <17>, wherein the microorganism is a microalga.
<19> The method described in the above item <18>, wherein the microalga is an alga belonging to the genus *Nannochloropsis*.
<20> The method described in the above item <18> or <19>, wherein the microalga is selected from the group consisting of *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp., preferably selected from the group consisting of *Nannochloropsis oculata* and *Nannochloropsis gaditana*, or more preferably *Nannochloropsis oculata*.
<21> The method described in the above item <17>, wherein the microorganism is *Escherichia coli*.
<22> The method described in any one of the above items <1> to <21>, wherein expression of a KAS gene is enhanced in the transformant.
<23> The method described in the above item <22>, wherein the KAS is a protein consisting of the amino acid sequence set forth in SEQ ID NO: 27, or a protein consisting of an amino acid sequence having 50% or more, preferably 70% or more, more preferably 80% or more, and further preferably 90% or more identity with the amino acid sequence of the protein, and having KAS activity.
<24> The method described in any one of the above items <1> to <23>, wherein expression of a desaturase gene is enhanced in the transformant.
<25> The method described in the above item <24>, wherein the desaturase is at least one of the desaturases selected from the group consisting of a Δ12-DES, a Δ6-DES, an ω3-DES, a Δ5-DES and a Δ9-DES, preferably at lease any one of the desaturases selected from the group consisting of a Δ12-DES, a Δ6-DES, an ω3-DES and a Δ9-DES, or more preferably two or more of the desaturases selected from the group consisting of a Δ12-DES, a Δ6-DES, an ω3-DES and a Δ9-DES.
<26> The method described in the above item <25>, wherein the Δ12-DES is a protein consisting of the amino acid sequence set forth in SEQ ID NO: 39 or 49; a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence set forth in SEQ ID NO: 39 or 49, and having Δ12-DES activity; a protein in which 1 or several (for example 1 or more and 176 or less, preferably 1 or more and 154 or less, more preferably 1 or more and 132 or less, further preferably 1 or more and 110 or less, furthermore preferably 1 or more and 88 or less, furthermore preferably 1 or more and 66 or less, furthermore preferably 1 or more and 44 or less, furthermore preferably 1 or more and 36 or less, furthermore preferably 1 or more and 22 or less, furthermore preferably 1 or more and 9 or less, and furthermore preferably 1 or more and 5 or less) amino acids are deleted, substituted, inserted or added to the amino acid sequence set forth in SEQ ID NO: 39, and having Δ12-DES activity; or a protein in which 1 or several (for example 1 or more and 181 or less, preferably 1 or more and 159 or less, more preferably 1 or more and 136 or less, further preferably 1 or more and 113 or less, furthermore preferably 1 or more and 91 or less, furthermore preferably 1 or more and 68 or less, furthermore preferably 1 or more and 46 or less, furthermore preferably 1 or more and 37 or less, furthermore preferably 1 or more and 23 or less, furthermore preferably 1 or more and 10 or less, and furthermore preferably 1 or more and 5 or less) amino acids are deleted, substituted, inserted or added to the amino acid sequence set forth in SEQ ID NO: 49, and having Δ12-DES activity.
<27> The method described in the above item <25> or <26>, wherein a gene encoding the Δ12-DES is a gene consisting of a DNA consisting of the nucleotide sequence set forth in SEQ ID NO: 40 or 50; a gene consisting of a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence set forth in SEQ ID NO: 40 or 50, and encoding a protein having Δ12-DES activity; a gene in which 1 or several (for example 1 or more and 527 or less, preferably 1 or more and 461 or less, more preferably 1 or more and 396 or less, further preferably 1 or more and 330 or less, further preferably 1 or more and 264 or less, further preferably 1 or more and 198 or less, further preferably 1 or more and 132 or less, further preferably 1 or more and 106 or less, further preferably 1 or more and 66 or less, further preferably 1 or more and 27 or less, and furthermore preferably 1 or more and 14 or less) nucleotides are deleted, substituted, inserted or added to a nucleotide sequence of a DNA consisting of the nucleotide sequence set forth in SEQ ID NO: 40, and encoding a protein having Δ12-DES activity; a gene in which 1 or several (for example 1 or more and 544 or less, preferably 1 or more and 476 or less, more preferably 1 or more and 408 or less, further preferably 1 or more and 340 or less, further preferably 1 or more and 272 or less, further preferably 1 or more and 204 or less, further preferably 1 or more and 136 or less, further preferably 1 or more and 109 or less, further preferably 1 or more and 68 or less, further preferably 1 or more and 28 or less, and furthermore preferably 1 or more and 14 or less) nucleotides are deleted, substituted, inserted or added to a nucleotide sequence of a DNA consisting of the nucleotide sequence set forth in SEQ ID NO: 50, and encoding a protein having Δ12-DES activity; or a gene consisting of a DNA capable of hybridizing with a DNA consisting of the nucleotide sequence complementary with the DNA consisting of the nucleotide sequence set forth in SEQ ID NO: 40 or 50 under a stringent condition, and encoding a protein having Δ12-DES activity.
<28> The method described in any one of the above items <25> to <27>, wherein the Δ6-DES is a protein consisting of the amino acid sequence set forth in SEQ ID NO: 41 or 51; a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence set forth in SEQ ID NO: 41 or 51, and having Δ6-DES activity; a protein in which 1 or several (for example 1 or more and 190 or less, preferably 1 or more and 166 or less, more preferably 1 or more and 143 or less, further preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less) amino acids are deleted, substituted, inserted or added to the amino acid sequence set forth in SEQ ID NO: 41, and having Δ6-DES activity; or a protein in which 1 or several (for example 1 or more and 190 or less, preferably 1 or more and 166 or less, more preferably 1 or more and 143 or less, further preferably 1 or more and 119 or less, furthermore preferably 1 or more and 95 or less, furthermore preferably 1 or more and 72 or less, furthermore preferably 1 or more and 48 or less, furthermore preferably 1 or more and 38 or less, furthermore preferably 1 or more and 24 or less, furthermore preferably 1 or more and 10 or less, and furthermore preferably 1 or more and 5 or less) amino acids are deleted, substituted, inserted or added to the amino acid sequence set forth in SEQ ID NO: 51, and having Δ6-DES activity.

<29> The method described in any one of the above items <25> to <28>, wherein a gene encoding the Δ6-DES is a gene consisting of a DNA consisting of the nucleotide sequence set forth in SEQ ID NO: 42 or 52; a gene consisting of a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence set forth in SEQ ID NO: 42 or 52, and encoding a protein having Δ6-DES activity; a gene in which 1 or several (for example 1 or more and 570 or less, preferably 1 or more and 499 or less, more preferably 1 or more and 428 or less, further preferably 1 or more and 357 or less, further preferably 1 or more and 285 or less, further preferably 1 or more and 214 or less, further preferably 1 or more and 143 or less, further preferably 1 or more and 114 or less, further preferably 1 or more and 72 or less, further preferably 1 or more and 29 or less, and furthermore preferably 1 or more and 15 or less) nucleotides are deleted, substituted, inserted or added to a nucleotide sequence of a DNA consisting of the nucleotide sequence set forth in SEQ ID NO: 42, and encoding a protein having Δ6-DES activity; a gene in which 1 or several (for example 1 or more and 572 or less, preferably 1 or more and 500 or less, more preferably 1 or more and 429 or less, further preferably 1 or more and 357 or less, further preferably 1 or more and 286 or less, further preferably 1 or more and 215 or less, further preferably 1 or more and 143 or less, further preferably 1 or more and 115 or less, further preferably 1 or more and 72 or less, further preferably 1 or more and 29 or less, and furthermore preferably 1 or more and 15 or less) nucleotides are deleted, substituted, inserted or added to a nucleotide sequence of a DNA consisting of the nucleotide sequence set forth in SEQ ID NO: 52, and encoding a protein having Δ6-DES activity; or a gene consisting of a DNA capable of hybridizing with a DNA consisting of the nucleotide sequence complementary with the DNA consisting of the nucleotide sequence set forth in SEQ ID NO: 42 or 52 under a stringent condition, and encoding a protein having Δ6-DES activity.

<30> The method described in any one of the above items <25> to <29>, wherein the ω3-DES is a protein consisting of the amino acid sequence set forth in SEQ ID NO: 43 or 53; a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence set forth in SEQ ID NO: 43 or 53, and having ω3-DES activity; a protein in which 1 or several (for example 1 or more and 164 or less, preferably 1 or more and 144 or less, more preferably 1 or more and 123 or less, further preferably 1 or more and 103 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less) amino acids are deleted, substituted, inserted or added to the amino acid sequence set forth in SEQ ID NO: 43, and having ω3-DES activity; or a protein in which 1 or several (for example 1 or more and 163 or less, preferably 1 or more and 143 or less, more preferably 1 or more and 123 or less, further preferably 1 or more and 102 or less, furthermore preferably 1 or more and 82 or less, furthermore preferably 1 or more and 62 or less, furthermore preferably 1 or more and 41 or less, furthermore preferably 1 or more and 33 or less, furthermore preferably 1 or more and 21 or less, furthermore preferably 1 or more and 9 or less, and furthermore preferably 1 or more and 5 or less) amino acids are deleted, substituted, inserted or added to the amino acid sequence set forth in SEQ ID NO: 53, and having ω3-DES activity.

<31> The method described in any one of the above items <25> to <30>, wherein a gene encoding the ω3-DES is a gene consisting of a DNA consisting of the nucleotide sequence set forth in SEQ ID NO: 44 or 54; a gene consisting of a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence set forth in SEQ ID NO: 44 or 54, and encoding a protein having ω3-DES activity; a gene in which 1 or several (for example 1 or more and 494 or less, preferably 1 or more and 432 or less, more preferably 1 or more and 370 or less, further preferably 1 or more and 309 or less, further preferably 1 or more and 247 or less, further preferably 1 or more and 185 or less, further preferably 1 or more and 124 or less, further preferably 1 or more and 99 or less, further preferably 1 or more and 62 or less, further preferably 1 or more and 25 or less, and furthermore preferably 1 or more and 13 or less) nucleotides are deleted, substituted, inserted or added to a nucleotide sequence of a DNA consisting of the nucleotide sequence set forth in SEQ ID NO: 44, and encoding a protein having ω3-DES activity; a gene in which 1 or several (for example 1 or more and 490 or less, preferably 1 or more and 429 or less, more preferably 1 or more and 368 or less, further preferably 1 or more and 306 or less, further preferably 1 or more and 245 or less, further preferably 1 or more and 184 or less, further preferably 1 or more and 123 or less, further preferably 1 or more and 98 or less, further preferably 1 or more and 62 or less, further preferably 1 or more and 25 or less, and furthermore preferably 1 or more and 13 or less) nucleotides are deleted, substituted, inserted or added to a nucleotide sequence of a DNA consisting of the nucleotide sequence set forth in SEQ ID NO: 54, and encoding a protein having ω3-DES activity; or a gene consisting of a DNA capable of hybridizing with a DNA consisting of the nucleotide sequence complementary with the DNA consisting of the nucleotide sequence set forth in SEQ ID NO: 44 or 54 under a stringent condition, and encoding a protein having ω3-DES activity.

<32> The method described in any one of the above items <25> to <31>, wherein the Δ5-DES is a protein consisting of the amino acid sequence set forth in SEQ ID NO: 45 or 55; a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence set forth in SEQ ID NO: 45 or 55, and having Δ5-DES activity; a protein in which 1 or several (for example 1 or more and 211 or less, preferably 1 or more and 185 or less, more preferably 1 or more and 158 or less, further preferably 1 or more and 132 or less, furthermore preferably 1 or more and 106 or less, furthermore preferably 1 or more and 79 or less, furthermore preferably 1 or more and 53 or less, furthermore preferably 1 or more and 43 or less, furthermore preferably 1 or more and 27 or less, furthermore preferably 1 or more and 11 or less, and furthermore preferably 1 or more and 6 or less) amino acids are deleted, substituted, inserted or added to the amino acid sequence set forth in SEQ ID NO: 45, and having Δ5-DES activity; or a protein in which 1 or several (for example 1 or more and 206 or less, preferably 1 or more and 181 or less, more preferably 1 or more and 155 or less, further preferably 1 or more and 129 or less, furthermore preferably 1 or more and 103 or less, furthermore preferably 1 or more and 78 or less, furthermore preferably 1 or more and 52 or less, furthermore preferably 1 or more and 42 or less, furthermore preferably 1 or more and 26 or less, furthermore preferably 1 or more and 11 or less, and furthermore preferably 1 or more and 6 or less) amino acids are deleted, substituted, inserted or added to the amino acid sequence set forth in SEQ ID NO: 55, and having Δ5-DES activity.

<33> The method described in any one of the above items <25> to <32>, wherein a gene encoding the Δ5-DES is a gene consisting of a DNA consisting of the nucleotide sequence set forth in SEQ ID NO: 46 or 56; a gene consisting of a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence set forth in SEQ ID NO: 46 or 56, and encoding a protein having Δ5-DES activity; a gene in which 1 or several (for example 1 or more and 633 or less, preferably 1 or more and 554 or less, more preferably 1 or more and 475 or less, further preferably 1 or more and 396 or less, further preferably 1 or more and 317 or less, further preferably 1 or more and 238 or less, further preferably 1 or more and 159 or less, further preferably 1 or more and 127 or less, further preferably 1 or more and 80 or Jess, further preferably 1 or more and 32 or less, and furthermore preferably 1 or more and 16 or less) nucleotides are deleted, substituted, inserted or added to a nucleotide sequence of a DNA consisting of the nucleotide sequence set forth in SEQ ID NO: 46, and encoding a protein having Δ5-DES activity; a gene in which 1 or several (for example 1 or more and 620 or less, preferably 1 or more and 542 or less, more preferably 1 or more and 465 or less, further preferably 1 or more and 387 or less, further preferably 1 or more and 310 or less, further preferably 1 or more and 233 or less, further preferably 1 or more and 155 or less, further preferably 1 or more and 124 or less, further preferably 1 or more and 78 or less, further preferably 1 or more and 31 or less, and furthermore preferably 1 or more and 16 or less) nucleotides are deleted, substituted, inserted or added to a nucleotide sequence of a DNA consisting of the nucleotide sequence set forth in SEQ ID NO: 56, and encoding a protein having Δ5-DES activity; or a gene consisting of a DNA capable of hybridizing with a DNA consisting of the nucleotide sequence complementary with the DNA consisting of the nucleotide sequence set forth in SEQ ID NO: 46 or 56 under a stringent condition, and encoding a protein having Δ5-DES activity.

<34> The method described in any one of the above items <25> to <33>, wherein the Δ9-DES is a protein consisting of the amino acid sequence set forth in SEQ ID NO: 47 or 57; a protein consisting of an amino acid sequence having 60% or more, preferably 65% or more, more preferably 70% or more, more preferably 75% or more, more preferably 80% or more, more preferably 85% or more, more preferably 90% or more, more preferably 92% or more, more preferably 95% or more, more preferably 98% or more, and further preferably 99% or more identity with the amino acid sequence set forth in SEQ ID NO: 47 or 57, and having Δ9-DES activity; a protein in which 1 or several (for example 1 or more and 144 or less, preferably 1 or more and 126 or less, more preferably 1 or more and 108 or less, further preferably 1 or more and 90 or less, furthermore preferably 1 or more and 72 or less, furthermore preferably 1 or more and 54 or less, furthermore preferably 1 or more and 36 or less, furthermore preferably 1 or more and 29 or less, furthermore preferably 1 or more and 18 or less, furthermore preferably 1 or more and 8 or less, and furthermore preferably 1 or more and 4 or less) amino acids are deleted, substituted, inserted or added to the amino acid sequence set forth in SEQ ID NO: 47, and having Δ9-DES activity; or a protein in which 1 or several (for example 1 or more and 136 or less, preferably 1 or more and 119 or less, more preferably 1 or more and 102 or less, further preferably 1 or more and 85 or less, furthermore preferably 1 or more and 68 or less, furthermore preferably 1 or more and 51 or less, furthermore preferably 1 or more and 34 or less, furthermore preferably 1 or more and 28 or less, furthermore preferably 1 or more and 17 or less, furthermore preferably 1 or more and 7 or less, and furthermore preferably 1 or more and 4 or less) amino acids are deleted, substituted, inserted or added to the amino acid sequence set forth in SEQ ID NO: 57, and having Δ9-DES activity.

<35> The method described in any one of the above items <25> to <34>, wherein a gene encoding the Δ9-DES is a gene consisting of a DNA consisting of the nucleotide sequence set forth in SEQ ID NO: 48 or 58; a gene consisting of a DNA consisting of a nucleotide sequence having 60% or more, preferably 65% or more, more preferably 70% or more, further preferably 75% or more, furthermore preferably 80% or more, furthermore preferably 85% or more, furthermore preferably 90% or more, furthermore preferably 92% or more, furthermore preferably 95% or more, furthermore preferably 98% or more, and furthermore preferably 99% or more identity with the nucleotide sequence set forth in SEQ ID NO: 48 or 58, and encoding a protein having Δ9-DES activity; a gene in which 1 or several (for example 1 or more and 432 or less, preferably 1 or more and 378 or less, more preferably 1 or more and 324 or less, further preferably 1 or more and 270 or less, further preferably 1 or more and 216 or less, further preferably 1 or more and 162 or less, further preferably 1 or more and 108 or less, further preferably 1 or more and 87 or less, further preferably 1 or more and 54 or less, further preferably 1 or more and 22 or less, and furthermore preferably 1 or more and 11 or less) nucleotides are deleted, substituted, inserted or added to a nucleotide sequence of a DNA consisting of the nucleotide sequence set forth in SEQ ID NO: 48, and encoding a protein having Δ9-DES activity; a gene in which 1 or several (for example 1 or more and 410 or less, preferably 1 or more and 359 or less, more preferably 1 or more and 307 or less, further preferably 1 or more and 256 or less, further preferably 1 or more and 205 or less, further preferably 1 or more and 154 or less, further preferably 1 or more and 103 or less, further preferably 1 or more and 82 or less, further preferably 1 or more and 52 or less, further preferably 1 or more and 21 or less, and furthermore preferably 1 or more and 11 or less) nucleotides are deleted, substituted, inserted or added to a nucleotide sequence of a DNA consisting of the nucleotide sequence set forth in SEQ ID NO: 58, and encoding a protein having Δ9-DES activity; or a gene consisting of a DNA capable of hybridizing with a DNA consisting of the nucleotide sequence complementary with the DNA consisting of the nucleotide sequence set forth in SEQ ID NO: 48 or 58 under a stringent condition, and encoding a protein having Δ9-DES activity.

<36> The method described in any one of the above items <1> to <35>, wherein expression of an elongase gene is enhanced in the transformant.

<37> The method described in any one of the above items <1> to <36>, wherein expression of a TE gene is enhanced in the transformant.

<38> The method described in the above item <37>, wherein the TE is a protein consisting of any one of the amino acid sequences set forth in SEQ ID NO: 37 and 59 to 61, or a protein consisting of an amino acid sequence having 50% or more, preferably 70% or more, more preferably 80% or more, and further preferably 90% or more identity with the amino acid sequence of the protein, and having TE activity.

<39> The method described in any one of the above items <1> to <38>, wherein the fatty acids or lipids contain a long-chain fatty acid or a fatty acid ester compound thereof, preferably a fatty acid having 18 or more carbon atoms or a fatty acid ester compound thereof, more preferably a fatty acid having 18 or 20 carbon atoms or a fatty acid ester compound thereof, more preferably an unsaturated fatty acid having 18 or 20 carbon atoms or a fatty acid ester compound thereof, more preferably an oleic acid, a linoleic acid, an α-linolenic acid, a γ-linolenic acid, a stearidonic acid, a dihomo-γ-linolenic acid, an eicosatetraenoic acid, an arachidonic acid or an eicosapentaenoic acid, or a fatty acid ester compound thereof, more preferably an oleic acid, an arachidonic acid or an eicosapentaenoic acid, or a fatty acid ester compound thereof, and more preferably an arachidonic acid or an eicosapentaenoic acid, or a fatty acid ester compound thereof.

<40> The method described in any one of the above items <1> to <39>, wherein the alga is cultured by using f/2 media.

<41> The proteins (A) to (C) and (C1).

<42> A gene encoding the protein described in the above item <41>.

<43> A gene consisting of any one of the DNAs (a) to (c) and (c1).

<44> A recombinant vector or a DNA cassette, containing the gene described in the above item <42> or <43>.

<45> A transformant containing the gene, the recombinant vector, or the DNA cassette described in any one of the above items <42> to <44>.

<46> A transformant wherein the expression of the gene described in the above item <42> or <43>

<47> The transformant described in the item <45> or <46>, wherein the expression of the KAS is enhanced.

<48> The transformant described in any one of the items <45> to <47>, wherein the expression of the desaturase gene is enhanced.

<49> The transformant described in any one of the items <45> to <48>, wherein the expression of the elongase gene is enhanced.

<50> The transformant described in any one of the items <45> to <49>, wherein the expression of the TE gene is enhanced.

<51> A method of preparing a transformant containing the steps of introducing the gene, the recombinant vector, or the DNA cassette described in any one of the above items <42> to <44> thereinto.

<52> The method of preparing a transformant described in the item <51>, wherein the KAS gene is introduced.

<53> The method of preparing a transformant described in the item <51> or <52>, wherein the desaturase gene is introduced.

<54> The method of preparing a transformant described in any one of the items <51> to <53>, wherein the elongase gene is introduced.

<55> The method of preparing a transformant described in any one of the items <51> to <54>, wherein the TE gene is introduced.

<56> The transformant or the method of preparing the same described in any one of the above items <45> to <55>, wherein the transformant is a transformant of microorganism.

<57> The transformant or the method of preparing the same described in the above item <56>, wherein the microorganism is a microalga.

<58> The transformant or the method of preparing the same described in the above item <57>, wherein the microalga is an alga belonging to the genus *Nannochloropsis*.

<59> The transformant or the method of preparing the same described in the above item <57> or <58>, wherein the microalga is selected from the group consisting of *Nannochloropsis oculata*, *Nannochloropsis gaditana*, *Nannochloropsis salina*, *Nannochloropsis oceanica*, *Nannochloropsis atomus*, *Nannochloropsis maculata*, *Nannochloropsis granulata*, and *Nannochloropsis* sp., preferably selected from the group consisting of *Nannochloropsis oculata* and *Nannochloropsis gaditana*, or more preferably *Nannochloropsis oculata*.

<60> The transformant or the method of preparing the same described in the above item <56>, wherein the microorganism is *Escherichia coli*.

<61> Use of the protein, the gene, the recombinant vector or the DNA cassette, the transformant, or the method of preparing the same described in any one of the above items <41> to <60>, for producing lipids.

<62> The use described in the above item <61>, wherein the lipids contain a long-chain fatty acid or a fatty acid ester compound thereof, preferably a fatty acid having 18 or more carbon atoms or a fatty acid ester compound thereof, more preferably a fatty acid having 18 or 20 carbon atoms or a fatty acid ester compound thereof, more preferably an unsaturated fatty acid having 18 or 20 carbon atoms or a fatty acid ester compound thereof, more preferably an oleic acid, a linoleic acid, an α-linolenic acid, a γ-linolenic acid, a stearidonic acid, a dihomo-γ-linolenic acid, an eicosatetraenoic acid, an arachidonic acid or an eicosapentaenoic acid, or a fatty acid ester compound thereof, more preferably an oleic acid, an arachidonic acid or an eicosapentaenoic acid, or a fatty acid ester compound thereof, and more preferably an arachidonic acid or an eicosapentaenoic acid, or a fatty acid ester compound thereof.

EXAMPLES

Hereinafter, the present invention will be described more in detail with reference to Examples, but the present invention is not limited thereto. Herein, the nucleotide sequences of the primers used in Examples are shown in Table 1.

TABLE 1

| Primer No. | Nucleotide sequence (5'→3') | SEQ ID NO |
|---|---|---|
| 5 | CTTTTTTGTGAAGCAATGGCCAAGTTGACCAGTGCCG | SEQ ID NO: 5 |
| 6 | TTTCCCCCATCCCGATTAGTCCTGCTCCTCGGCCAC | SEQ ID NO: 6 |
| 7 | CGAGCTCGGTACCCGACTGCGCATGGATTGACCGA | SEQ ID NO: 7 |
| 8 | TGCTTCACAAAAAAGACAGCTTCTTGAT | SEQ ID NO: 8 |
| 9 | TCGGGATGGGGGAAAAAAACCTCTG | SEQ ID NO: 9 |
| 10 | ACTCTAGAGGATCCCCTTTCGTAAATAAATCAGCTC | SEQ ID NO: 10 |
| 12 | GGGATCCTCTAGAGTCGACC | SEQ ID NO: 12 |
| 13 | CGGGTACCGAGCTCGAATTC | SEQ ID NO: 13 |
| 14 | CAGCCCGCATCAACAATGGCTCTCCGTCAATTTCTG | SEQ ID NO: 14 |
| 15 | CTCTTCCACAGAAGCTTATTTTGCCTGGGGATGGG | SEQ ID NO: 15 |
| 16 | CGAGCTCGGTACCCGTTCTTCCGCTTGTTGCTGCC | SEQ ID NO: 16 |
| 17 | TGTTGATGCGGGCTGAGATTGGTGG | SEQ ID NO: 17 |
| 18 | GCTTCTGTGGAAGAGCCAGTG | SEQ ID NO: 18 |
| 19 | GGCAAGAAAAGCTGGGGAAAAGACAGG | SEQ ID NO: 19 |
| 22 | CCAGCTTTTCTTGCCACTGCGCATGGATTGACCGA | SEQ ID NO: 22 |
| 23 | CAGCCCGCATCAACAATGAAGACCGCCGCTCTCCTC | SEQ ID NO: 23 |
| 24 | GCGCGCAACACCGCGGGTGCGGGAGAAC | SEQ ID NO: 24 |
| 26 | CGCGGTGTTGCGCGCATCATGACAGTCGCTCGTCGAG | SEQ ID NO: 26 |
| 62 | CAGCCCGCATCAACAATGGTCTTCCAGCTCGCCCG | SEQ ID NO: 62 |
| 63 | CTCTTCCACAGAAGCTTAGTTGTACTTGGGGTGATTGC | SEQ ID NO: 63 |
| 64 | CAGCCCGCATCAACAATGGGACGCGGCGGTGAGAA | SEQ ID NO: 64 |
| 65 | CTCTTCCACAGAAGCCTATGCCCGCTGCTTGTAGA | SEQ ID NO: 65 |
| 66 | CAGCCCGCATCAACAATGGGACGCGGTGGCGAGCG | SEQ ID NO: 66 |
| 67 | CTCTTCCACAGAAGCTTACATGGCGGGGAAATCGG | SEQ ID NO: 67 |
| 68 | CAGCCCGCATCAACAATGGTTGAGCAAACGTTACC | SEQ ID NO: 68 |
| 69 | CTCTTCCACAGAAGCTTACGGAGGGGAGGATGAAC | SEQ ID NO: 69 |
| 71 | CTTTTTTGTGAAGCAATGGTCGAGATTCGAAGCAT | SEQ ID NO: 71 |
| 72 | TTTCCCCCATCCCGATCAGAAGAACTCGTCCAACA | SEQ ID NO: 72 |
| 73 | TGCTTCACAAAAAAGACAGCTTCTTGAT | SEQ ID NO: 73 |
| 74 | TCGGGATGGGGGAAAAAAACCTCTG | SEQ ID NO: 74 |
| 75 | CGAGCTCGGTACCCGGTGTGTCCTGCGTGTTGATCAGTAG | SEQ ID NO: 75 |
| 76 | TTTTAGGGGGTGGTCGAGTTGCTGTGGTG | SEQ ID NO: 76 |
| 77 | GAAAGATCCAAGAGAGACGAGTAG | SEQ ID NO: 77 |

TABLE 1-continued

| Primer No. | Nucleotide sequence (5'→3') | SEQ ID NO |
|---|---|---|
| 78 | AGGACCGAATCGAGGCTCTGATAAATGAGG | SEQ ID NO: 78 |
| 81 | CCTCGATTCGGTCCTTTCTTCCGCTTGTTGCTGCCGATG | SEQ ID NO: 81 |
| 82 | GACCACCCCCTAAAAATGGTCTTCCAGCTCGCCCGAG | SEQ ID NO: 82 |
| 83 | TCTCTTGGATCTTTCTTAGTTGTACTTGGGGTGATTGC | SEQ ID NO: 83 |
| 84 | GACCACCCCCTAAAAATGGTTGAGCAAACGTTACCGAC | SEQ ID NO: 84 |
| 85 | TCTCTTGGATCTTTCTTACGGAGGGGAGGATGAACGG | SEQ ID NO: 85 |
| 86 | GACCACCCCCTAAAAATGGGACGCGGTGGCGAGCGGGTC | SEQ ID NO: 86 |
| 87 | TCTCTTGGATCTTTCTTACATGGCGGGGAAATCGGCCAC | SEQ ID NO: 87 |
| 88 | GTGTGTCCTGCGTGTTGATCAGTAGATGCGCAAG | SEQ ID NO: 88 |

Comparative Example Preparation of a Transformant in which a NoACP1 Gene is Introduced into *Nannochloropsis oculata* and Production of Lipids by the Transformant (1) Construction of Plasmid for Zeocin Resistance Gene Expression A zeocin resistance gene (SEQ ID NO: 3), and a tubulin promoter sequence (SEQ ID NO: 4) derived from *Nannochloropsis gaditana* strain CCMP 526 described in a literature (Nature Communications, DOI:10.1038/ncomms1688, 2012) were artificially synthesized. Using the thus-synthesized DNA fragments as a template, and a pair of the primer Nos. 5 and 6, and a pair of the primer Nos. 7 and 8 shown in Table 1, PCRs were carried out, to amplify the zeocin resistance gene and the tubulin promoter sequence, respectively.

Further, using a genome of *Nannochloropsis oculata* strain NIES-2145 (obtained from National Institute for Environmental Studies (NIES)) as a template, and a pair of the primer Nos. 9 and 10 shown in Table 1, PCR was carried out to amplify the heat shock protein terminator sequence (SEQ ID NO: 11).

Furthermore, using a plasmid vector pUC19 (manufactured by Takara Bio) as a template, and a pair of the primer Nos. 12 and 13 shown in Table 1, PCR was carried out to amplify the plasmid vector pUC19.

These four amplified fragments were treated by restriction enzyme DpnI (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for zeocin resistance gene expression.

Herein, the expression plasmid consisted of the pUC19 vector sequence and an insert sequence in which the tubulin promoter sequence, the zeocin resistance gene and the heat shock protein terminator sequence were linked in this order.

(2) Obtainment of NoACP1 Gene, and Construction of Plasmid for NoACP1 Gene Expression Total RNA of *Nannochloropsis oculata* strain NIES-2145 was extracted. The cDNA was obtained by reverse transcription using the total RNA and SuperScript (trademark) III First-Strand Synthesis SuperMix for qRT-PCR (manufactured by invitrogen). Using a pair of the primer Nos. 14 and 15 shown in Table 1 and the above cDNA as a template, PCR was carried out to obtain a gene fragment (NoACP1 gene) consisting of the nucleotide sequence set forth in SEQ ID NO: 2

Further, using a genome of *Nannochloropsis oculata* strain NIES-2145 as a template, and a pair of the primer Nos. 16 and 17, and a pair of the primer Nos. 18 and 19 shown in Table 1, respectively, PCRs were carried out to obtain the LDSP promoter sequence (SEQ ID NO: 20), and the VCP1 terminator sequence (SEQ ID NO: 21).

Furthermore, using the plasmid for zeocin resistance gene expression as a template, and a pair of the primer Nos. 22 and 13 shown in Table 1, PCR was carried out to amplify a fragment containing the cassette for zeocin resistance gene expression (the tubulin promoter sequence, the zeocin resistance gene, and the heat shock protein terminator sequence) and the pUC19 sequence.

The NoACP1 gene fragment was mixed with the LDSP promoter fragment, the VCP1 terminator fragment, and the fragment containing the cassette for the zeocin resistance gene expression and the pUC19 sequence. Then, these four fragments were fused by a method in a manner similar to that described above, to construct a plasmid for the NoACP1 gene expression.

Herein, the expression plasmid consisted of the pUC19 vector sequence and an insert sequence in which the LDSP promoter sequence, the NoACP1 gene, the VCP1 terminator sequence, the tubulin promoter sequence, the zeocin resistance gene and the heat shock protein terminator sequence were linked in this order.

(3) Introduction of a Cassette for NoACP1 Gene Expression into *Nannochloropsis oculata*

Using the above-described plasmid for the NoACP1 gene expression as a template, and a pair of the primer Nos. 10 and 16 shown in Table 1, PCR was carried out to amplify the cassette for NoACP1 gene expression (a DNA fragment containing the LDSP promoter sequence, the NoACP1 gene, the VCP1 terminator sequence, the tubulin promoter sequence, the zeocin resistance gene, and the heat shock protein terminator sequence).

The amplified DNA fragment was purified using High Pure PCR Product Purification Kit (manufactured by Roche Applied Science). Herein, sterilized water was used for elution upon purification without using an elution buffer included in the kit.

About $1 \times 10^9$ cells of *Nannochloropsis oculata* strain NIES-2145 were washed with 384 mM sorbitol solution to completely remove a salt, and the resultant was used as a host cell for transformation. The cassette for the NoACP1 gene expression as amplified above was mixed by about 500 ng with the host cell, and electroporation was carried out under the conditions of 50 µF, 500Ω and 2,200 v/2 mm.

After 24 hours recovery cultivation in f/2 liquid medium (75 mg of $NaNO_3$, 6 mg of $NaH_2PO_4.2H_2O$, 0.5 µg of vitamin B12, 0.5 µg of biotin, 100 µg of thiamine, 10 mg of $Na_2SiO_3.9H_2O$, 4.4 mg of $Na_2EDTA.2H_2O$, 3.16 mg of $FeCl_3.6H_2O$, 12 µg of $FeCl_3.6H_2O$, 21 µg of $ZnSO_4.7H_2O$, 180 µg of $MnCl_2.4H_2O$, 7 µg of $CuSO_4.5H_2O$, 7 µg of $Na_2MoO_4.2H_2O$/artificial sea water 1 L), the resultant was inoculated in f/2 agar medium containing 2 µg/mL of zeocin, and cultured for two to three weeks under 12 h/12 h light-dark conditions at 25° C. under an atmosphere of 0.3% $CO_2$. A transformant of *Nannochloropsis oculata* strain containing the cassette for the NoACP1 gene expression was selected from the resultant colonies by a PCR method.

(4) Production of Fatty Acid by Transformant Containing NoACP1 Gene

The selected strain was inoculated to 20 mL of medium in which a nitrogen concentration in the f/2 medium was reinforced 15 times, and a phosphorus concentration therein was reinforced 5 times (hereinafter, referred to as "N15P5 medium"), and subjected to shaking culture for three to four weeks under the 12 h/12 h light-dark conditions at 25° C. under the atmosphere of 0.3% $CO_2$, to prepare preculture fluid. Then, the preculture fluid of the each three independent lines was inoculated to the medium (10% of inoculation), in which a nitrogen concentration in the f/2 medium was reinforced 30 times, and a phosphorus concentration therein was reinforced 30 times (hereinafter, referred to as "N30P30 medium"), and subjected to shaking culture for 11 days under the 12 h/12 h light-dark conditions at 25° C. under the atmosphere of 0.3% $CO_2$. In addition, as a negative control, an experiment was also conducted on *Nannochloropsis oculata* strain NIES-2145 being wild type strain.

(5) Extraction of Lipid and Analysis of Fatty Acids

To 0.5 mL of the culture fluid, 50 µL of 1 mg/mL glyceryl triheptadecanoate (manufactured by Sigma-Aldrich)/chloroform solution was added as an internal standard, and then 0.5 mL of chloroform and 1 mL of methanol were further added. The mixture was vigorously stirred and then was left for 10 minutes. Further, 0.5 mL of chloroform and 0.5 mL of 1.5% KCl were added thereto. The mixture was stirred and centrifuged for 5 minutes at 3,000 rpm, and then the chloroform layer (lower layer) was collected by Pasteur pipette.

A nitrogen gas was blown onto the resultant chloroform layer to be dried into solid. Then, 0.7 mL of 0.5N potassium hydroxide (methanol solution) was added thereto, and the mixture was kept warm at 80° C. for 30 minutes. Further, 1 mL of 14% boron trifluoride-methanol solution (manufactured by Sigma-Aldrich) was added to the sample, and the mixture was kept warm at 80° C. for 10 minutes. Thereafter, 0.5 mL of hexane and 1 mL of saturated saline were added thereto, and the mixture was vigorously stirred and then was left for 10 minutes at room temperature. Then, the hexane layer being an upper layer was collected to obtain fatty acid esters.

Under the measuring conditions as follows, the obtained fatty acid esters were provided for gas chromatographic analysis.

<Gas Chromatography Conditions>

Analysis apparatus: 7890A (manufactured by Agilent Technologies)
Capillary column: DB-1 MS (30 m×200 µm×0.25 µm, manufactured by J&W Scientific)
Mobile phase: high purity helium
Oven temperature: maintained for 0.5 minutes at 150° C.→150 to 220° C. (temperature increase at 40° C./minute) →220 to 320° C. (temperature increase at 20° C./minute) →maintained for 2 minutes at 320° C. (post run: 2 minutes)
Injection port temperature: 300° C.
Injection method: split injection (split ratio: 75:1)
Amount of injection: 1 µL
Cleaning vial: methanol/chloroform
Detection method: FID
Detector temperature: 300° C.

The fatty acid esters were identified by providing the identical sample for gas chromatography-mass spectrometry analysis under identical conditions described above.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of fatty acid methyl esters having 17 carbon atoms derived from glyceryl triheptadecanoate being the internal standard, and carried out corrections between the samples, and then the amount of each of the fatty acids per liter of the culture fluid was calculated. Further, the total amount of the fatty acids was calculated by summing the amounts of each of the fatty acids thus obtained, and proportion of each of the fatty acids in the total amount of the fatty acids was calculated.

Table 2 shows the results. Herein, in Table below, "TFA" presents the amount of total fatty acid, and "Fatty Acid Composition (% TFA)" presents a proportion of a weight of each fatty acid relative to a weight of the total fatty acid. Further, "n" designates an integer of 0 to 5. For example, when "C18:n" is described, the description means all of each fatty acid having compositions of C18:0, C18:1, C18:2, C18:3, C18:4 and C18:5.

TABLE 2

| | | TFA | Fatty Acid Composition (% TFA) | | | | | |
|---|---|---|---|---|---|---|---|---|
| | line | (mg/L) | C12:0 | C14:0 | C16:1 | C16:0 | C18:n | C20:n |
| NIES2145 | 1 | 736.6 | 0.23 | 4.0 | 27.7 | 35.2 | 16.5 | 16.3 |
| (reference example) | 2 | 610.2 | 0.25 | 4.0 | 27.7 | 33.9 | 16.4 | 17.7 |
| | 3 | 730.2 | 0.24 | 4.1 | 28.3 | 34.5 | 16.4 | 16.5 |
| NoACP1 gene | 1 | 859.2 | 0.26 | 4.2 | 30.2 | 33.1 | 15.4 | 16.8 |
| transgenic strain | 2 | 670.9 | 0.25 | 4.2 | 30.3 | 33.2 | 15.0 | 17.1 |
| (comparative example) | 3 | 618.9 | 0.25 | 4.0 | 29.5 | 33.1 | 14.7 | 18.4 |

As is apparent from Table 2, in the algae into which the cassette for NoACP1 gene expression was introduced (NoACP1 gene transgenic strain), no significant change was found in all of the amount of long-chain fatty acids, the amount of the total fatty acids, and the fatty acid composition in comparison with those in the wild type strain (NIES2145).

Example 1 Preparation of a Transformant Wherein the Chloroplast Transit Signal Linked NoACP1(Δ1-22) Gene was Introduced into *Nannochloropsis oculata*, and Production of Lipids by the Transformant (1) Prediction of Subcellular Localization of NoACP1

The subcellular localization prediction site TargetP was used to predict where the NoACP1 is localized in vivo.

As a result, it was suggested at a high score (0.943) that the NoACP1 is localized in mitochondria. Then, it was estimated that an amino acid sequence of $1^{st}$ to $22^{nd}$ amino acids of the amino acid sequence set forth in SEQ ID NO: 1 is the amino acid sequence of a mitochondrial localization signal.

(2) Construction of Plasmid for Chloroplast Transit Signal Linked NoACP1(Δ1-22) Gene Expression Using the cDNA derived from *Nannochloropsis oculata* strain NIES-2145 prepared in Comparative Example as a template, and a pair of the primer Nos. 23 and 24 shown in Table 1, PCR was carried out to obtain the VCP1 chloroplast transit signal fragment consisting of the nucleotide sequence set forth in SEQ ID NO: 25.

Furthermore, using the plasmid for the NoACP1 gene expression prepared in Comparative Example as a template, and a pair of the primer Nos. 26 and 17 shown in Table 1, PCR was carried out to obtain a DNA fragment containing the NoACP1(Δ1-22) gene which was deleted the mitochondrial localization signal, the VCP1 terminator sequence, the tubulin promoter sequence, the zeocin resistance gene, the heat shock protein terminator sequence, and the LDSP promoter sequence.

The obtained DNA fragment and the VCP1 chloroplast transit signal fragment were linked by a method in a manner similar to that in Comparative Example, and a plasmid for the chloroplast transit signal linked NoACP1(Δ1-22) gene expression was constructed. Note that, the expression plasmid consisted of the pUC19 vector sequence and an insert sequence in which the LDSP promoter sequence, the VCP1 chloroplast transit signal sequence, the NoACP1(Δ1-22) gene which was deleted the mitochondrial localization signal (the nucleotide sequence of the $67^{th}$ to $441^{st}$ nucleotides set forth in SEQ ID NO: 2), the VCP1 terminator sequence, the tubulin promoter sequence, the zeocin resistance gene and the heat shock protein terminator sequence were linked in this order.

In addition, it is shown in Protist, 2015, vol. 166 (1), pp. 161-171 that the VCP1 chloroplast transit signal can make a protein to localize in the chloroplast in a cell of *Nannochloropsis*.

(3) Introduction of a Cassette for the Chloroplast Transit Signal Linked NoACP1(Δ1-22) Gene Expression into *Nannochloropsis oculata*

Using the constructed plasmid for the chloroplast transit signal linked NoACP1(Δ1-22) gene expression as a template, and a pair of the primer Nos. 10 and 16 shown in Table 1, PCR was carried out to amplify the cassette for the chloroplast transit signal linked NoACP1(Δ1-22) gene expression (a DNA fragment containing the LDSP promoter sequence, the VCP1 chloroplast transit signal sequence, the NoACP1(Δ1-22) gene which was deleted the mitochondrial localization signal, the VCP1 terminator sequence, the tubulin promoter sequence, the zeocin resistance gene, and the heat shock protein terminator sequence). The amplified fragments were purified by a method in a manner similar to that in Comparative Example, and then, transformation of *Nannochloropsis oculata* strain NIES-2145 was carried out by a method in a manner similar to that in Comparative Example by using the purified fragments.

(4) Production of Fatty Acid by the Transformant into which the Chloroplast Transit Signal Linked NoACP1 (Δ1-22) Gene was Introduced, Extraction of Lipid, and Analysis of Fatty Acids Contained Therein The selected strain was inoculated to medium in which a nitrogen concentration in the f/2 medium was reinforced 5 times, and a phosphorus concentration therein was reinforced 5 times (hereinafter, referred to as "N5P5 medium"), and subjected to shaking culture for three weeks under the 12 h/12 h light-dark conditions at 25° C. under the atmosphere of 0.3% $CO_2$, to prepare preculture fluid. Then, the obtained preculture fluid was inoculated to N5P5 medium (10% of inoculation), and subjected to shaking culture for 14 days under the 12 h/12 h light-dark conditions at 25° C. under the atmosphere of 0.3% $CO_2$. In addition, as a negative control, an experiment was also conducted on *Nannochloropsis oculata* strain NIES-2145 being wild type strain.

Using the obtained culture fluid, the lipid extraction and analysis of fatty acid components were performed by a method in a manner similar those in Comparative Example. Table 3 shows the results.

TABLE 3

| | | TFA | Fatty Acid Composition (% TFA) | | | | | |
|---|---|---|---|---|---|---|---|---|
| | line | (mg/L) | C12:0 | C14:0 | C16:1 | C16:0 | C18:n | C20:n |
| NIES2145 (reference example) | 1 | 1315.1 | 0.0 | 5.0 | 28.8 | 42.2 | 15.2 | 8.8 |
| | 2 | 1192.1 | 0.0 | 4.7 | 29.3 | 41.8 | 14.7 | 9.4 |
| Svcp1-NoACP1(Δ1-22) (present invention example) | 1 | 1231.6 | 0.0 | 1.6 | 12.4 | 42.5 | 31.5 | 12.1 |
| | 2 | 1113.4 | 0.0 | 1.7 | 10.8 | 41.5 | 32.6 | 13.4 |
| | 3 | 1167.9 | 0.0 | 1.7 | 10.6 | 41.3 | 33.6 | 12.9 |

As shown in Table 3, in the transformant (Svcp1-NoACP1 (Δ1-22)) into which the cassette for the chloroplast transit signal linked NoACP1(Δ1-22) gene expression was introduced, significant change of the fatty acid composition was confirmed in comparison with that in the wild type strain (NIES-2145). Specifically, proportions of medium-chain fatty acids, especially C14:0 and C16:1, were largely reduced. Then, proportions of long-chain fatty acids (C18:n and C20:n) were significantly increased.

(5) Detailed Analysis of Fatty Acid Produced by the Transformant into which the Chloroplast Transit Signal Linked NoACP1(Δ1-22) Gene was Introduced The transformant into which the chloroplast transit signal linked NoACP1(Δ1-22) gene was introduced and the wild type strain (NIES-2145) were cultured for 14 days under the conditions similar to the above-described conditions, and then lipids were extracted. Then, under the measuring conditions as follows, the obtained fatty acid esters were provided for gas chromatographic analysis. Table 4 shows the results. In addition, in Table 4, "C20:n" represents a total of the proportions of the fatty acids C20:3, C20:4 and C20:5.
<Gas Chromatography Conditions>
Analysis apparatus: 7890A (manufactured by Agilent Technologies)
Capillary column: DB-WAX (10 m×100 μm×0.10 μm, manufactured by J&W Scientific)
Mobile phase: high purity helium
Oven temperature: maintained for 0.5 minutes at 100° C.→100 to 250° C. (temperature increase at 20° C./minute) →maintained for 3 minutes at 250° C.
(post run: 1 minute)
Injection port temperature: 300° C.
Injection method: split injection (split ratio: 50:1)
Amount of injection: 5 μL
Cleaning vial: methanol
Detection method: FID
Detector temperature: 350° C.

sequence, the tubulin promoter sequence, the zeocin resistance gene and the heat shock protein terminator sequence were linked in this order.
(2) Construction of Plasmid for Desaturase Gene Expression (Paromomycin Resistance)
Using the paromomycin resistance gene (SEQ ID NO: 70) artificially synthesized as a template, and a pair of the primer Nos. 71 and 72 shown in Table 1, PCR was carried out to obtain the paromomycin resistance gene fragment.
Further, using the plasmid for each desaturase gene expression as a template, and a pair of the primer Nos. 73 and 74 shown in Table 1, PCRs were carried out. The each obtained fragment and the paromomycin resistance gene fragment were fused by a method in a manner similar to that in Comparative Example, and plasmids for each desaturase gene expression (paromomycin resistance) were constructed.
Herein, the expression plasmid consisted of the pUC19 vector sequence and an insert sequence in which the LDSP promoter sequence, the each desaturase (Δ9-DES, Δ12-DES, Δ6-DES, or ω3-DES) gene, the VCP1 terminator sequence,

TABLE 4

| | | Fatty Acid Composition (% TFA) | | | | | | | | | | |
|---|---|---|---|---|---|---|---|---|---|---|---|---|
| | TFA (mg/L) | C14:0 | C16:0 | C16:1 (Δ9) | C18:0 | C18:1 (Δ9) | C18:2 (Δ9, 12) | C18:3 | C20:3 | C20:4 | C20:5 | C20:n |
| NIES2145 (reference example) | 1189.4 | 5.2 | 42.3 | 28.9 | 1.7 | 12.2 | 1.0 | 0.3 | 0.3 | 2.1 | 6.0 | 8.4 |
| Svcp1-NoACP1(Δ1-22) (present invention example) | 1080.3 | 1.6 | 37.8 | 10.6 | 2.2 | 31.6 | 1.9 | 1.3 | 0.3 | 3.4 | 9.3 | 13.0 |

As shown in Table 4, in the transformant into which the cassette for the chloroplast transit signal linked NoACP1 (Δ1-22) gene expression was introduced, proportions of long-chain fatty acids in the whole fatty acids and production amount of long-chain fatty acids were increased in comparison with those in the wild type strain (NIES-2145). Especially, among them, proportions of the amount of C18:1(Δ9) (oleic acid), the amount of C20:4(Δ5,8,11,14) (arachidonic acid), and the amount of C20:5(Δ5,8,11,14,17) (eicosapentaenoic acid) were significantly increased.

Example 2 Preparation of a Transformant Wherein the NoACP1(Δ1-22) Gene and the Desaturase Gene were Introduced into Nannochloropsis oculata, and Production of Lipids by the Transformant (1) Obtainment of Desaturase Gene
Using the cDNA of Nannochloropsis oculata strain NIES-2145 prepared in Comparative Example as a template, and pairs of the primer Nos. 62 and 63, the primer Nos. 64 and 65, the primer Nos. 66 and 67, and the primer Nos. 68 and 69, shown in Table 1, PCRs were carried out to amplify the Δ9-DES gene (SEQ ID NO: 48), the Δ12-DES gene (SEQ ID NO: 40), the Δ6-DES gene (SEQ ID NO: 42), and the ω3-DES gene (SEQ ID NO: 44), respectively. The each obtained fragment was linked with the plasmid vector pUC19 by a method in a manner similar to that in Comparative Example, and plasmids for desaturase gene expression were constructed.
Herein, these expression plasmids consisted of the pUC19 vector sequence and an insert sequence in which the LDSP promoter sequence, the each desaturase gene (Δ9-DES, Δ12-DES, Δ6-DES, or ω3-DES), the VCP1 terminator sequence, the tubulin promoter sequence, the paromomycin resistance gene and the heat shock protein terminator sequence were linked in this order.
(3) Construction of a Plasmid (Paromomycin Resistance) for Two Types of Desaturase Genes Expressions.
Using the genome of Nannochloropsis oculata strain NIES-2145 as a template, and a pair of the primer Nos. 75 and 76, and a pair of the primer Nos. 77 and 78, shown in Table 1, PCRs were carried out to amplify the fragment of a glutamine synthetase promoter (SEQ ID NO: 79), and the fragment of a LDSP terminator (SEQ ID NO: 80).
Further, using the plasmid for the Δ9-DES gene expression, the plasmid for the ω3-DES gene expression, and the plasmid for the Δ6-DES gene expression as templates respectively, and a pair of the primer Nos. 82 and 83, a pair of the primer Nos. 84 and 85, and a pair of the primer Nos. 86 and 87, shown in Table 1, PCRs were carried out to obtain the Δ9-DES gene fragment, the ω3-DES gene fragment, and the Δ6-DES gene fragment.
Furthermore, using the plasmid for the Δ12-DES gene expression (paromomycin resistance) as a template, and a pair of the primer Nos. 81 and 13 shown in Table 1, PCR was carried out. The obtained amplified fragment, the glutamine synthetase promoter fragment, LDSP terminator fragment, and desaturase gene fragment (Δ9-DES gene fragment, ω3-DES gene fragment, or Δ6-DES gene fragment) were fused respectively, and a plasmid for two types of desaturase genes expressions was constructed.
Herein, the expression plasmid consisted of the pUC19 vector sequence and an insert sequence in which the glutamine synthetase promoter sequence, the each desaturase (Δ9-DES, ω3-DES, or Δ6-DES) gene, the LDSP terminator sequence, the Δ12-DES gene, the VCP1 terminator sequence, the tubulin promoter sequence, the paromomycin resistance gene and the heat shock protein terminator sequence were linked in this order.

(4) Transformation of Svcp1-NoACP1 (Δ1-22) Strain Using Desaturase Gene

Using the plasmid for desaturase gene expression constructed as a template, and a pair of the primer Nos. 10 and 16 shown in Table 1, PCR was carried out to amplify the cassette for desaturase gene expression (a DNA fragment containing the LDSP promoter sequence, the desaturase (Δ9-DES, Δ12-DES, or ω3-DES) gene, the VCP1 terminator sequence, the tubulin promoter sequence, the paromomycin resistance gene, and the heat shock protein terminator sequence).

The amplified fragments were purified by a method in a manner similar to that in Comparative Example, and then, transformation of the Svcp1-NoACP1(Δ1-22) strain prepared in Example 1 was performed by a method in a manner similar to that in Comparative Example by using the purified fragments.

Further, using the plasmid (paromomycin resistance) for two types of desaturase genes expressions as a template, and a pair of the primer Nos. 10 and 88 shown in Table 1, PCR was carried out to amplify a cassette for two types of desaturase genes expressions (a DNA fragment containing the glutamine synthetase promoter sequence, the desaturase (Δ9-DES, ω3-DES, or Δ6-DES) gene, the LDSP terminator sequence, the LDSP promoter sequence, the M2-DES gene, the VCP1 terminator sequence, the tubulin promoter sequence, the paromomycin resistance gene, and the heat shock protein terminator sequence).

The amplified fragments were purified by a method in a manner similar to that in Comparative Example, and then, transformation of the Svcp1-NoACP1(Δ1-22) strain constructed in Example 1 was carried out by a method in a manner similar to that in Comparative Example by using the purified fragments.

Recovery cultivation was carried out according to the same method as in Comparative Example, and then the resultant was applied onto an f/2 agar medium containing 2 μg/mL of zeocin and 100 μg/mL of paromomycin, and cultured for two to three weeks under the 12 h/12 h light-dark conditions at 25° C. under an atmosphere of 0.3% $CO_2$. From the resultant colonies, the transformants including various cassettes for desaturase gene expression were each selected by 3 to 4 lines. Hereinafter, the obtained transformants are cited as; a Svcp1-NoACP1(Δ1-22) gene and a Δ9-DES gene transgenic strain (Svcp1-NoACP1(Δ1-22)+delta9 DES), a Svcp1-NoACP1(Δ1-22) gene and a Δ12-DES gene transgenic strain (Svcp1-NoACP1(Δ1-22)+delta12 DES), a Svcp1-NoACP1(Δ1-22) gene and an ω3-DES gene transgenic strain (Svcp1-NoACP1(Δ1-22)+omega3 DES), a Svcp1-NoACP1(Δ1-22) gene, a Δ12-DES gene and a Δ9-DES gene transgenic strain (Svcp1-NoACP1(Δ1-22)+delta12 DES+delta9 DES), a Svcp1-NoACP1(Δ1-22) gene, a Δ12-DES gene, and a Δ6-DES gene transgenic strain (Svcp1-NoACP1(Δ1-22)+delta12 DES+delta6 DES), and a Svcp1-NoACP1(Δ1-22) gene, Δ12-DES gene, and an ω3-DES gene transgenic strain (Svcp1-NoACP1(Δ1-22)+delta12 DES+omega3 DES), respectively.

(5) Culture of Transformant, Extraction of Lipids and Analysis of Fatty Acids Contained Therein The selected strain was inoculated to 4 mL of the N15P5 medium (Microplate for Tissue Culture, manufactured by IWAKI), and subjected to shaking culture for three to four weeks under the 12 h/12 h light-dark conditions at 25° C. under the atmosphere of 0.3% $CO_2$, to prepare preculture fluid. Then, 0.4 mL of the preculture fluid was inoculated to 4 mL of the N5P5 medium (Microplate for Tissue Culture, manufactured by IWAKI), and subjected to shaking culture for three weeks under the 12 h/12 h light-dark conditions at 25° C. under the atmosphere of 0.3% $CO_2$. In addition, as negative controls, the wild type strain and Svcp1-NoACP1 (Δ1-22) strain were also subjected to the same experiment.

Using the obtained culture fluid, extraction of lipids and analysis of fatty acids contained therein were carried out, according to the same method as in Comparative Example. The results of production amount of total fatty acids and the fatty acid composition in the third week are shown in Table 5. Herein, the independent three to four lines per the each transformant were evaluated, and the Table 5 shows the average value and standard error thereof, in the form of "average value±standard error".

TABLE 5

| | TFA (mg/L) | Fatty Acid Composition (% TFA) | | | | | | |
|---|---|---|---|---|---|---|---|---|
| | | C14:0 | C16:0 | C16:1 (Δ9) | C18:0 | C18:1 (Δ9) | C18:1 (Δ11) | C18:2 (Δ6, 9) |
| WT (reference example) | 1000.1 ± 18.9 | 3.9 ± 0.1 | 33.5 ± 0.2 | 29.7 ± 0.0 | 1.7 ± 0.0 | 16.6 ± 0.0 | 0.0 ± 0.0 | 0.2 ± 0.0 |
| Svcp1-NoACP1(Δ1-22) | 1209.3 ± 99.8 | 2.1 ± 0.0 | 31.0 ± 0.5 | 12.1 ± 0.2 | 1.4 ± 0.1 | 30.6 ± 0.3 | 0.0 ± 0.0 | 0.3 ± 0.0 |
| Svcp1-NoACP1(Δ1-22) + delta9-DES | 1249.1 ± 258.2 | 1.8 ± 0.1 | 25.5 ± 1.0 | 13.6 ± 0.9 | 0.8 ± 0.1 | 42.9 ± 1.7 | 0.0 ± 0.0 | 0.2 ± 0.1 |
| Svcp1-NoACP1(Δ1-22) + delta12-DES | 1365.4 ± 196.7 | 1.7 ± 0.1 | 39.4 ± 1.9 | 12.9 ± 0.1 | 1.7 ± 0.2 | 18.3 ± 1.1 | 0.0 ± 0.0 | 0.0 ± 0.0 |
| Svcp1-NoACP1(Δ1-22) + omega3-DES | 1682.5 ± 20.0 | 1.7 ± 0.0 | 30.6 ± 0.6 | 12.2 ± 0.1 | 1.3 ± 0.0 | 32.7 ± 0.3 | 0.0 ± 0.0 | 0.3 ± 0.0 |
| Svcp1-NoACP1(Δ1-22) + delta12-DES + delta9-DES | 1821.1 ± 84.9 | 1.8 ± 0.0 | 29.8 ± 1.1 | 11.9 ± 0.2 | 1.1 ± 0.1 | 24.5 ± 1.0 | 0.0 ± 0.0 | 0.0 ± 0.0 |
| Svcp1-NoACP1(Δ1-22) + delta12-DES + delta6-DES | 1862.2 ± 135.5 | 1.8 ± 0.0 | 36.5 ± 1.2 | 11.0 ± 0.2 | 1.5 ± 0.1 | 14.2 ± 0.5 | 0.0 ± 0.0 | 0.0 ± 0.0 |
| Svcp1-NoACP1(Δ1-22) + delta12-DES + omega3-DES | 1966.9 ± 173.8 | 1.7 ± 0.0 | 33.6 ± 1.2 | 11.4 ± 0.4 | 1.4 ± 0.0 | 23.3 ± 1.2 | 0.0 ± 0.0 | 0.0 ± 0.0 |

TABLE 5-continued

| | Fatty Acid Composition (% TFA) | | | | | |
|---|---|---|---|---|---|---|
| | C18:2 (Δ9, 12) | C18:3 (Δ6, 9, 12) | C20:3 (Δ8, 11, 14) | C20:4 (Δ5, 8, 11, 14) | C20:5 (Δ5, 8, 11, 14, 17) | C20:n |
| WT (reference example) | 1.3 ± 0.0 | 0.5 ± 0.0 | 0.0 ± 0.0 | 1.5 ± 0.0 | 11.1 ± 0.1 | 12.6 ± 0.1 |
| Svcp1-NoACP1(Δ1-22) | 2.2 ± 0.0 | 1.4 ± 0.0 | 0.3 ± 0.0 | 3.0 ± 0.0 | 15.5 ± 0.1 | 18.9 ± 0.1 |
| Svcp1-NoACP1(Δ1-22) + delta9-DES | 1.9 ± 0.0 | 0.7 ± 0.1 | 0.1 ± 0.1 | 2.5 ± 0.2 | 9.9 ± 1.1 | 12.5 ± 1.4 |
| Svcp1-NoACP1(Δ1-22) + delta12-DES | 6.3 ± 0.5 | 2.6 ± 0.5 | 0.7 ± 0.1 | 4.6 ± 0.5 | 11.8 ± 1.7 | 17.1 ± 2.3 |
| Svcp1-NoACP1(Δ1-22) + omega3-DES | 1.9 ± 0.1 | 1.4 ± 0.1 | 0.2 ± 0.0 | 0.8 ± 0.1 | 16.9 ± 0.3 | 17.9 ± 0.3 |
| Svcp1-NoACP1(Δ1-22) + delta12-DES + delta9-DES | 8.5 ± 0.3 | 2.5 ± 0.1 | 1.0 ± 0.0 | 6.6 ± 0.3 | 12.3 ± 0.2 | 19.9 ± 0.3 |
| Svcp1-NoACP1(Δ1-22) + delta12-DES + delta6-DES | 1.6 ± 0.1 | 5.6 ± 0.5 | 3.4 ± 0.2 | 10.6 ± 0.7 | 13.7 ± 0.6 | 27.7 ± 1.4 |
| Svcp1-NoACP1(Δ1-22) + delta12-DES + omega3-DES | 6.6 ± 0.2 | 2.7 ± 0.1 | 0.4 ± 0.0 | 1.6 ± 0.1 | 17.1 ± 0.7 | 19.2 ± 0.5 |

As shown in Table 5, in the strain into which the Svcp1-NoACP1(Δ1-22) gene and the Δ9-DES gene were introduced, a proportion of the amount of C18:1(Δ9) was further increased, in comparison with that in the Svcp1-NoACP1(Δ1-22) strain.

Further, in the strain into which the Svcp1-NoACP1(Δ1-22) gene and the Δ12-DES gene were introduced, a proportion of the amount of C18:2(Δ9,12) was further improved, in comparison with that in the Svcp1-NoACP1(Δ1-22) strain.

Further, in the strain into which the Svcp1-NoACP1(Δ1-22) gene and the ω3-DES gene were introduced, a proportion of the amount of C20:5(Δ5,8,11,14,17) was further increased, in comparison with that in the Svcp1-NoACP1(Δ1-22) strain.

Further, in the strain into which the Svcp1-NoACP1(Δ1-22) gene, the Δ12-DES gene and the Δ9-DES gene were introduced, a proportion of the amount of C18:2(Δ9,12) was furthermore improved in comparison with that in the Svcp1-NoACP1(Δ1-22) strain, the strain into which the Svcp1-NoACP1(Δ1-22) gene and the Δ9-DES gene were introduced, or the strain into which the Svcp1-NoACP1(Δ1-22) gene and the Δ12-DES gene were introduced.

Further, in the strain into which the Svcp1-NoACP1(Δ1-22) gene, the Δ12-DES gene and the ω3-DES gene were introduced, proportions of the amount of C20:5(Δ5,8,11,14,17) and the amount of C20:n were furthermore improved in comparison with those in the Svcp1-NoACP1(Δ1-22) strain, the strain into which the Svcp1-NoACP1(Δ1-22) gene and the Δ12-DES gene were introduced, or the strain into which the Svcp1-NoACP1(Δ1-22) gene and the ω3-DES gene were introduced.

Further, in the strain into which the Svcp1-NoACP1(Δ1-22) gene, the Δ12-DES gene, and the Δ6-DES gene were introduced, proportions of the amount of C18:3(Δ6,9,12), and the amount of C20:n (especially, C20:3(Δ8,11,14) and C20:4(Δ5,8,11,14)) were further improved in comparison with those in the Svcp1-NoACP1(Δ1-22) strain, or the strain into which the Svcp1-NoACP1(Δ1-22) gene and the Δ12-DES gene were introduced.

Thus, it became apparent that the proportion or the productivity of desired long-chain polyunsaturated fatty acids is improved by reinforcing expression of a suitable desaturase gene in addition to the NoACP1 gene specified in the present invention.

As described above, the transformant in which the productivity of the long-chain fatty acids is improved can be prepared by introducing a gene encoding the ACP specified in the present invention. Further, the productivity of the long-chain fatty acids can be improved by culturing this transformant.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2016-188294 filed in Japan on Sep. 27, 2016, which is entirely herein incorporated by reference.

What is claimed is:

1. A method of producing lipids, comprising the steps of:
   culturing a transformant into which a gene encoding at least one of the proteins selected from the group consisting of proteins (A), (B), and (C) has been introduced;
   expressing the protein encoded by the gene during the culturing; and
   producing fatty acids or lipids containing the same as components;
   wherein proteins (A), (B) and (C) are:
   (A) A protein consisting of the amino acid sequence of the 23$^{rd}$ to 146$^{th}$ amino acids set forth in SEQ ID NO: 1;
   (B) A protein consisting of an amino acid sequence having 90% or more identity with the amino acid sequence of protein (A), and having acyl carrier protein activity; and
   (C) A protein comprising the amino acid sequence of protein (A) or (B), and having acyl carrier protein activity.

2. A method of improving the productivity of long-chain fatty acids or lipids containing the same, comprising the steps of:
   culturing a *Nannochloropsis* transformant into which a gene encoding at least one of the proteins selected from the group consisting of proteins (A), (B), and (C) has been introduced;
   expressing the protein encoded by the gene; and
   producing long-chain fatty acids or lipids containing the same during the culturing;
   wherein expressing the protein encoded by the gene increases the concentration of protein (A) or (B) in chloroplasts of the transformant as compared to the concentration of protein (A) or (B) in chloroplasts of the transformant's wild-type host strain that was not transformed with the gene;
   wherein the transformant's productivity of long-chain fatty acids or lipids containing the same as components is improved as compared to that of the transformant's wild-type host that was not transformed with the gene; and
   wherein proteins (A), (B) and (C) are:
   (A) A protein consisting of the amino acid sequence of the 23$^{rd}$ to 146$^{th}$ amino acids set forth in SEQ ID NO: 1;
   (B) A protein consisting of an amino acid sequence having 90% or more identity with the amino acid sequence of protein (A), and having acyl carrier protein activity; and
   (C) A protein comprising the amino acid sequence of protein (A) or (B), and having acyl carrier protein activity.

3. The method according to claim 1, wherein protein (C) is protein (C1):
   (C1) A protein wherein a chloroplast transit signal peptide that functions in the transformant is operably linked to the N terminal side of the amino acid sequence of protein (A) or (B).

4. The method according to claim 1, wherein expression of a desaturase gene is enhanced in the transformant, and wherein the desaturase is at least one desaturase selected from the group consisting of a Δ12-desaturase, a Δ6-desaturase, an ω3-desaturase, and a Δ9-desaturase.

5. The method according to claim 1, wherein the transformant is a transformant of an alga belonging to the genus *Nannochloropsis*.

6. The method according to claim 1, wherein the fatty acids or lipids that are produced comprise a long-chain fatty acid or a fatty acid ester compound thereof.

7. A transformant that has been transformed with a gene encoding at least one protein selected from the group consisting of proteins (A), (B), (C), and (C1), wherein proteins (A), (B), (C), and (C1) are:
   (A) A protein consisting of the amino acid sequence of the 23$^{rd}$ to 146$^{th}$ amino acids set forth in SEQ ID NO: 1;
   (B) A protein consisting of an amino acid sequence having 90% or more identity with the amino acid sequence of protein (A) and having acyl carrier protein activity;
   (C) A protein comprising the amino acid sequence of protein (A) or (B), and having acyl carrier protein activity; and
   (C1) A protein comprising a chloroplast transit signal peptide operably linked to the N terminal side of the amino acid sequence of protein (A) or (B).

8. The transformant according to claim 7, wherein expression of a desaturase gene is enhanced, and wherein the desaturase is at least one desaturase selected from the group consisting of a Δ12-desaturase, a Δ6-desaturase, an ω3-desaturase, and a Δ9-desaturase.

9. The transformant of claim 7, wherein the transformant is a transformant of an alga belonging to the genus *Nannochloropsis*.

10. A recombinant vector or DNA cassette comprising a gene encoding at least one protein selected from the group consisting of proteins (A), (B), (C), and (C1), wherein proteins (A), (B), (C), and (C1) are:
    (A) A protein consisting of the amino acid sequence of the 23$^{rd}$ to 146$^{th}$ amino acids set forth in SEQ ID NO: 1;
    (B) A protein consisting of an amino acid sequence having 90% or more identity with the amino acid sequence of protein (A) and having acyl carrier protein activity;
    (C) A protein comprising the amino acid sequence of protein (A) or (B), and having acyl carrier protein activity; and
    (C1) A protein comprising a chloroplast transit signal peptide operably linked to the N terminal side of the amino acid sequence of protein (A) or (B).

11. The method according to claim 2, wherein expression of a desaturase gene is enhanced in the transformant and wherein the desaturase is at least one desaturase selected from the group consisting of a Δ12-desaturase, a Δ6-desaturase, an ω3-desaturase, and a Δ9-desaturase.

12. The method according to claim 2, wherein the fatty acids or lipids that are produced comprise a long-chain fatty acid having 18 or more carbon atoms or a fatty acid ester compound thereof.

13. The vector or DNA cassette of claim 10, wherein the protein is protein (C1).

* * * * *